(12) United States Patent
Kim et al.

(10) Patent No.: US 7,033,819 B2
(45) Date of Patent: *Apr. 25, 2006

(54) SYSTEM FOR MONITORING CELL MOTILITY IN REAL-TIME

(75) Inventors: Enoch Kim, Boston, MA (US); Gregory L. Kirk, Winchester, MA (US); Olivier Schueller, Arlington, MA (US); Emanuele Ostuni, Watertown, MA (US)

(73) Assignee: Surface Logix, Inc., Brighton, MA (US)

( * ) Notice: Subject to any disclaimer, the term of this patent is extended or adjusted under 35 U.S.C. 154(b) by 181 days.

This patent is subject to a terminal disclaimer.

(21) Appl. No.: 10/206,196

(22) Filed: Jul. 29, 2002

(65) Prior Publication Data

US 2003/0040031 A1    Feb. 27, 2003

Related U.S. Application Data

(63) Continuation-in-part of application No. 09/709,776, filed on Nov. 8, 2000, now Pat. No. 6,699,665.

(60) Provisional application No. 60/374,799, filed on Apr. 24, 2002, provisional application No. 60/363,355, filed on Mar. 12, 2002, provisional application No. 60/334,548, filed on Dec. 3, 2001, provisional application No. 60/330,456, filed on Oct. 22, 2001, provisional application No. 60/328,103, filed on Oct. 11, 2001, provisional application No. 60/323,742, filed on Sep. 21, 2001, provisional application No. 60/307,886, filed on Jul. 27, 2001.

(51) Int. Cl.
*C12M 1/36* (2006.01)

(52) U.S. Cl. ............. 435/286.2; 435/288.5; 435/288.7; 422/102

(58) Field of Classification Search ......... 435/286.1, 435/288.7, 286.2, 288.5; 422/102
See application file for complete search history.

(56) References Cited

U.S. PATENT DOCUMENTS 4,240,751 A    12/1980    Linnecke et al. ........... 356/409

(Continued)

FOREIGN PATENT DOCUMENTS

EP    1 199 354 A1    3/2002

(Continued)

OTHER PUBLICATIONS

Bernard et al., "Printing Patterns of Proteins", Langmuir, Apr. 28, 1998, vol. 14, No. 9, pp. 2226-2228.

(Continued)

*Primary Examiner*—David Redding
(74) *Attorney, Agent, or Firm*—Kenyon & Kenyon LLP

(57) ABSTRACT

The invention relates to devices, devices for arraying biomolecules, including cells, methods for arraying biomolecules, assays for monitoring cellular movement, and systems for monitoring cellular movement. The devices include a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; and a second layer configured to be placed in fluid-tight contact with the upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well.

6 Claims, 33 Drawing Sheets

U.S. PATENT DOCUMENTS

| | | | |
|---|---|---|---|
| 4,728,591 A | 3/1988 | Clark et al. ............... 430/5 |
| 4,789,601 A | 12/1988 | Banes .................. 428/447 |
| 4,802,951 A | 2/1989 | Clark et al. ............ 156/630 |
| 4,831,869 A | 5/1989 | Fowler ................ 73/150 A |
| 4,842,633 A | 6/1989 | Kuribayashi et al. ....... 65/44 |
| 4,912,057 A | 3/1990 | Guirguis ............... 435/285 |
| 4,999,489 A | 3/1991 | Huggins ............... 250/226 |
| 5,072,382 A | 12/1991 | Kamentsky ......... 364/413.08 |
| 5,079,600 A | 1/1992 | Schnur et al. ............. 357/4 |
| 5,120,662 A | 6/1992 | Chan et al. ............ 436/530 |
| 5,143,854 A | 9/1992 | Pirrung et al. ......... 436/518 |
| 5,202,227 A | 4/1993 | Matsuda et al. ........ 430/320 |
| 5,224,058 A | 6/1993 | Mickaels et al. ....... 364/554 |
| 5,278,063 A | 1/1994 | Hubbell et al. ..... 435/240.243 |
| 5,312,731 A | 5/1994 | Engstrom ................ 435/32 |
| 5,324,591 A | 6/1994 | Georger, Jr. et al. ..... 428/552 |
| 5,330,911 A | 7/1994 | Hubbell et al. ..... 435/240.243 |
| 5,424,213 A | 6/1995 | Mougin ................. 436/63 |
| 5,427,663 A | 6/1995 | Austin ................ 204/180.1 |
| 5,470,739 A | 11/1995 | Akaike et al. ...... 435/240.243 |
| 5,492,890 A | 2/1996 | Ginsberg et al. .......... 514/12 |
| 5,510,481 A | 4/1996 | Bednarski et al. ....... 536/120 |
| 5,512,131 A | 4/1996 | Kumar et al. ......... 156/655.1 |
| 5,514,501 A | 5/1996 | Tarlov ..................... 430/5 |
| 5,573,942 A | 11/1996 | Miyamoto ........... 435/240.23 |
| 5,591,627 A | 1/1997 | Miyamoto ........... 435/240.23 |
| 5,599,695 A | 2/1997 | Pease et al. ............ 435/91.1 |
| 5,602,029 A | 2/1997 | Miyamoto .............. 435/395 |
| 5,679,310 A | 10/1997 | Manns ................. 422/102 |
| 5,691,018 A | 11/1997 | Kelley et al. ........... 428/36.8 |
| 5,719,060 A | 2/1998 | Hutchens et al. ........ 436/174 |
| 5,721,131 A | 2/1998 | Rudolph et al. ..... 435/240.243 |
| 5,744,366 A | 4/1998 | Kricka et al. ............ 436/63 |
| 5,776,748 A | 7/1998 | Singhvi et al. .......... 435/180 |
| 5,828,776 A | 10/1998 | Lee et al. ............... 382/133 |
| 5,840,256 A | 11/1998 | Demers et al. .......... 422/102 |
| 5,856,082 A | 1/1999 | Aebersold et al. .......... 435/4 |
| 5,858,801 A | 1/1999 | Brizzolara ............. 436/518 |
| 5,866,321 A | 2/1999 | Matsue .................... 435/5 |
| 5,894,063 A | 4/1999 | Hutchens et al. ........ 436/155 |
| 5,900,160 A | 5/1999 | Whitesides et al. ........ 216/41 |
| 5,935,850 A | 8/1999 | Clark et al. ............. 435/325 |
| 5,942,443 A | 8/1999 | Parce et al. ............. 436/514 |
| 5,976,826 A | 11/1999 | Singhvi et al. ........... 435/29 |
| 5,986,835 A | 11/1999 | Kurusu et al. ............ 360/53 |
| 6,001,556 A | 12/1999 | Charych et al. ............ 435/5 |
| 6,008,010 A | 12/1999 | Greenberger et al. ...... 435/41 |
| 6,020,208 A | 2/2000 | Hutchens et al. ........ 436/174 |
| 6,027,942 A | 2/2000 | Hutchens et al. ........ 436/173 |
| 6,037,171 A | 3/2000 | Larsson ............... 435/297.1 |
| 6,039,897 A | 3/2000 | Lochhead ............... 264/1.24 |
| 6,071,610 A | 6/2000 | Jarrell et al. ............ 428/335 |
| 6,096,510 A | 8/2000 | Hochman ............... 435/29 |
| 6,100,043 A | 8/2000 | Bridgham et al. ......... 435/7.1 |
| 6,103,479 A | 8/2000 | Taylor .................. 435/7.2 |
| 6,127,129 A | 10/2000 | Corn et al. ................ 435/6 |
| 6,133,030 A | 10/2000 | Bhatia et al. ............ 435/373 |
| 6,136,592 A | 10/2000 | Leighton et al. ........ 435/288.7 |
| 6,140,045 A | 10/2000 | Wholstadter et al. ........ 435/6 |
| 6,143,247 A | 11/2000 | Sheepard, Jr. et al. ...... 422/63 |
| 6,180,239 B1 | 1/2001 | Whitesides et al. ...... 428/411.1 |
| 6,207,369 B1 | 3/2001 | Wohlstadter .............. 435/6 |
| 6,221,579 B1 | 4/2001 | Everhart et al. ............ 435/5 |
| 6,238,874 B1 | 5/2001 | Jarnagin et al. ......... 435/7.21 |
| 6,251,672 B1 | 6/2001 | Kubbies et al. .......... 435/395 |
| 6,270,980 B1 | 8/2001 | Fritz et al. .............. 435/7.2 |
| 6,280,967 B1 | 8/2001 | Ransom ................ 435/29 |
| 6,329,164 B1 | 12/2001 | Goodwin, Jr. et al. ...... 435/29 |
| 6,368,877 B1 | 4/2002 | Zhang et al. ............ 436/527 |
| 6,558,904 B1 | 5/2003 | Ermantraut et al. .......... 435/6 |
| 6,699,665 B1 * | 3/2004 | Kim et al. ................ 435/6 |

FOREIGN PATENT DOCUMENTS

| | | |
|---|---|---|
| WO | WO 98/36827 | 8/1998 |
| WO | WO 98/38490 | 9/1998 |
| WO | WO 98/58967 | 12/1998 |
| WO | WO 99/54786 | 10/1999 |
| WO | WO 00/60356 | 10/2000 |
| WO | WO 00/67028 | 11/2000 |
| WO | 2001 0001644 A1 | 5/2001 |
| WO | WO 01/70389 A2 | 9/2001 |
| WO | 2001 0053527 | 12/2001 |
| WO | 2002 0012953 | 1/2002 |
| WO | WO 02/04113 A2 | 1/2002 |

OTHER PUBLICATIONS

Branch et al., "Microstamp patterns of biomolecules for high-resolution neuronal networks", Medical & Biological Engineering & Computing, 1998, vol. 36, pp. 135-141.

Duffy et al., "Patterning Electroluminescent Materials with Feature Sizes as Small as 5 μm Using Elastromeric Membranes as Masks for Dry Lift-Off", Advanced Materials, vol. 11 No. 7, pp. 546 552.

Folch et al., "Cellular Micropatterns on Biocompatible Materials", Biotechol. Prog., 1998, vol. 14 No. 3, pp. 388-392.

Gonzalez et al., "Intracellular detection assays for high-throughout screening", Current Opinion in Biotechnology, 1998, 9:624-631.

Hale, "Irreversible, Oriented Immobilization of Antibodies to Cobalt-Iminodiacetate Resin for Use as Immunoaffinity Media", Analytical Biochemistry, 1995, 231, 46-49.

Kind et al., "Patterned Electroless Deposition of Copper by Microcontact Printing Palladium(II) Complexes on Titanium-Covered Surfaces" Langmuir, Aug. 8, 2000, vol. 16, N. 16, pp. 6367-6373.

Jackman et al., "Using Elastomeric Membranes as Dry Resists and for Dry Lift-Off", Langmuir, 1999, vol. 15, pp. 2973-2984.

Jackman et al., "Fabricating Large Arrays of Microwells with Arbitrary Dimensions and Filling Them Using Discontinuous Dewetting", Anal. Chem., 1998, 2280-2287.

Mere et al, "Miniaturized FRET assays and microfluidics: key components for ulta-high throughput screening", DDT, Aug. 8, 1999, vol. 4 363-369.

Saleemuddin, "Binaffinity Based Immobilization of Enzymes", Advances in Biochemical Engineering/Biotechnology, 1999, vol. 64, pp. 204-226.

Sigal et al., "A Self-Assembled Monolayer for the Binding and Study of Histidine-Tagged Proteins by Surface Plasmon Resonance", Anal. Chem., 1996, 68, 490-497.

Sigal et al., "Using Surface Plasmon Resonance Spectroscopy To Measure the Association of Detergents with Self-Assembled Monolayers of Hexadecanethiolate on Gold", Langmuir, 1997, 13, pp. 2749-2755.

Sittampalam et al, "High-throughput screening: advances in assay technologies", Current Opinion in Chemical Biology, 1997, 1:384-391.

Xia et al., "Soft Lithography", Angew. Chem. Ins. Ed., 1998, vol. 37, pp. 551-575.

Bhatia et al. "Probing heterotypic cell interactions: Hepatocyte function in microfabricated co-cultures," Science Polymer Edition, vol. 9, No. 11, pp. 1137-1160 (1998).

Bhatia et al., "Selective Adhesion of Hepatocytes on Patterned Surfaces," Annals of the New York Academy of Science, vol. 745, pp. 187-209 (1994).

Bhatia et al., "Effect of cell-cell interactions in preservation of cellular phenotype: cocultivation of hepatocytes and nonparenchymal cells," The FASEB Journal, vol. 13, pp. 1883-1900 (1999.

Bhatia et al., "Controlling cell interactions by micropatterning in co-cultures: Hepatocytes and #T3 fibroblasts," Journal of Biomedical Materials Research, vol. 34, pp. 189-199 (1997).

Chen et al., "Using Self-Assembled Monolayers to Pattern ECM Proteins and Cells on Substrates," Methods In Molecular Biology—Extracellular, Matrix Protocols, pp. 209-218.

Chen et al., "Micropatterned Surfaces for Control of Cell Shape, Position, and Function," 1998 Biotechnol. Prog. 1998, vol. 14, pp. 356-3643.

Chiu et al., "Patterned Deposition of Cells and Proteins onto Surfaces by Using Three-dimensional Microfluidic Systems," PNAS (Proceedings of the National Academy of Sciences of the United States of America), Mar. 14, 2000, vol. 97, No. 6, pp. 2399-2958.

Duffy et al., "Multiplexed Kinase Assays Using a Combination of Peptides Immobilized on Self-Assembled Monolayers (SAMs) and Hybrid, Elastomeric Micro-Titer Plates, "Dec. 11, 2001, pp. 1-13.

Duncan et al., "Laser microfabricated model surfaces for controlled cell growth," Biosensors & Bioelectronics, 17, 413-426 (2002.

Folch et al., "Microfabricated elastomeric stencils for micropatterning cell cultures," John Wiley & Son, Inc. Mar. 9, 2000, 346-353.

Folch et al, "Microengineering of Cellular Interactions," Annual Review of Biomedical Engineering, vol. 2, 2000, pp. 227-256.

Giaever et al., "Micromotion of mammalian cells measured electrically," Proc. Natl. Acad. Sci. USA, vol. 88, pp. 7896-7900 (1991).

Gray et al., "Microchannel Platform for the Study of Endothelial Cell Shape and Function," Biomedical Microdevia, 4:1, 9-16 (2002).

Gruler "Cell Movement Analysis in a Necrotactic Assay" Blood Cells vol. 10, pp. 107-121.

Hadjout et al., "Automated Real-Time Measurement of Chemotactic Cell Motility," BioTechniques vol. 31. pp. 1130-1138 (Nov. 2001).

Hirose et al, "Temperature-Responsive Surface for Novel Co-Culture Systems of Hepatocytes with Endothelial Cells: 2-D Patterned and Double Layered Co-Cultures," Yonsei Medical Journal, vol. 41, No. 6, pp. 803-813, (2000).

Hossain et al., "In Vivo Cell Tracking by Scanning Laser Ophthalmoscopy: Quantification of Leukocyte Kinetics," IVOS, vol. 39, No. 10 1879-1887 (1998).

Hoying et al., "Measurement of Endothelial Cell Migration Using an Improved Linear Migration Assay," Microcirculation, vol. 3, No. 2, 167-174 (1996).

Hyun et al., "Micropatterning Biological Molecules on a Polymer Surface using Elastomeric Microwells," Department of Biomedical Engineering Duke University.

Hyun et al., "Micropatterns of a Cell-Adhesive Peptide on an Amphiphilic Comb Polymer Film," Langmuir, vol. 18, No. 8, pp. 2975-2979 (2002).

Ito, "Surface Micropatterning to regulate cell functions," Biomaterials 20 (1999) pp. 2333-2342.

Ito et al., "Gradient micropattern immobilization of heparin and its interaction with cells," J. Biomater. Sci. Polymer Edn, vol. 12, No. 4, pp. 367-378 (2001).

Jiang et al., "Controlling Mammalian Cell Spreading and Cytoskeletal Arrangement with Conveniently Fabricated Continuous Wavy Features on Poly(dimethylsiloxane)," Langmuir, vol. 18, No. 8, 3273-3280 (2002.

Kiabara et al., "Promotion and control of selective adhesion and proliferation of endothelial cells on polymer surface by carbon deposition," Journal of Biomedical Materials Research, vol. 31, 429-435 (1996).

Kane et al., "Patterning Proteins and Cells Using Soft Lithography," Biomaterials, vol. 20 1999, pp. 2363-2376.

Krasteva et al., "The role of surface wettability on hepatocyte adhesive interactions and function," J. Biomater. Sci. Polymer Edn, vol. 12, No. 6, pp. 613-627 (2001).

Li et al., "Effects of morphological patterning on endothelial cell migration," Biorheology, 38, 101-108 (2001).

López et al., "Convenient Methods for Patterning the Adhesion of Mammalian Cells to Surfaces Using Self-Assembled Monolayers of alkanethiolates on Gold[1]," J. Am. Chem. Co. 1993, vol. 115, pp. 5877-5878.

Mitre et al, "Electric Measurements Can Be Used to Monitor the Attachment and Spreading of Cells in Tissue Culture," BioTechniques, vol. 11, No. 4, pp. 504-510 (1991).

Mrksich et al, "Using Microcontact Printing to Pattern Attachment of Mammalian Cells to Self-Assembled Monolayers of Alkanethiolates on Transparent Films of Gold and Silver," pp. 305-313.

Mrksich et al., "Controlling cell attachment on contoured surfaces with self-assembled monolayers of alkanethiolates on gold," Proc. National Academy of Science, USA.

Ostuni et al, "Patterning Mammalian Cells Using Elastomeric Membranes," Langmuir, Jun. 21, 2000.

Otsuka et al., "Novel Micropaterned Surface Fabricated from Heterobifunctional Poly(ethylene glycol)/polylactide Block Copolymers for Patterned Cell Culture," Journal of Photpolymer Science Technology, vol. 14, No. 1, 101-104 (2001).

Sundberg et al., "Spatially-Addressable Immobilization of Macromolecules on Solid Supports," J. Am. Chem. Soc., vol. 117, No. 49: 12050-12057 (1995).

Takayama et al., "Patterning the Topographical Environment for Mammalian Cell Culture Using Laminar Flows in Capillaries," Poster 10, pp. 322-325.

Takayama et al, "Patterning Cells and Their Environment using multiple laminar fluid flows in capillary networks," Prod. Natl. Acad. Science, vol. 96, pp. 5545-5548, May 1999, Cell Biology, Applied Physical Sciences.

Thomas et al, "Surfaces Designed to Control the Projected Area and Shape of Individual Cells," Journal of Biomechanical Engineering, vol. 121, pp. 40-47 (1999).

Vollmer et al., "Tumor necrosis factor-alpha decreases neutrophil chemotaxis to N-formyl-l-methionyl-1-leucy-1-phenylalanine: analysis of single cell movement." Journal of Leukocyte Biology; vol. 52, No. 6, pp. 630-636, (Dec. 1992).

Yamato et al., "Thermally responsive polymer-grafted surfaces facilitate patterned cell seeding and co-culture," Biomaterials 23, 561-567 (2002).

Yousaf et al., "Dynamic substrates: modulating the behaviors of attached cells," New technologies for life sciences: A Trends Guide, 28-35 (2000).

* cited by examiner

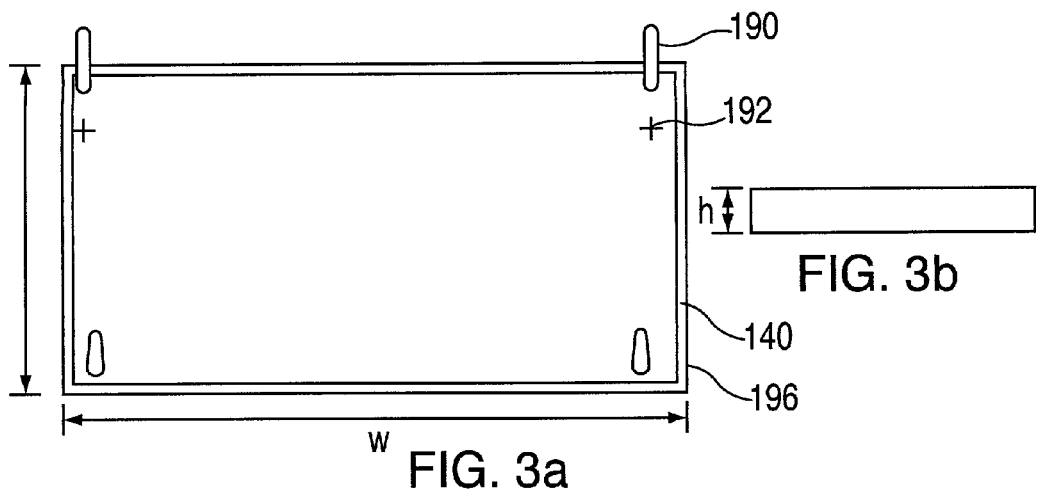
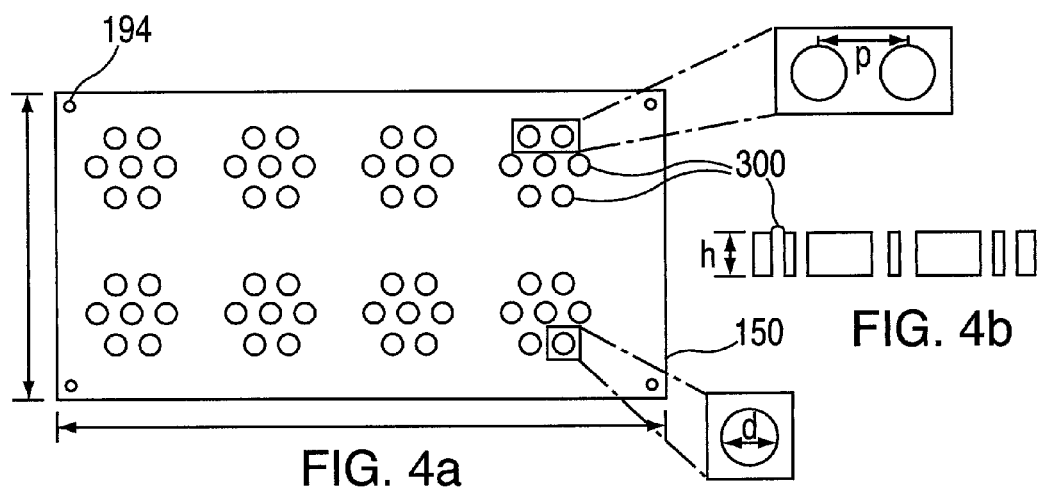
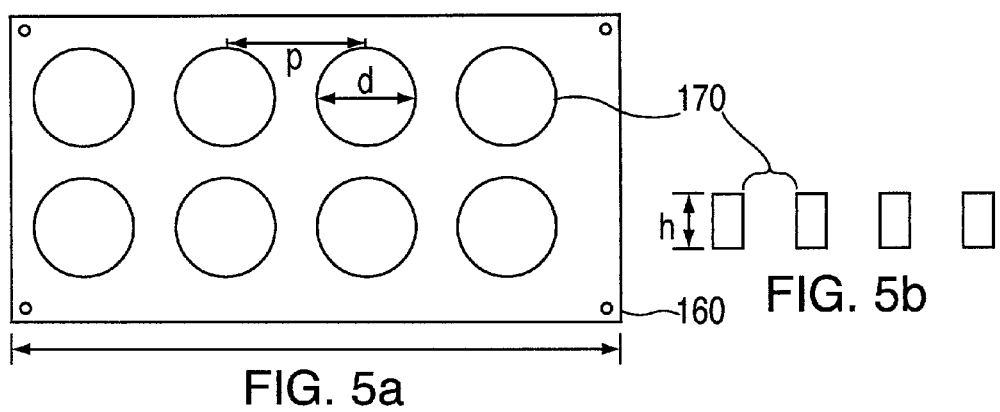

PDMS CASTING

96 WELL PLATE

1) PLACE PDMS MACROPOSTS

2) POUR PDMS

3) CURE AND REMOVE MACROPOSTS

1) PLACE PDMS MACROPOSTS

2) POUR PDMS AND PULL VACUUM

3) CURE AND REMOVE MACROPOSTS

MS1
(ENDOTHELIAL)

3T3
(FIBROBLAST)

OVERLAY

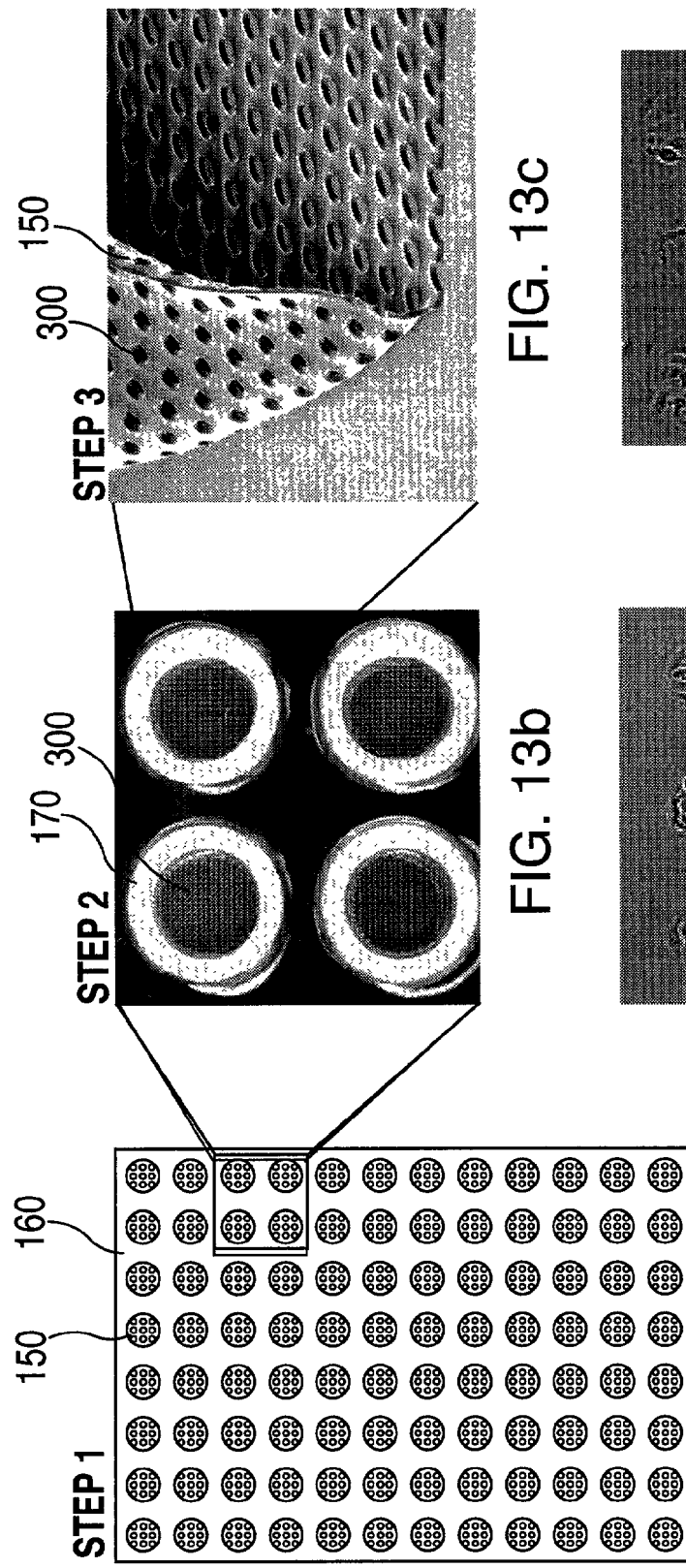

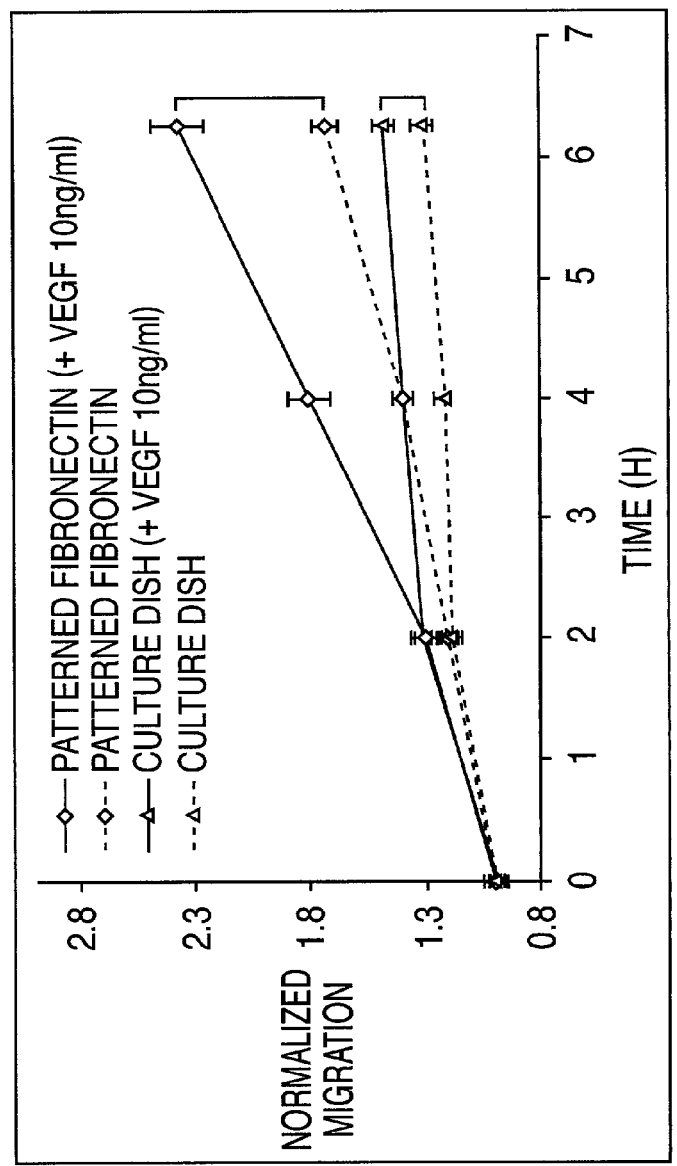
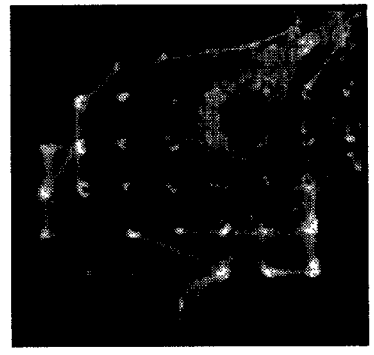
FIG. 26

SYSTEM FOR MONITORING CELL MOTILITY IN REAL-TIME

RELATED APPLICATIONS

This application is a continuation in part of U.S. application Ser. No. 09/709,776, filed on Nov. 8, 2000, now U.S. Pat. No. 6,699,665. This application also claims the benefit of and incorporates herein by reference, in their entirety: U.S. Provisional Application No. 60/307,886, filed on Jul. 27, 2001; U.S. Provisional Application No. 60/323,742, filed on Sep. 21, 2001; U.S. Provisional Application No. 60/328,103, filed on Oct. 11, 2001; U.S. Provisional Application No. 60/330,456, filed on Oct. 22, 2001; U.S. Provisional Application No. 60/334,548, filed on Dec. 3, 2001; U.S. Provisional Application No. 60/363,355, filed on Mar. 12, 2002; and U.S. Provisional Application No. 60/374,799, filed on Apr. 24, 2002.

FIELD OF THE INVENTION

The invention generally relates to devices and methods for patterning cells in a predetermined array for subsequent observation and measurement of cell motility.

BACKGROUND

The study of cellular behavior and the effects of external stimuli on the cell are prevalent throughout contemporary biological research. Generally, this research involves exposing a cell to external stimuli and studying the cell's reaction. By placing a living cell into various environments and exposing it to different external stimuli, both the internal workings of the cell and the effects of the external stimuli on the cell can be measured, recorded, and better understood.

When a cell is exposed to chemical stimuli, its behavior is an important consideration, particularly when developing and evaluating therapeutic candidates and their effectiveness. By documenting the reaction of a cell or a group of cells to a chemical stimulus, such as a therapeutic agent, the effectiveness of the chemical stimulus can be better understood. In particular, in the fields of oncology and cell biology, cell migration and metastasis are regularly considered. Typically, studies in these fields involve analyzing the migration and behavior of living cells with regard to various biological factors and potential anti-cancer drugs. Moreover, the resultant migration, differentiation, and behavior of a cell are often insightful towards further understanding the chemotactic processes involved in tumor cell metastasis. In addition, these studies can also provide insight into the processes of tissue regeneration, wound healing, inflamation, autoimmune diseases, and many other degenerative diseases and conditions.

Cell migration assays are often used in conducting these types of research. Commercially available devices for creating such assays are often based on or employ a Boyden chamber (a vessel partitioned by a thin porous membrane to form two distinct, super-imposed chambers). Also known as transwells, the Boyden chamber is used by placing a migratory stimulus on one side of a thin porous membrane and cells to be studied on the other. After a sufficient incubation period the cells may be fixed, stained, and counted to study the effects of the stimulus on cell migration across the membrane.

The use of transwells has several shortcomings. For instance, assays employing transwells require a labor-intensive protocol that is not readily adaptable to high-throughput screening and processing. The counting of cells, which is often done manually using a microscope, is a time-consuming, tedious, and expensive process. Furthermore, cell counting is also subjective and involves statistical approximations. Specifically, due to the time and expense associated with examining an entire filter, only representative areas, selected at random, may be counted, and, even when these areas are counted, if a cell has only partially migrated through the filter, a technician must, nevertheless, exercise his or her judgement when accounting for such a cell.

Notwithstanding the above, perhaps the most significant disadvantage to the use of transwells is that when the cells are fixed to a slide, as required for observation, they are killed. Consequently, once a cell is observed it can no longer be reintroduced into the assay or studied at subsequent periods of exposure to the stimulus. Therefore, in order to study the progress of a cell reaction to a stimulus, it is necessary to run concurrent samples that may be slated for observation at various time periods before and after the introduction of the stimulus. In light of the multiple samples required for each test, in addition to the positive and negative controls required to obtain reliable data, a single chemotaxis assay can require dozens of filters, each of which needs to be individually examined and counted—an enormous and onerous task.

Cell migration and differentiation is also important to the understanding of numerous biological functions, both normal and abnormal. For example, the study of tissue regeneration and wound healing, and the study of inflamation, autoimmune diseases and other degenerative diseases, all involve the analysis of cell movement, either spontaneous or in response to chemotactic factors, or other cellular signals. Further, in studying the treatment of various abnormal cellular functions or diseases, scientists must analyze the effects of potential therapies on cell movement in cell culture before proceeding to clinical studies.

Thus, a cell migration assay is a useful tool for cell biologists for determining the ability of cells to grow, proliferate, and migrate. Although useful, assays based on cell migration have been limited in use because of the unavailability of convenient tools for performing the assay. Currently, commercially available devices for studying cell migration or chemotaxis are based on the Boyden Chamber. S. Boyden, *J Exp. Med*. 115: pp. 453–466, (1962). Also known as transwells, these devices are used generally as follows: a migratory stimulus is added to one side of a thin porous membrane; cells are then added to the other side, and the device is incubated. After a given time, cells that have not migrated across the membrane are removed, and the cells that have migrated are counted, usually after fixing and staining.

There are several disadvantages to this procedure. The use of a Boyden Chamber requires a labor-intensive protocol, and it is not readily adaptable to a high-throughput screening process. The examination and counting of the cells on the filter is time-consuming, tedious, and expensive. It is also highly subjective because it necessarily involves the exercise of judgment in determining whether to count a cell that has only partially migrated across the filter. In addition, the time and expense associated with examining the entire filter necessitates that only representative areas, selected at random, be counted, thus rendering the results less accurate than would otherwise be the case if the entire filter were examined and counted.

Perhaps the most important disadvantage in this procedure is that the fixing step kills the cells. That is, the procedure is destructive of the cell sample. Thus, in order to determine a time-dependent relationship of the chemotactic response; that is, a kinetic study, of a particular chemical agent, it is necessary to run multiple samples for each of multiple time periods. When one considers that multiple samples, as well as positive and negative controls, are necessary to obtain reliable data, a single chemotaxis assay can produce dozens of filters, each of which needs to be individually examined and counted. The time and expense associated with a time-dependent study is usually prohibitive of conducting such a study using the Boyden procedure. As the migratory behavior of cells has potential implications in the development of certain therapeutics, a better in vitro system is needed for screening and quantifying the effects of drug targets on cell motility and migration.

Alternatives to the Boyden assay have been proposed to overcome some of the above disadvantages. See generally, P. Wilkinson, *Methods in Enzymology*, Vol. 162, (Academic Press, Inc. 1988), pp. 38–50; see also, Goodwin, U.S. Pat. No. 5,302,515; Guiruis et al., U.S. Pat. No. 4,912,057; Goodwin, U.S. Pat. No. 5,284,753; and Goodwin, U.S. Pat. No. 5,210,021. Although the chemotaxis devices and procedures described in these references have some advantages over the original Boyden procedure and apparatus, they are not without their shortcomings. For example, all of these procedures, like the Boyden Chamber, require that the filter be removed and the non-migrated cells be wiped or brushed from the filter before the migrated cells can be counted. In addition, most of these procedures require fixing and staining the cells, and none of them permit the kinetic or time-dependent study of the chemotactic response of the same cell sample. Further, these methods involve the counting of cells, a lengthy procedure not compatible with high-throughput applications.

Cell migration is important for tissue morphogenesis. Much progress has been made in terms of understanding the molecular basis of cell movement. However, because of the inherent complexity of multicellular systems, little is known about how cell migration mediates cellular pattern formation. Bragwynne et al. (Proceedings of the 22nd Annual International Conference, Jul. 23–28, 2000) report spontaneous pattern generation in a model mammalian tissue in vitro by spatially constraining cell adhesion. They observed coupled, coordinated migration of bovine capillary endothelial cells within a field defined by spatial limits of an adhesive surface. Bragwynne et al. have speculated that pattern-generating behavior that emerges from collective interactions among different interacting cellular components may contribute to tissue development. Bragwynne et al. surmise that the resulting cell patterns demonstrate that a geometric constraint on a group of migratory cells can induce spontaneous pattern formation. Thus, in order to more fully understand spontaneous pattern formation it is necessary to have a device that would allow one to pattern cells in a predetermined location in a predefined pattern and observe their migration and spontaneous pattern formation.

The role of cell-cell interactions in the control of cellular growth, migration, differentiation, and function is becoming increasingly apparent. Cell-cell contact is believed to be involved in developmental process such as mesoderm interaction and mesenchymal-epithelial transformation. Sargent, T. D., et al., *Dev. Biol.* 114:238–246 (1986); Lehtonen, E., et al., *J. Embryol. Exp. Morphol.* 33:187–203 (1975). In the nervous system, the pattern of neural cell migration axonal cone growth and glial cell differentiation are thought to depend on heterolytic cell-cell interactions. Rakic, P., *The cell in contact*, New York: Wiley Intersciences, 67–91 (1985); Bently, D., et al., *Nature* 304:62–65 (1983); Lillien, L., et al., *Neuron* 4:525–534 (1990). In the immune system, the development and activation of lymphocytes are dependent on contact with a number of different cell types throughout the life of a lymphocyte. Kierny, P. C., et al., *Blood* 70:1418–1424 (1987). In addition, the differentiation and function of epithelial cells, e.g. intestinal epithelia, are regulated in part by contacts with the underlying mesenchymal cells. Kedinger, M., et al., *Cell Differ.* 20:171–182 (1987). As the role of heterocellular contact becomes more apparent, in vitro systems designed to investigate intercellular communication are needed.

A number of experimental approaches utilizing co-cultures of two different tissue or cell types have been used to examine the role of intercellular communication in various cellular processes. For example, the contribution of cell-cell interactions to embryonic inductive processes was elucidated by experiments in which pieces of embryonic tissue were attached to opposite sides of a porous membrane. Grobstein, C., *Exp. Cell Res.* 10:424–440 (1956). Investigations of the effects of heterotypic interactions on cellular functions have co-cultured two different cell types in the same culture dish. Davies, P. F., et al., *J Cell Biol.* 101: 871–879 (1985); Guguen-Guillouzo, C., et al., *Exp. Cell Res.* 143:47–54 (1983); Mehta, R. P., et al., *Cell* 44:187–196 (1986); Orlidge, A., et al., *J Cell Biol.* 105:1455–1462 (1987); Shimaoka, S., et al., *Exp. Cell Res.* 172:228–242 (1987). These co-cultures have limited use, however, because they represent a mixed population of cells. The effects of intercellular contact on cell morphology or on a function or protein unique to one of the cell types can be examined; however, investigation of biochemical or molecular processes common to both cells in not possible. Porous filters have been used in co-cultures of tissue culture cells to circumvent this limitation. In these studies, one cell type is usually grown in a tissue culture dish and second cell type cultured on a porous membrane in a chamber that fits into the culture dish. Hisanaga, K., et al., *Dev. Brain Res.* 54:151–160 (1990); Kruegar, G. G., et al., *Dermatologic* 179:91S–100S (1989); Ueda, H., et al., *J. Cell Sci.* 89:175–188 (1988).

It has been determined that many factors operate synergistically to produce an effect on cellular migration. For example, Woodward et al., *Journal of Cell Science* 111, 469–478 (1998) have used a migration chamber to demonstrate that $\alpha_v\beta_3$ integrin and PDGF receptor work synergistically to increase cell migration. Thus, an assay device or method that would allow further study of cell migration in response to various factors, including synergistic effects, would aid in the understanding of cellular motility and migration.

To study cell motility, either in response to a cell affecting agent, or random motility, it is desirable to be able to monitor cellular movement from a predefined "starting" position. To do this, cells must be placed, attached or immobilized upon a surface in such a manner that their viability is maintained and that their position is defineable so that multiple interrogations or probing of cellular response (i.e. motility or lack thereof) may be performed. In previous methods concerning cell immobilization, cells often undergo a nonreversible immobilization. For example, cells have been immobilized by patterning cells on a self-assembled monolayer that has a protein tether that will "capture" the cell. Alternatively, cells have been immobilized via immunological reaction with antibodies, which themselves have been immobilized on the immobilization surface. Other methods of immobilization involve simply allowing cells to attach themselves to a suitable surface, such as glass or plastic, and then allowing them to migrate into adjacent areas.

Ostuni et al. have used elastomeric membranes to pattern the attachment of cells to surfaces that are commonly used in cell culture. Patterning of cells is an experimental protocol that is broadly useful in studying and controlling the behavior of anchorage-dependent cells. Chen, C. S., et al., *Science*, 276, 1425–1428 (1997); Ingber, D. E., et al., *J. Cell Biol.* 109, 317–330 (1989); Ingber, D. E. *Proc. Natl. Acad. Sci. U.S.A.*, 87, 3379–3583 (1990); Singhvi, R.; et al., *Science* 264, 696–698 (1994). It is also relevant to applied cell biology, bio-sensors, high-throughput screening and tissue engineering. Chen, et al., *Science* 276, 1425–1428 (1997); Bhatia, S. N. et al., *Biotechnol. J.* 14, 378–387 (1998); Borkholder, D. A., et al., *J Neurosci. Methods,* 77, 61–66 (1997); Dodd, S. J., et al., *Biophys. J.,* 76, 103–109 (1999); Fromherz, P., *Phys. Rev. Lett.* 78, 4131–4134; Hickman, J. J., et al., *J. Vac. Sci. Technol., A-Vac. Surf. Films* 12, 607–616 (1994); Humes, H. D., et al., *Nat. Biotechnol.* 17, 451–455 (1999); Huynh, T., et al., *Nat. Biotechnol.* 17, 1088–1086 (1999); Kapur, R., et al., *J. Biomech. Eng.- Trans. ASME* 121, 65–72 (1999); Pancrazio, J. J., et al., *Sens. Actuators, B-Chem.* 53, 179–185 (1998); St. John, P. M., et al., *Anal. Chem.* 70, 1108–1111 (1998); You, A. J., et al., *Chem., Biol.* 4, 969–975 (1997).

Soft lithography has been developed to provide a set of methods for patterning surfaces and fabricating structures with dimensions in the 1–100 μm range in ways that are useful in cell biology and biochemistry. Qin, D., et al., *Adv. Mater.* 8, 917–919 (1996); Qin, D., et al., *J. Vac. Sci., Technol.*, B 16, 98–103 (1998); Xia, Y., et al., *Agnew. Chem., Int. Ed. Engl.* 37, 550–575 (1998); Zhao, X.-M., et al., *Adv. Mater.* 8, 837–840 (1996); Zhao, X.-M., et al., *Adv. Mater.* 9, 251–254 (1997). Microcontact printing is particularly useful as a method for generating patterns of proteins and cells, by patterning self-assembled monolayers of alkanethiolates on the surface of gold. Chen, C. S., et al., *Science* 276, 1425–1428 (1997); Singhvi, R., et al., *Science* 264, 696–698 (1994); Lòpez, G. P., et al., *J. Am. Chem. Soc.* 115, 5877–5878 (1993); Kumar, A., et al., *Appl. Phys. Lett.* 63, 2002–2004 (1993); Mrksich, M., et al., *Trends Biotech.* 13, 228–235 (1995).

Mrksich et al. have partitioned a gold support into regions patterned with a hydrophobic alkanethiolate and another alkanethiolate that presents small percentages of an electrochemically active terminal group. (Yousaf, M. N.; Houseman, B. T.; Mrksich, M. Submitted.). After cells attached and spread themselves on the hydrophobic pattern, application of a short voltage pulse changed the oxidation state and polarity of the terminal redox center. This oxidation state and polarity change allowed groups presenting peptide sequences to react with the surface to generate a subsequent surface that the patterned cells could spread on. This method requires the synthesis of electroactive alkanethiols, and also requires electrochemical instrumentation.

It is further known in the art to use under agarose migration studies to assay cell differentiation and cell migration. These methods are slow and laborious and as such are not suitable to the demands of high throughput assays.

Thus, there remains a need for a device and method of tracking live cells in real time. Current existing techniques require laborious protocols and work as end-point assays.

SUMMARY OF THE INVENTION

The present invention provides a device comprising a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; and a second layer configured to be placed in fluid-tight contact with the upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well.

The first layer is preferably configured to be placed in conformal contact with the support when the first layer is placed against the support. The second layer is preferably configured to be placed in conformal contact with the first layer when the second layer is placed against the first layer. The support is made of a material selected from the group consisting of glass, silicon, fused silica, metal films, polystyrene, poly(methylacrylate) and polycarbonate. The first layer and the second layer are made of a material selected from the group consisting of glass, elastomers, rigid plastics, metals, silicon and silicon dioxide. Preferably the first layer and second layer are made of an elastomer. Most preferably the first layer and the second layer is made of PDMS.

Preferably each macro-region encompasses at least one micro-region and more preferably each macro-region encompasses a plurality of micro-regions.

In one embodiment the walls of each macro-well define a curve in a cross-sectional plane perpendicular to the upper surface of the first layer.

In the device at least one of the pattern of micro-orifices and the pattern of macro-orifices spatially and dimensionally corresponds to a standard microtiter plate. Preferably the at least one of the pattern of micro-orifices and the pattern of macro-orifices spatially and dimensionally corresponds to a standard microtiter plate selected from a group consisting of a 6-well microtiter plate, a 12-well microtiter plate, a 24-well microtiter plate, a 96-well microtiter plate, a 384-well microtiter plate, a 1,536-well microtiter plate, and a 9,600-well microtiter plate.

In another embodiment, the device further comprises at least one cap for enclosing at least one of the macro-wells. Preferably the devices comprises a plurality of caps for enclosing each of the macro-wells.

The device may also comprise a means for aligning the micro-orifices with the macro-orifices. The means for aligning includes a guide mechanism on at least one of the support, the first layer and the second layer. The guide mechanism includes protrusions extending from the support, and guide orifices defined in the first layer and in the second layer for receiving the protrusions therein thereby aligning respective ones of the first layer and the second layer on the support. The means for aligning includes markings on at least one of the support, the first layer and the second layer.

In another embodiment, the device comprises a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; and a second layer configured to be placed in fluid-tight contact with the support upon the removal of the first layer from the support, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well.

The present invention further provides a device comprising a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; and a second layer configured to be placed in fluid-tight contact with the support, the second layer comprising a plurality of rings, the rings defining a pattern of respective macro-orifices, each ring having walls and defining a macro-region when the second layer is placed in fluid-tight contact with the support such that the walls of the ring and the macro-region together define a macro-well.

The invention further comprises a device comprising a support; a layer configured to be placed in fluid-tight contact with the support, the layer defining a pattern of macro-orifices, each macro-orifice of the pattern of macro-orifices having walls and defining a macro-region when the second layer is placed in fluid-tight contact with the support such that the walls of the macro-orifice and the macro-region together define a macro-well; and a set of plugs, each of the plugs being configured for being received in a respective macro-well, each of the plugs comprising a lower membrane adapted to be placed in fluid-tight contact with the support when the layer is placed in fluid-tight contact with the support and the plug is received in a corresponding macro-well defined by the layer and the support, the lower membrane further defining a pattern of micro-orifices, wherein each micro-orifice has walls and defines a micro-region on the support when the plug is in fluid-tight contact with the support such that the walls of the micro-orifice and the micro-region together define a micro-well.

The present invention also provides a device for arraying biomolecules, including cells, comprising a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; a second layer configured to be placed in fluid-tight contact with the upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well; wherein the first layer and the second layer are configured for an arraying of biomolecules and/or cells on the support through the pattern of micro-orifices and the pattern of macro-orifices.

Preferably the first layer is configured to be placed in conformal contact with the support when the first layer is placed against the support and the second layer is configured to be placed in conformal contact with the support when the second layer is placed against the support. The support is made of a material selected from the group consisting of glass, silicon, fused silica, metal films, polystyrene, poly (methylacrylate) and polycarbonate. The first layer and the second layer are made of a material selected from the group consisting of glass, elastomers, rigid plastics, metals, silicon and silicon dioxide. The first layer and second layer is preferably made of an elastomer, and more preferably PDMS.

In the device preferably each macro-region encompasses at least one micro-region and more preferably each macro-region encompasses a plurality of micro-regions.

In the device, the walls of each macro-well may define a curve-in a cross-sectional plane perpendicular to the upper surface of the first layer.

Preferably, the device has at least one of the pattern of micro-orifices and the pattern of macro-orifices spatially and dimensionally corresponds to a standard microtiter plate. Further, the at least one of the pattern of micro-orifices and the pattern of macro-orifices spatially and dimensionally corresponds to a standard microtiter plate selected from a group consisting of a 6-well microtiter plate, a 12-well microtiter plate, a 24-well microtiter plate, a 96-well microtiter plate, a 384-well microtiter plate, a 1,536-well microtiter plate, and a 9,600-well microtiter plate.

In one embodiment, the device further comprises at least one cap for enclosing at least one of the macro-wells. Preferably the devices comprises a plurality of caps for enclosing each of the macro-wells.

The device may also comprise a means for aligning the micro-orifices with the macro-orifices. The means for aligning includes a guide mechanism on at least one of the support, the first layer and the second layer. The guide mechanism includes protrusions extending from the support, and guide orifices defined in the first layer and in the second layer for receiving the protrusions therein thereby aligning respective ones of the first layer and the second layer on the support. The means for aligning includes markings on at least one of the support, the first layer and the second layer.

The support has an upper surface that may have a coating thereon. The coating comprises a material selected from the group consisting of proteins, protein fragments, peptides, small molecules, lipid bilayers, metals and self-assembled monolayers.

The present invention further provides a device for arraying biomolecules and/or cells comprising a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; a second layer configured to be placed in fluid-tight contact with the support, the second layer defining a pattern of macro-orifices, each macro-orifice of the pattern of macro-orifices having walls and defining a macro-region when the second layer is placed in fluid-tight contact with the support such that the walls of the macro-orifice and the macro-region together define a macro-well;

wherein the first layer and the second layer are configured for an arraying of biomolecules and/or cells on the support through the pattern of micro-orifices and the pattern of macro-orifices.

The present invention also provides a device for arraying biomolecules and/or cells comprising a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; a second layer configured to be placed in fluid-tight contact with the support, the second layer comprising a plurality of rings, the rings defining a pattern of respective macro-orifices, each ring having walls and defining a macro-region when the second layer is placed in fluid-tight contact with the support such that the walls of the ring and the macro-region together define a macro-well; wherein the first layer and the second layer are configured for an arraying of biomolecules and/or cells on the support through the pattern of micro-orifices and the pattern of macro-orifices.

In another embodiment, a device for arraying biomolecules and/or cells comprises a support; a layer configured to be placed in fluid-tight contact with the support, the layer defining a pattern of macro-orifices, each macro-orifice of the pattern of macro-orifices having walls and defining a macro-region when the second layer is placed in fluid-tight contact with the support such that the walls of the macro-orifice and the macro-region together define a macro-well; a set of plugs, each of the plugs being configured for being received in a respective macro-well, each of the plugs comprising a lower membrane adapted to be placed in fluid-tight contact with the support when the layer is placed in fluid-tight contact with the support and the plug is received in a corresponding macro-well defined by the layer and the support, the lower membrane further defining a pattern of micro-orifices, wherein each micro-orifice has walls and defines a micro-region on the support when the plug is in fluid-tight contact with the support such that the walls of the micro-orifice and the micro-region together define a micro-well; wherein the first layer and the second layer are configured for an arraying of biomolecules and/or cells on the support through the pattern of micro-orifices and the pattern of macro-orifices.

The present invention further provides a method for arraying biomolecules and/or cells comprising the steps of positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; positioning a second layer to be in fluid-tight contact with an upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well; and immobilizing at least one biomolecule and/or cell of a plurality of biomolecules and/or cells in each respective micro-region on the support so as to situate the at least one biomolecule and/or cell within a corresponding micro-well, the biomolecules and/or cells thereby being arrayed on the support in a pattern that corresponds to the pattern of the micro-orifices.

In another embodiment, a coating is applied to an upper surface of the support. The coating may be cells, proteins, protein fragments, peptides, small molecules, lipid bilayers, metals and self-assembled monolayers.

The present invention further provides a method for arraying biomolecules and/or cells comprising: positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; immobilizing at least one biomolecule and/or cell of a plurality of biomolecules and/or cells in each respective micro-region on the support so as to situate the at least one biomolecule and/or cell within a corresponding micro-well, the biomolecules and/or cells thereby being arrayed on the support in a pattern that corresponds to the pattern of the micro-orifices; removing the first layer from the support after the step of immobilizing; and positioning a second layer to be in fluid-tight contact with the support, the second layer defining a pattern of macro-orifices, each macro-orifice of the pattern of macro-orifices having walls and defining a macro-region when the second layer is placed in fluid-tight contact with the support such that the walls of the macro-orifice and the macro-region together define a macro-well.

In an alternate embodiment, the method comprises positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; positioning a second layer to be in fluid-tight contact with the support, the second layer comprising a plurality of rings, the rings defining a pattern of respective macro-orifices, each ring having walls and defining a macro-region when the second layer is placed in fluid-tight contact with the support such that the walls of the ring and the macro-region together define a macro-well; and immobilizing at least one biomolecule and/or cell of a plurality of biomolecules and/or cells in each respective micro-region on the support so as to situate the at least one biomolecule and/or cell within a corresponding micro-well, the biomolecules and/or cells thereby being arrayed on the support in a pattern that corresponds to the pattern of the micro-orifices.

In yet another embodiment, a method of arraying biomolecules and/or cells comprises positioning a layer to be in fluid-tight contact with the support, the layer defining a pattern of macro-orifices, each macro-orifice of the pattern of macro-orifices having walls and defining a macro-region when the layer is placed in fluid-tight contact with the support such that the walls of the macro-orifice and the macro-region together define a macro-well; inserting each plug of a set of plugs in a respective macro-well, each of the plugs comprising a lower membrane placed in fluid-tight contact with the support when the layer is placed in fluid-tight contact with the support and the plug is received in a corresponding macro-well defined by the layer and the support, the lower membrane further defining a pattern of micro-orifices, wherein each micro-orifice has walls and defines a micro-region on the support when the plug is in fluid-tight contact with the support such that the walls of the micro-orifice and the micro-region together define a micro-well; and immobilizing a biomolecule and/or cell in at least one micro-region on the support so as to be situated within the micro-well, such that the biomolecule and/or cell is arrayed on the support in a pattern that corresponds to the first pattern of micro-orifices.

The present invention further provides a method of fabricating a device comprising: providing a support; providing a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; and providing a second layer configured to be placed in fluid-tight contact with the upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well.

In one embodiment, the method comprises: providing a mold; applying an elastomeric material in liquid form to a mold having a pattern of micro-posts corresponding to the pattern of micro-orifices; curing the elastomeric material; and removing the cured elastomeric material from the mold. The application includes spin-coating the elastomeric material. In an alternate embodiment, an adhesive adapted to be applied between the first layer and the second layer when the second layer is placed against the first layer is provided.

In yet another embodiment, a method of fabricating a device comprises: providing a first precursor layer (preferably an elastomer and more preferably PDMS); curing the first precursor layer to form a first layer, the first layer having an upper surface and defining a pattern of micro-orifices, each micro-orifice of the pattern of micro-orifices having walls and defining a micro-region in a plane defined by a lower surface of the first layer; placing a mold having a pattern of macro-posts on an upper surface of the first layer; providing a second precursor layer on the upper surface of the first layer; curing the second precursor layer to form a second layer, the second layer defining a pattern of macro-orifices, each macro-orifice of the pattern of macro-orifices having walls and defining a macro-region in a plane defined by a lower surface of the second layer.

Another embodiment further comprises placing the first layer against a support for establishing a fluid-tight contact of the first layer with the support, each micro-orifice of the pattern of micro-orifices having walls and defining the micro-region on the support when the first layer is placed in fluid-tight contact with the support such that the walls of said each micro-orifice and the micro-region on the support together define a micro-well, and each macro-orifice of the pattern of macro-orifices having walls and defining the macro-region such that the walls of said each macro-orifice and the macro-region together define a macro-well.

In yet another embodiment wherein providing a second precursor layer comprises providing the second precursor layer on the mold having the pattern of macro-posts such that a macro-orifice created by each macro-post encompasses at least one or more preferably a plurality of micro-regions.

In another embodiment, there is provided a method of fabricating a device, comprising: providing a first mold having a pattern of micro-posts; providing a second mold having a pattern of macro-posts; placing the second mold on the first mold; applying an elastomeric precursor in liquid form to the first mold and to the second mold after the step of placing so as to fill spaces around the micro-posts and the macro-posts with the elastomeric precursor; curing the elastomeric precursor after the step of applying for providing an elastomeric element; separating the elastomeric element from the first mold and from the second mold, wherein the pattern of micro-posts and the pattern of macro-posts are configured such that the micro-posts form a pattern of micro-orifices in the elastomeric element, and the macro-posts define a pattern of macro-orifices in the elastomeric element.

The present invention also provides for assays measuring cell movement. One embodiment, comprises: positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; positioning a second layer to be in fluid-tight contact with an upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well; each macro-region encompassing at least one micro-region; immobilizing at least one cell of a plurality of cells in each respective micro-region on the support so as to situate the at least one cell within a corresponding micro-well, the cells thereby being arrayed on the support in a pattern that corresponds to the pattern of the micro-orifices; allowing the cells to grow to confluency within the micro-regions; providing at least one of a plurality of test agents to at least one macro-well and allowing said test agent to contact confluent cells; removing said first and second layer; monitoring cells for movement or lack of movement away from said micro-regions; and correlating cellular movement or lack of movement away from said micro-regions with effect of said test agent on cellular movement.

Preferably each macro-region encompasses a plurality of micro-regions. A plurality of test agents can be provided into each macro-well.

The present invention also contemplates applying coating to an upper surface of the support before positioning said first layer. The coating is made of a material selected from the group consisting of proteins, protein fragments, peptides, small molecules, lipid bilayers, metals, self-assembled monolayers, cells, extracellular matrix proteins, hydrogels, and matrigel.

In yet another embodiment, an assay comprises positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; immobilizing at least one cell of a plurality of cells in each respective micro-region on the support so as to situate the at least one cell within a corresponding micro-well, the cells thereby being arrayed on the support in a pattern that corresponds to the pattern of the micro-orifices; allowing the cells to grow to confluency within the micro-regions; removing the first layer from the support after the step of immobilizing; positioning a second layer to be in fluid-tight contact with the support, the second layer defining a pattern of macro-orifices, each macro-orifice of the pattern of macro-orifices having walls and defining a macro-region when the second layer is placed in fluid-tight contact with the support such that the walls of the macro-orifice and the macro-region together define a macro-well; each macro-region encompassing at least one micro-region; providing at least one of a plurality of test agents to at least one macro-well and allowing said test agent to contact confluent cells; removing said second layer; monitoring cells for movement or lack of movement away from said micro-regions; correlating cellular movement or lack of movement away from said micro-regions with effect of said test agent on cellular movement.

Another embodiment comprises the steps of: positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; positioning a second layer to be in fluid-tight contact with the support, the second layer comprising a plurality of rings, the rings defining a pattern of respective macro-orifices, each ring having walls and defining a macro-region when the second layer is placed in fluid-tight contact with the support such that the walls of the ring and the macro-region together define a macro-well; each macro-region encompassing at least one micro-region; immobilizing at least one cell-of a plurality of cells in each respective micro-region on the support so as to situate the at least one cell within a corresponding micro-well, the cells thereby being arrayed on the support in a pattern that corresponds to the pattern of the micro-orifices, allowing the cells to grow to confluency within the micro-regions; providing at least one of a plurality of test agents to at least one macro-well and allowing said test agent to contact confluent cells; removing said first and second layer; monitoring cells for movement or lack of movement away from said micro-regions; and correlating cellular movement or lack of movement away from said micro-regions with effect of said test agent on cellular movement.

In an alternate embodiment, an assay for monitoring cell movement comprises the steps of: positioning a layer to be in fluid-tight contact with the support, the layer defining a pattern of macro-orifices, each macro-orifice of the pattern of macro-orifices having walls and defining a macro-region when the layer is placed in fluid-tight contact with the support such that the walls of the macro-orifice and the macro-region together define a macro-well; inserting each plug of a set of plugs in a respective macro-well, each of the plugs comprising a lower membrane placed in fluid-tight contact with the support when the layer is placed in fluid-tight contact with the support and the plug is received in a corresponding macro-well defined by the layer and the support, the lower membrane further defining a pattern of micro-orifices, wherein each micro-orifice has walls and defines a micro-region on the support when the plug is in fluid-tight contact with the support such that the walls of the micro-orifice and the micro-region together define a micro-well; immobilizing a cell in at least one micro-region on the support so as to be situated within the micro-well, such that the cell is arrayed on the support in a pattern that corresponds to the first pattern of micro-orifices; allowing the cells to grow to confluency within the micro-regions; providing at least one of a plurality of test agents to at least one macro-well and allowing said test agent to contact confluent cells; removing said layer containing said plugs; monitoring cells for movement or lack of movement away from said micro-regions; and correlating cellular movement or lack of movement away from said micro-regions with effect of said test agent on cellular movement.

The present invention also provides for a system for monitoring cell movement comprising: a) a device for arraying cells comprising a support; a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well; a second layer configured to be placed in fluid-tight contact with the upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well; wherein the first layer and the second layer are configured for an arraying of cells on the support through the pattern of micro-orifices and the pattern of macro-orifices; allowing the cells to grow to confluency within the micro-regions; providing at least one of a plurality of test agents to at least one macro-well and allowing said test agent to contact confluent cells; removing said first and second layer; monitoring cells for movement or lack of movement away from said micro-regions; and correlating cellular movement or lack of movement away from said micro-regions with effect of said test agent on cellular movement; b) an observation system configured to observe movement or lack of movement of arrayed cells; and c) a controller configured to link coordinates movement of the device for arraying cells into said observation system.

The observation system preferably comprises a phase contrast microscope or a flourescent image microscope. The controller further comprises a computer interface configured to coordinate the movement of the device into the observation system. The observation system further comprises a recording device configured to record images of the cells arrayed on the device for arraying cells. The recording device preferably comprises a digital camera configured to record images of the cells arrayed on the device for arraying cells, and wherein the recorded images are in a digital output. The computer interface is preferably configured to receive said digital output.

The present invention also provides for methods for monitoring and imaging cell growth. These methods involve positioning a first layer to be in fluid-tight contact with a support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well. Further, a second layer is positioned to be in fluid-tight contact with an upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well; each macro-region encompassing at least one micro-region.

At least one cell of a plurality of cells is immobilized in each respective micro-region on the support so as to situate the at least one cell within a corresponding micro-well, the cells thereby being arrayed on the support in a pattern that corresponds to the pattern of the micro-orifices.

The cells are allowed to grow to confluency within the micro-regions. At least one of a plurality of test agents is provided to at least one macro-well. The test agent is allowed to contact confluent cells. Thereafter the first and second layer is removed. The cells are then monitored for movement away from the micro-regions. The monitoring involves imaging the cells for at least two different time points to generate an image for each of the at least two different time points to generate at least two images, and calculating cellular movement from a comparison of the at least two images.

In yet other embodiments, cell growth and cell multiplication or proliferation is monitored and determined by a comparison of the at least two images.

Another embodiment of the present invention provides an image processing method comprising, from captured image data: a) creating a first histogram of image data signal strength along a first axis of the image data; b) identifying first coarse island locations from the first histogram; c)-marking interstitial boundaries on the first axis between the-first coarse island locations; d) creating a second histogram of image data signal strength along a second axis of the image data; e) identifying second coarse island locations from the second histogram; and f) marking second interstitial boundaries on the second axis between the second coarse island locations.

In another embodiment, the first and second coarse island locations are determined from maxima of the first and second histograms respectively. Alternatively, the first and second coarse island locations are determined from portions of the first and second histograms respectively that exceed a predetermined threshold value.

In another embodiment, the first and second interstitial boundaries are marked at midpoints between the first and second coarse island locations respectively. Another embodiment involves defining a plurality of island bounding boxes based on the first and second interstitial boundaries.

Another embodiment of an imaging processing method of the present invention comprises, from source image data representing imaged cellular material: for each pixel in a portion of the source image data; determining whether the source image data indicates the presence of cellular material in a region of a scanning circle; and if so, setting image data for a co-located, similarly dimensioned scanning circle in second image data; and thereafter, identifying objects based on the second image data. Further, a bounding box for each object identified in the image data may be defined.

BRIEF DESCRIPTION OF THE DRAWINGS

The present invention is illustrated by way of example and not limitation in the figures in the accompanying drawings, in which like references indicate similar elements.

FIG. 3(a) is a top view of a support for a qualitative cell migration system, in accordance with one embodiment of the present invention.

FIG. 3(b) is a side view of the support shown in FIG. 3(a).

FIG. 4(a) is a top view of a first layer for a qualitative cell migration system, in accordance with one embodiment of the present invention.

FIG. 4(b) is a side view of the first layer shown in FIG. 4(a).

FIG. 5(a) is a top view of a second layer for a qualitative cell migration system, in accordance with one embodiment of the present invention.

FIG. 5(b) is a side view of the second layer shown in FIG. 5(a).

FIG. 13(a) illustrates a second layer positioned on a first layer, in accordance with another embodiment of the present invention.

FIG. 13(b) illustrates the first and second layers shown in FIG. 13(a) having cells patterned therethrough onto a support.

FIG. 13(c) illustrates the first layer shown in FIG. 13(b) being removed such that the cells arrayed on the support shown in FIG. 13(b) are permitted to migrate.

FIG. 13(d) illustrates cells that have been patterned through the first and second layers shown in FIG. 13(b) onto a support and that have grown to confluence.

FIG. 13(e) shows the cells having migrated upon the removal of the first and second layers, as shown in FIG. 13(c).

FIG. 25D depicts enzyme inhibition screens in a cell based context.

FIG. 26 shows that cell migration may be affected by the support upon which the cells are placed. It also depicts the use of fibronectin on the support as a cytophilic substance to encourage adherence of cells to the support.

DETAILED DESCRIPTION

Figure 1A:
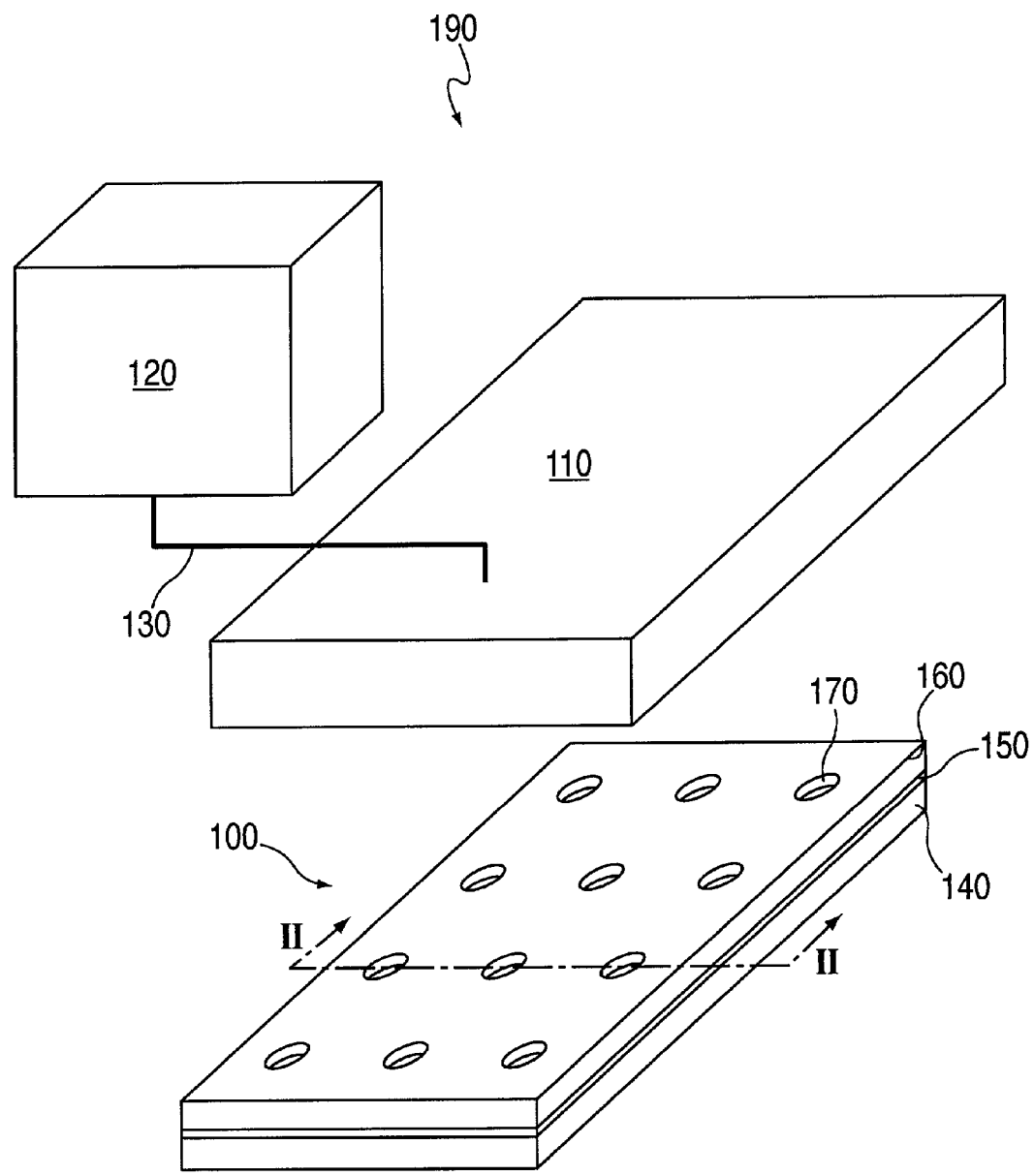
FIG. 1(a) is a perspective view of a qualitative cell migration system, in accordance with an example embodiment of the present invention.

FIG. 1(a) is a schematic, perspective view of a qualitative cell migration system 190 in accordance with an embodiment of the present invention. The qualitative cell migration system 190 includes a qualitative cell migration assay plate 100, an observation system 110, and a controller 120. The controller 120 in this embodiment is in signal communication with the observation system 110 via line 130. The controller 120 and the observation system 110 may be positioned and programmed to observe, record, and analyze the migration, movement, and behavior of cells that are placed in or on the qualitative cell migration assay plate 100, as readily recognizable by a person skilled in the art.

The present invention provides a cell migration assay plate 100 for the quantification of the qualitative cell patterning and migration. Embodiments of the assay plate, according to the present invention, allow a patterning of cells in a discrete, predetermined array. The present invention also provides cell migration/motility assays, also referred to as "CMAs," which preferably uses a qualitative cell migration assay plate according to the present invention to pattern cells into discrete arrays and uses a cell migration system according to the present invention to monitor and record the results of the assays. Embodiments of the cell migration assay plate, the cell migration system, and the cell migration/motility assays of the present invention are compatible with the demands of high-throughput screening, and represent a significant advance in both throughput and ease of use. Generally, with embodiments of the qualitative cell migration assay plate of the invention, cells are patterned into a specific geometry, treated with various cell affecting agents, and allowed to migrate or otherwise react in response to a cell affecting agent.

Figure 1B:
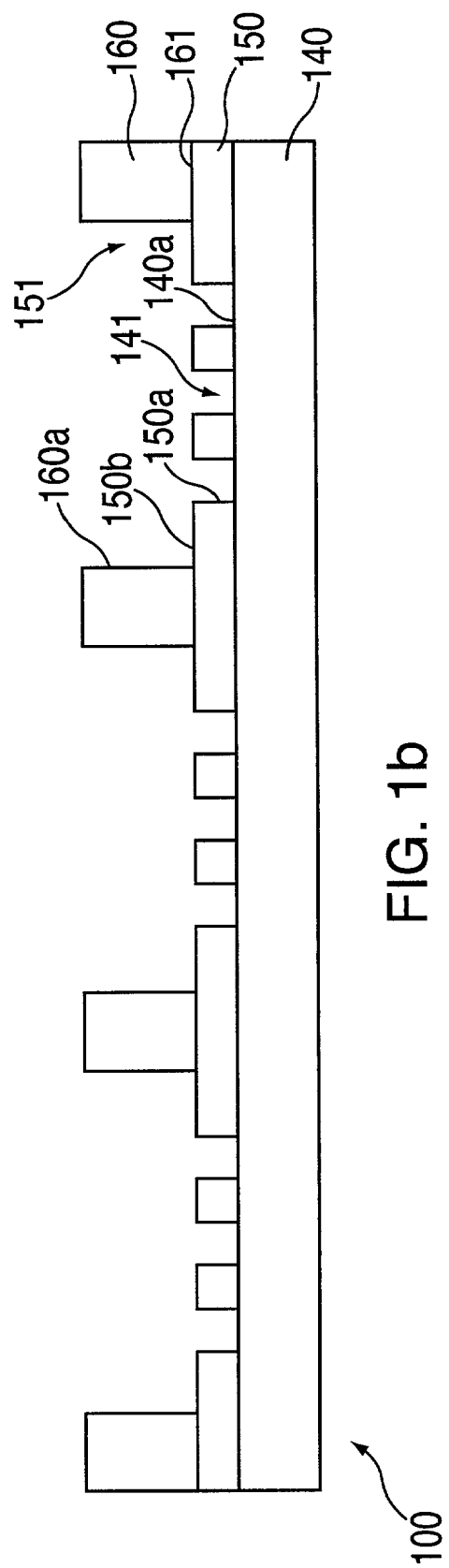
FIG. 1(b) is a cross-sectional view of the qualitative cell migration assay plate shown in FIG. 1(a), taken along the lines II—II.

FIG. 1(b) is a cross-sectional view of cell migration assay plate 100 of FIG. 1(a), taken along lines II—II. Embodiments of the cell migration assay plate according to the present invention, as shown by way of example in the embodiments of FIGS. 1(a) and 1(b), include: a support 140 onto which cells may be arrayed, a first layer 150 that provides a pattern through which cells may be arrayed on the support 140; and a second layer 160. The support 140 provides a base upon which cells can be patterned, attached, or reversibly or irreversibly immobilized. The support 140 has an upper surface 140a. The first layer 150 defines a plurality of orifices 300 therethrough, referred to hereinafter as "micro-orifices 300." The micro-orifices 300 are arranged in a pattern or array that defines positions in which cells may be deposited, attached, or reversibly or irreversibly immobilized to the upper surface 140a of the support 140. The micro-orifices 300 have walls 150a that define the micro-orifices 300. The second layer 160 defines a plurality of orifices 170 therethrough, referred to hereinafter as "macro-orifices 170." The macro-orifices 170 are arranged in a pattern or array through which test agents or solutions are deposited to contact cells that were previously deposited, attached, or reversibly or irreversibly immobilized to the upper surface 140a of the support 140. The macro-orifices 170 have walls 160a that define the macro-orifices 170.

The size of the support 140 preferably matches the dimensions of an industry standard micro-titer plate. For example, FIGS. 3(a) and 3(b) illustrate the support 140, according to one embodiment of the present invention. More specifically, FIG. 3(a) is a plan view that illustrates the support 140 having a length dimension L and a width dimension W. According to one embodiment, the length dimension L of the support 140 is approximately 3 inches (75 mm), while the width dimension W is approximately 5 inches (125 mm). Preferably, all of the layers of the cell migration assay plate 100 would have corresponding outer dimensions and would be amenable to use in standard laboratory platforms such as microtiter plate readers, automatic handlers, and fluid delivery systems.

Referring to the embodiment illustrated in FIG. 1(b), the micro-orifices 300 extend through the entire thickness of the first layer 150. In a preferred embodiment of the present invention, the first layer 150 defines an array of micro-orifices 300, which are disposed in an array of discrete first positions. In addition, the first layer 150 is preferably capable of making conformal contact, that is, a form-fitting fluid-tight contact, with support 140, when brought into contact with the support 140. Furthermore, the first layer 150 is preferably capable of self-sealing to the support 140, e.g., creating a seal with the support 140 without the use of a sealing agent. When the first layer 150 is brought into contact with the support 140 to create a fluid-tight seal, a plurality of wells, referred to hereinafter as "micro-wells," are formed. The walls of each micro-well 141 are defined by the walls 150a of the micro-orifices 300 in the first layer 150, while the bottom of each micro-well 141 is defined by an exposed region on the upper surface 140a of the support 140. Advantageously, each micro-well 141 is individually fluidically addressable, e.g., may have a different fluid introduced therein.

The first layer 150 may be comprised of materials commonly used in biological sciences, such as glass, elastomers (e.g., PDMS), rigid plastics (e.g., polyethylene, polypropylene, polystyrene, polycarbonate, PMMA), metals, silicon, silicon dioxide and other rigid supports.

According to one embodiment of the present invention, the first layer 150 maybe treated, conditioned or coated with a substance that resists cell attachment so that when the first layer 150 is lifted from the support, the risk of damaging cells is reduced. Coatings resistant to proteins are known in the art and include, but are not limited to: bovine serum albumin (BSA), gelatin, lysozyme, octoxynol, polysorbate 20 (polyoxyethylenesorbitan monolaurate), and polyethylene oxide-containing block copolymer surfactants. Conversely, according to other embodiments of the present invention, the first layer 150 is not so coated, such that when the first layer 150 is removed, the cells that have adhered to the first layer 150 will likely be damaged as the first layer 150 is peeled away from the support. By damaging cells, phenomena, such as wound healing, may be observed.

FIG. 4(a) illustrates the first layer 150 defining a plurality of micro-orifices 300 disposed therethrough. In the embodiment shown, the micro-orifices 300 are grouped into discrete areas. These discrete areas may have a variety of shapes and sizes. In the embodiment shown, each area has a cluster of micro-orifices 300 arranged in a circular arrangement. It is understood that the micro-orifices 300 of the first layer 150 may have any other arrangement that would be within the knowledge of a person skilled in the art, such as, for example, a rectangular, hexagonal, circular or any another arrangement.

The diameter of the micro-orifices 300 (and also the diameter of the micro-wells 141 that are defined by the walls 150a of the micro-orifices), shown as dimension "d" in FIG. 4(a), may be varied according to cell types and the desired number of cells to be placed into each micro-well 141. For example, if the diameter of the micro-well 141 and the cell to be placed in the micro-well 141 are both 10 mm, only one cell will be depositable through each micro-orifice 300 and into each micro-well 141. Thus, in this example, if the diameter of the micro-orifice 300 is 100 mm, up to approximately 100 cells may be deposited in a micro-well 141 defined by that micro-orifice 300.

According to embodiments of the present invention, the diameter d of micro-wells 141 varies from about 1 mm to about 500 mm, and is preferably from about 40 mm to about 200 mm. In most cases, the diameter d is greater than the diameter of cells used in experiments, but in specialized assays, the diameter d may be smaller than that of the cells. For example, if it is desired to pattern a single cell through each micro-orifice 300 of the first layer 150 and into micro-well 141, the diameter d may range from about 1 microns to about 20 microns. In a typical chemotaxis assay, the diameter d is preferably approximately 0.3–0.8 times the diameter of cells. Furthermore, the distance between adjacent micro-orifices 300 (and thus the distance between adjacent micro-wells 141 defined by the micro-orifices 300) may be varied. This distance is identified as dimension "p" in FIG. 4(*a*). Although any distance p may be employed, this distance p may vary, according to various example embodiments of the present invention, from about the same distance as the diameter dimension d to about 10 times the diameter d.

The second layer 160 is comprised of materials commonly used in biological sciences, such as glass, elastomers (e.g., PDMS), rigid plastics (e.g., polyethylene, polypropylene, polystyrene, polycarbonate, PMMA), metals, silicon, silicon dioxide and other rigid supports. A preferred material is PDMS, and a more preferred material is a combination of PDMS and a rigid plastic such as polycarbonate.

Referring to the embodiment illustrated in FIG. 1(*b*), the macro-orifices 170 extend through the entire thickness of the second layer 160. In a preferred embodiment of the present invention, the second layer 160 has an array of macro-orifices 170. In addition, the second layer 160 is preferably capable of making conformal contact, that is, a form-fitting, fluid tight contact when brought into contact with either an upper surface 150*b* of the first layer 150, or the upper surface 140*a* of the support 140. Furthermore, the second layer 160 is preferably capable of self-sealing to either of upper surface 150*b* or upper surface 140*a*, e.g., creating a conformal, fluid-tight seal therewith without the use of a sealing agent. In the embodiment of the present invention shown in FIG. 1(*b*), when the second layer 160 is brought into contact with the upper surface 150*b* of the first layer 150 to create a fluid-tight seal, a plurality of wells 151, referred to hereinafter as "macro-wells 151," are formed. The walls of each macro-well 151 are defined by the walls 160*a* of the macro-orifices 170 in the second layer 160. The bottom of each macro-well 151 is the exposed region defined by the size and shape of the macro-orifice 151 at the lower surface 161 of the second layer 160. For instance, in the embodiment illustrated in FIG. 1(*b*), the bottom of the macro-well 151 is the exposed region defined by a portion of the upper surface 140*a* of the support 140, the walls 150*a* of the micro-orifices 300 that are encompassed by the macro-well 151, and by the exposed regions of the upper surface 150*b* of the first layer 150 within the encompassed micro-wells 300. Thus, as should be evident, the elements that make up the bottom of the macro-wells 151 depend on the size and orientation of the macro-wells 151 relative to the micro-wells 141. Advantageously, each micro-well 141 is individually fluidically addressable, e.g., may have a different fluid introduced therein. It is also noted that, in accordance with an alternate embodiment of the present invention, the first layer 150 is removed from the support 140 after arraying the cells through the micro-orifices 300, and the second layer 160 is brought into contact with the upper surface 140*a* of the support 140. In this case, the bottom of the macro-well 151 is an exposed region of the upper surface 140*a* of the support 140, and may encompass cells or groups of cells that were previously arrayed onto the upper surface 140*a* of the support 140.

The macro-wells 151 defined by the macro-orifices 170 may encompass discrete regions of the first layer 150 such that fluids added to one macro-orifice 170 will flow to the encompassed micro-wells 141, but may not flow to adjacent or other micro-wells 141 not encompassed by the macro-well 151. In this embodiment, the macro-wells 151 allow for easy addition and removal of solutions, while the first layer 150 of micro-orifices 300 provides the spatial patterning of the cells.

As previously mentioned, the micro-orifices 300 may be sized to accommodate the passage of several cells at a time, the passage of a single cell at a time, or the passage of a portion of a cell. The size of the micro-orifices 300 may be selected to accommodate the particular cell and stimulus being studied. Depending on the size and orientation of the micro-orifices 300, cells can be placed in specific regions, groups or patterns on the support layer 140. In so doing, the starting point of each cell or cell group can be readily identified and its distance of travel readily measured and timed for various time periods. Preferably, more than one cell will settle through each orifice.

FIG. 5 illustrates the second layer 160 having a plurality of macro-orifices 170 defined therethrough. In the embodiment shown, the macro-orifices 170 are circular in a top plan view thereof, although it is understood that the macro-orifices 170 may have a variety of shapes and sizes. The number of macro-wells 151, the diameter of the macro-orifices 170 (and also the diameter of the macro-wells 151 that are defined by the walls 160*a* of the micro-orifices 170), shown as dimension "d" in FIG. 5, and the distance between adjacent macro-wells 151, shown as dimension "p" in FIG. 5, may each be varied according to cell types and the number of micro-wells 141 desired to be encompassed in each macro-well 151, or the process desired-to be performed. Preferably the arrangement of the macro-orifices 300, and thus the arrangement of the macro-wells 151 defined thereby, corresponds to the footprint of standard 24-, 96-, 384-, and 1536-well micro-titer plates. For example, the typical dimensions of various standard micro-titer plates ("ID" refers to the inner diameter of a well of the micro-titer plate, while "p" refers to the distance between adjacent wells) are as follows:

| Device | ID (mm) | p (mm) |
|---|---|---|
| 24 well | 9–15 | 18 |
| 96 well | 6 | 9 |
| 384 well | 3 | 4.5 |
| 1536 well | 1.5 | 2.25 |

In one embodiment of the present invention, the second layer 160 is comprised of an elastomer, such as PDMS. In this embodiment, the macro-orifices 170 are formed in the second layer 160 in a manner that is similar to the manner in which the micro-orifices 300 are formed in the first layer 150, e.g., precursor PDMS is spin cast on to a master having posts corresponding in size (diameter and length) and pitch as the desired macro-orifices. In another embodiment, the second layer 160 is comprised of a rigid material including, but not limited to, glass, rigid plastics or metals. The macro-orifices 170 are formed in these materials by methods known in the art, such as molding, etching, and punching.

In various other embodiments of the present invention, macro-orifices 170 of the second layer 160 may comprise individual rings or interconnected rings. For instance, in one embodiment, the second layer 160 comprises rings made of a rigid plastic such as polypropylene, and having a diameter equal to the desired diameter of the macro-orifices 170. The rigid rings may be molded together with an elastomer such as PDMS to form the second layer 160.

The thickness or height of the first layer 150, which is shown in FIG. 4(*b*) and which is designated as "2 h," may be predetermined so as to accommodate a desired number of cells, e.g., a single cell or multiple cells. In other words, the thickness of the first layer 150 dictates the maximum depth of the micro-wells 141 formed by the micro-orifices 300. To alter the thickness of the first layer 150, one may stack identical first layer 150s on top of each other to achieve the desired thickness. In alternate embodiments, the first layer 150 may be fabricated so as to have a desired thickness. Because elastomers such as PDMS create a conformal contact that is reversible, stacking of the layers allows one to achieve a micro-orifice of a desired depth. By "reversible," what is meant in the context of the present invention, is a conformal contact that can be undone without compromising a structural integrity of the component making the conformal contact.

The thickness or height of the support 140, shown in FIG. 3(b) and designated as "h," may be chosen as desired. Similarly, the thickness or height of the second layer 160, as shown in FIG. 5(b) and designated as "h," may be chosen to accommodate a desired amount of solution to be added into the macro-wells 151 formed by the macro-orifices 170. A preferred height "h" of the second layer 160 ranges from about 2 mm to about 12 mm.

The support 140 on which the cells may be placed or patterned comprises a material that is compatible with the cells. Suitable materials may include standard materials used in cell biology, such as glass, ceramics, metals, polystyrene, polycarbonate, polypropylene, as well as other plastics including polymeric thin films, and polymethyl methacrylate (PMMA). Preferably, the material provides sufficient rigidity to allow the device to be handled either manually or by automatic laboratory handlers. A preferred material is optical grade polycarbonate with a thickness of about 0.2 to 2 mm, as this may allow the viewing of the patterned cells with optical microscopy techniques.

Additionally, the support 140 may be comprised of any material that provides a conformal contact with additional layers of the cell migration assay plate 100. Materials which allow conformal contact are known in the art and include elastomers with a preferred elastomer being polydimethyl-siloxane ("PDMS"). In an alternate embodiment, the support 140 and/or the first layer 150 are comprised of an elastomer. Elastomers such as PDMS are preferred in that the conformal contact prevents fluids from infiltrating other orifices in the first layer 150 or the second layer 160. In other embodiments, sealing agents or mechanical sealing devices such as clamps and gaskets may also be used to create or enhance the seal between the support 140 and the first layer 150 or between the first layer 150 and the second layer 160. Sealing agents capable of creating fluid-tight seals between two materials are known in the art and include glues, inert gels, and swellable resins.

Figure 2A:
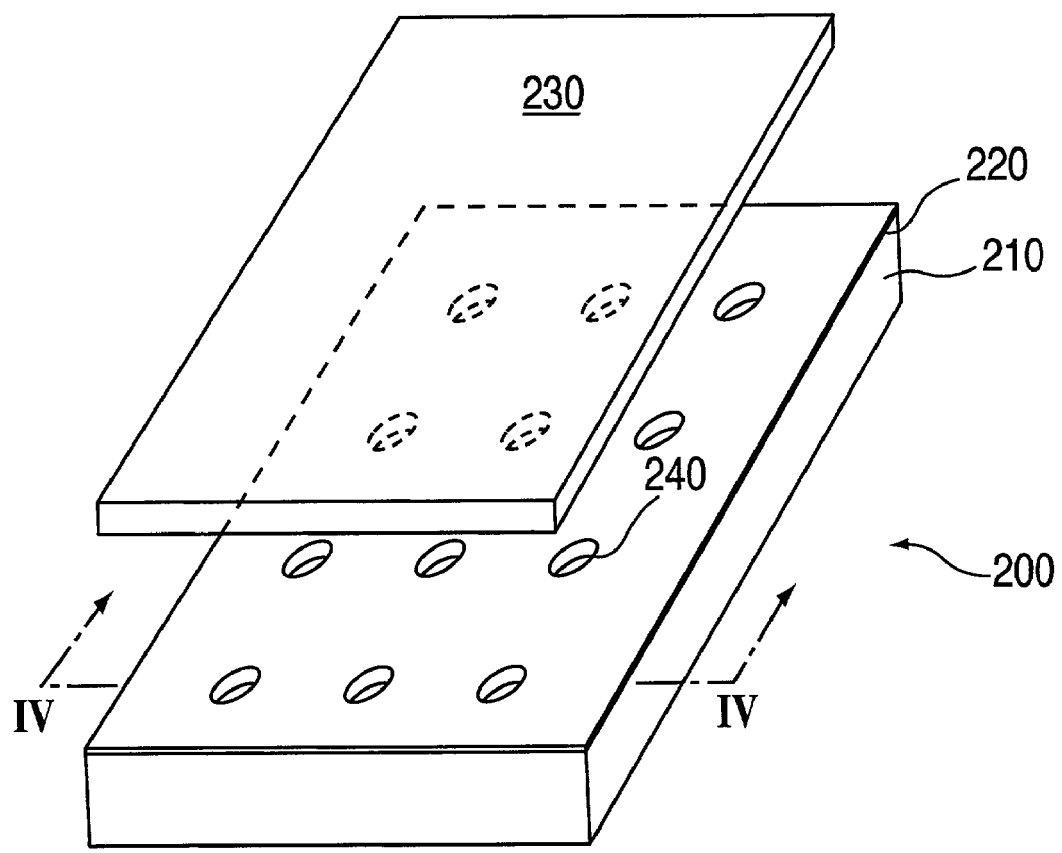
FIG. 2(a) is a perspective view of a qualitative cell migration system, in accordance with an example embodiment of the present invention.
Figure 2B:
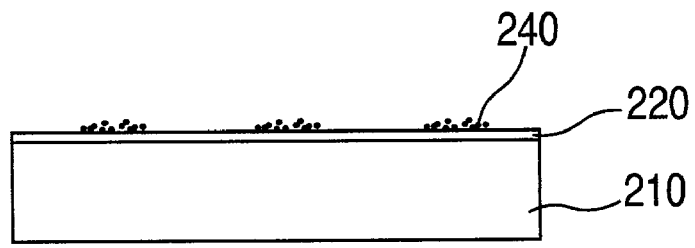
FIG. 2(b) is a cross-sectional view of the qualitative cell migration assay plate shown in FIG. 2(a), taken along the lines IV—IV.

FIG. 2(a) illustrates one embodiment wherein support 210 is treated with a coating 220. A cross-sectional view of the embodiment shown in FIG. 2(a), taken along the lines II—II, is shown in FIG. 2(b). Alternatively, support 210 may be overlayed with a membrane having a desired treatment or coating 220 thereon.

Coating 220 may be made of any substance that achieves a desired effect on the cells to be arrayed or may be made of any substance to assist in the arraying of the cells or it may comprise a bio-inert coating. Coating 220 may also comprise proteins, proteins fragments, peptides, small molecules, lipid bilayers, metals, or self-assembled monolayers. Self-assembled monolayers are the most widely studied and best developed examples of nonbiological, self-assembling systems. They form spontaneously by chemisorption and self-organization of functionalized, long-chain organic molecules onto the surfaces of appropriate substrates. Self-assembled monolayers are usually prepared by immersing a substrate in the solution containing a ligand that is reactive toward the surface, or by exposing the substrate to the vapor of the reactive species. There are many systems known in the art to produce self-assembled monolayers.

The best characterized systems of self-assembled monolayers are alkanethiolates $CH_3(CH_2)_nS-$ on gold. Alkanethiols chemisorb spontaneously on a gold surface from solution and form adsorbed alkanethiolates. Sulfur atoms bonded to the gold surface bring the alkyl chains in close contact—these contacts freeze out configurational entropy and lead to an ordered structure. For carbon chains of up to approximately 20 atoms, the degree of interaction in a self-assembled monolayer increases with the density of molecules on the surface and the length of the alkyl backbones. Only alkanethiolates with $n>11$ form the closely packed and essentially two-dimensional organic quasi-crystals supported on gold that characterize the self-assembled monolayers most useful in soft lithography. The formation of ordered self-assembled monolayers on gold from alkanethiols is a relatively fast-process. Highly ordered self-assembled monolayers of hexanedecanethiolate on gold can be prepared by immersing a gold substrate in a solution of hexadecanethiold in ethanol (ca. 2 mM) for several minutes, and formation of self-assembled monolayers during microcontact printing may occur in seconds.

It may be desirable to pattern the self-assembled monolayer to have an arrayed surface. For example, it may be desirable to pattern the self-assembled monolayer such that it has an array matching the array of micro-orifices or macro-orifices or any other array. Patterning self-assembled monolayers in the plane of the surface has been achieved by a wide variety of techniques, including micro-contact printing, photo-oxidation, photo-cross-linking, photo-activation, photolithography/plating, electron beam writing, focused ion beam writing, neutral metastable atom writing, SPM lithography, micro-machining, micro-pen writing. A preferred method is micro-contact printing. Micro-contact printing is described, by way of example, in U.S. Pat. No. 5,776,748, which is herein incorporated by reference in its entirety.

In another embodiment, coating 220 comprising self-assembled monolayers is "patterned" by micro-contact printing. The self-assembled monolayer patterns are applied to the support using a stamp in a "printing" process in which the "ink" consists of a solution including a compound capable of chemisorbing to form a self-assembled monolayer. The ink is applied to the surface of a plate using the stamp and deposits a self-assembled monolayer on the support in a pattern determined by the pattern on the stamp. The support may be stamped repeatedly with the same or different stamps in various orientations and with the same or different self-assembled monolayer-forming solutions. In addition, after stamping, the portions of the support which remain bare or uncovered by a self-assembled monolayer may be derivatized. Such derivatization may conveniently include exposure to another solution including a self-assembled monolayer-forming compound. The self-assembled monolayer-forming or derivatizing solutions are chosen such that the regions of the finished support defined by the patterns differ from each other in their ability to bind biological materials. Thus, for example, a grid pattern may be created in which the square regions of the grid are cytophilic and bind cells but the linear regions of the grid are cytophobic and no cells bind to these regions.

A simple illustration of the general process of microcontact printing is provided by way of example below. A polymeric material is cast onto a mold with raised features defining a pattern to form a stamp. The stamp with the stamping surface after curing is separated from the mold. The stamp is inked with a desired "ink," which includes a self-assembled monolayer-forming compound. The "inked" stamp is brought into contact with a plate comprising a substrate and optionally, coated with a thin coating of surface material. The self-assembled monolayer forming compound of the ink chemisorbs to the material surface to form a self-assembled monolayer with surface regions in a pattern corresponding to the stamping surface of the stamp. The plate can then be exposed to a second or filling solution including a self-assembled monolayer-forming compound. The second solution has filled the bare regions of the surface material with a second or filling self-assembled monolayer. The plate having the patterned self-assembled monolayer can then have a material selectively bound to the surface regions of the first self-assembled monolayer but not bound the surface regions of the second self-assembled monolayer and vice-versa.

The stamp is inked with a solution capable of forming a self-assembled monolayer by chemisorption to a surface. The inking may, for example, be accomplished by: (1) contacting the stamp with a piece of lint-free paper moistened with the ink; (2) pouring the ink directly onto the stamp or; (3) applying the ink to the stamp with a cotton swab. The ink is then allowed to dry on the stamp or is blown dry so that no ink in liquid form, which may cause blurring, remains on the stamp. The self-assembled monolayer-forming compound may be very rapidly transferred to the stamping surface. For example, contacting the stamping surface with the compound for a period of time of approximately two seconds is generally adequate to effect sufficient transfer, or contact may be maintained for substantially longer periods of time. The self-assembled monolayer-forming compound may be dissolved in a solvent for such transfer, and this is often advantageous in the present invention. Any organic solvent within which the compound dissolves may be employed but, preferably, one is chosen which aids in the absorption of the self-assembled monolayer-forming compound by the stamping surface. Thus, for example, ethanol, THF, acetone, diethyl ether, toluene, isooctane and the like may be employed. For use with a PDMS stamp, ethanol is particularly preferred, and toluene and isooctane and not preferred as they are not well absorbed. The concentration of the self-assembled monolayer-forming compound in the ink solution may be as low as 1 µM. A concentration of 1–10 mM is preferred and concentrations above 100 mM are not recommended.

The support is then contacted with the stamp such that the inked stamping surface bearing the pattern contacts the surface material of the plate. This may be accomplished by hand with the application of slight finger pressure or by a mechanical device. The stamp and plate need not be held in contact for an extended period; contact times between 1 second and 1 hour result in apparently identical patterns for hexadecanethiol (1–10 mM in ethanol) ink applied to a plate with a gold surface. During contact, the self-assembled monolayer-forming compound of the ink reacts with the surface of the plate such that, when the stamp is gently removed, a self-assembled monolayer is chemisorbed to the plate in a pattern corresponding to the stamp.

A variety of compounds may be used in solution as the ink and a variety of materials may provide the surface material onto which the ink is stamped and the self-assembled monolayer is formed. In general, the choice of ink will depend on the surface material to be stamped. In general, the surface material and self-assembled monolayer-forming compound are selected such that the self-assembled monolayer-forming compound terminates at a first end in a functional group that binds or chemisorbs to the surface of the surface material. As used herein, the terminology "end" of a compound is meant to include both the physical terminus of a molecule as well as any portion of a molecule available for forming a bond with the surface in a way that the compound can form a self-assembled monolayer. The compound may comprise a molecule having first and second terminal ends, separated by a spacer portion, the first terminal end comprising a first functional group selected to bond to the surface material of the plate, and the second terminal end optionally including a second functional group selected to provide a self-assembled monolayer on the material surface having a desirable exposed functionality. The spacer portion of the molecule may be selected to provide a particular thickness of the resultant self-assembled monolayer, as well as to facilitate self-assembled monolayer formation. Although self-assembled monolayers of the present invention may vary in thickness, as described below, self-assembled monolayers having a thickness of less than about 50 Angstroms are generally preferred, more preferably those having a thickness of less than about 30 Angstroms and more preferably those having a thickness of less than about 15 Angstroms. These dimensions are generally a function of the selection of the compound and in particular the spacer portion thereof.

A wide variety of surface materials and self-assembled monolayer-forming compounds are suitable for use in the present invention. A non-limiting exemplary list of combinations of surface materials and functional groups which will bind to those surface materials follows. Although the following list categorizes certain preferred materials with certain preferred functional groups which firmly bind thereto, many of the following functional groups would be suitable for use with exemplary materials with which they are not categorized, and any and all such combinations are within the scope of the present invention. Preferred materials for use as the surface material include metals such as gold, silver, copper, cadmium, zinc, palladium, platinum, mercury, lead, iron, chromium, manganese, tungsten, and any alloys of the above when employed with sulfur-containing functional groups such as thiols, sulfides, disulfides, and the like; doped or undoped silicon employed with silanes and chlorosilanes; metal oxides such as silica, alumina, quartz, glass, and the like employed with carboxylic acids; platinum and palladium employed with nitrites and isonitriles; and copper employed with hydroxamic acids. Additional suitable functional groups include acid chlorides, anhydrides, sulfonyl groups, phosphoryl groups, hydroxyl groups and amino acid groups. Additional surface materials include germanium, gallium, arsenic, and gallium arsenide. Additionally, epoxy compounds, polysulfone compounds, plastics and other polymers may find use as the surface material in the present invention. Polymers used to form bioerodable articles, including but not limited to polyanhydrides, and polylactic and polyglycolic acids, are also suitable. Additional materials and functional groups suitable for use in the present invention can be found in U.S. Pat. No. 5,079,600, issued Jan. 7, 1992, which is incorporated herein in its entirety by reference.

According to a particularly preferred embodiment of the present invention, a combination of gold as the surface material and a self-assembled monolayer-forming compound having at least one sulfur-containing functional group such as a thiol, sulfide, or disulfide is selected.

The self-assembled monolayer-forming compound may terminate in a second end or "head group," opposite to the end bearing the functional group selected to bind to the surface material, with any of a variety of functionalities. That is, the compound may include a functionality that, when the compound forms a self-assembled monolayer on the surface material, is exposed. Such a functionality may be selected to create a self-assembled monolayer that is hydrophobic, hydrophilic, that selectively binds various biological or other chemical species, or the like. For example, ionic, nonionic, polar, nonpolar, halogenated, alkyl, aryl or other functionalities may exist at the exposed portion of the compound. A non-limiting, exemplary list of such functional groups includes those described above with respect to the functional group for attachment to the surface material in addition to: —OH, —CONH—, —CONHCO—, —NH$_2$, —NH—, —COOH, —COOR, —CSNH—, —NO$_2^-$, —SO$_2$, —RCOR—, —RCSR—, —RSR, —ROR—, —PO$_4^{-3}$, —OSO$_3^{-2}$, —SO$_3^-$, —NH$_x$R$_4$–x$^+$, —COO$^-$, —SOO$^-$, —RSOR—, —CONR$_2$, —(OCH$^2$ CH$_2$)$_n$ (where n=1–20, preferably 1–8), —CH$_3$, —PO$_3$H, -2-imidazole, —N(CH$_3$)$_2$, —NR$_2$, —PO$_3$H$_2$, —CN, —(CF$_2$)$_n$ CF$_3$ (where n=1–20, preferably 1–8), olefins, and the like. In the above list, R is hydrogen or an organic group such as a hydrocarbon or fluorinated hydrocarbon. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups.

In addition, the functional group may be chosen from a wide variety of compounds or fragments thereof which will render the self-assembled monolayer generally or specifically "biophilic" as those terms are defined below. Generally biophilic functional groups are those that would generally promote the binding, adherence, or adsorption of biological materials such as, for example, intact cells, fractionated cells, cellular organelles, proteins, lipids, polysaccharides, simple carbohydrates, complex carbohydrates, and/or nucleic acids. Generally biophilic functional groups include hydrophobic groups or alkyl groups with charged moieties such as —COO$^-$, —PO$_3$ H$^-$ or 2-imidazolo groups, and compounds or fragments of compounds such as extracellular matrix proteins, fibronectin, collagen, laminin, serum albumin, polygalactose, sialic acid, and various lectin binding sugars. Specifically biophilic functional groups are those that selectively or preferentially bind, adhere or adsorb a specific type or types of biological material so as, for example, to identify or isolate the specific material from a mixture of materials. Specific biophilic materials include antibodies or fragments of antibodies and their antigens, cell surface receptors and their ligands, nucleic acid sequences and many others that are known to those of ordinary skill in the art. The choice of an appropriate biophilic functional group depends on considerations of the biological material sought to be bound, the affinity of the binding required, availability, facility of ease, effect on the ability of the Self-assembled monolayer-forming compound to effectively form a Self-assembled monolayer, and cost. Such a choice is within the knowledge, ability and discretion of one of ordinary skill in the art.

Alternatively, the functional group may be chosen from a wide variety of compounds or fragments thereof which will render the self-assembled monolayer "biophobic" as that term is defined below. Biophobic self-assembled monolayers are those with a generally low affinity for binding, adhering, or adsorbing biological materials such as, for example, intact cells, fractionated cells, cellular organelles, proteins, lipids, polysaccharides, simple carbohydrates, complex carbohydrates, and/or nucleic acids. Biophobic functional groups include polar but uncharged groups including unsaturated hydrocarbons. A particularly preferred biophobic functional group is polyethylene glycol (PEG).

The central portion of the molecules comprising the self-assembled monolayer-forming compound generally includes a spacer functionality connecting the functional group selected to bind the to surface material and the exposed functionality. Alternately, the spacer may essentially comprise the exposed functionality, if no particular functional group is selected other than the spacer. Any spacer that does not disrupt self-assembled monolayer packing and that allows the self-assembled monolayer layer to be somewhat impermeable to various reagents such as etching reagents, as described below, in addition to organic or aqueous environments, is suitable. The spacer may be polar; non-polar; halogenated or, in particular, fluorinated; positively charged; negatively charged; or uncharged. For example, a saturated or unsaturated, linear or branched alkyl, aryl, or other hydrocarbon spacer may be used.

A variety of lengths of the self-assembled monolayer-forming compound maybe employed in the present invention. If two or more different self-assembled monolayer-forming compounds are used in one stamping step, for example if two or more different self-assembled monolayer-forming compounds are used in the ink, it is often advantageous that these species have similar lengths. However, when a two or more step process is used in which a first self-assembled monolayer is provided on a surface and at least a second self-assembled monolayer is provided on the surface, the various self-assembled monolayers being continuous or noncontinuous, it may be advantageous in some circumstances to select molecular species for formation of the various self-assembled monolayers that have different lengths. For example, if the self-assembled monolayer formed by stamping has a first molecular length and the self-assembled monolayer subsequently derivatized to the surface has a second molecular length greater than that of the stamped self-assembled monolayer, a continuous self-assembled monolayer having a plurality of "wells" results. These wells are the result of the stamped self-assembled monolayer being surrounded by the second self-assembled monolayer having a longer chain length. Such wells may be advantageously fabricated according to certain embodiments, for example, when it is desirable to add greater lateral stability to particular biological materials, such as cells, which have been captured in the wells. Such wells may also form the basis for reaction vessels.

Additionally, self-assembled monolayers formed on the surface material may be modified after such formation for a variety of purposes. For example, a self-assembled monolayer-forming compound may be deposited on the surface material in a self-assembled monolayer, the compound having an exposed functionality including a protecting group which may be removed to effect further modification of the self-assembled monolayer. For example, a photoremovable protecting group may be used, the group being advantageously selected such that it may be removed without disturbance of the self-assembled monolayer of which it is a part. For example, a protective group may be selected from a wide variety of positive light-reactive groups preferably including nitroaromatic compounds such as o-nitrobenzyl derivatives or benzylsulfonyl. Photo-removable protective groups are described in, for example, U.S. Pat. No. 5,143,854, and incorporated herein in its entirety by reference, as well as an article by Patchornik, JACS, 92, 6333 (1970) and Amit et al., JOC, 39, 192, (1974), both of which are incorporated herein by reference in their entireties. Alternately, a reactive group may be provided on an exposed portion of a self-assembled monolayer that may be activated or deactivated by electron beam lithography, x-ray lithography, or any other radiation. Such protections and deprotections may aid in chemical or physical modification of an existing surface-bound self-assembled monolayer, for example in lengthening existing molecular species forming the self-assembled monolayer. Such modification is described in U.S. Pat. No. 5,143,857 referenced above.

Another preferred method of patterning the self-assembled monolayer to have an array matching the first layer 150, for example, is through soft lithography methods known in the art. Soft lithography has been exploited by George M. Whitesides and is described, by way of example, in U.S. Pat. No. 5,976,826 and in PCT WO 01/70389, both of which are herein incorporated by reference in their entireties. For example, the first layer 150 having micro-orifices 300 is placed over the self-assembled monolayer. The first layer makes conformal contact with support 140 by sealing against the self-assembled monolayer. A modifying solution is then placed on the first layer and allowed to contact the self-assembled monolayer surface exposed by the micro-orifices 300. A "modifying" solution is one that modifies the head group of the self-assembled monolayer to achieve a desired characteristic or that adds or removes a desired biomolecule to the head group. For example, a tether may be added to the exposed self-assembled monolayers head groups, which in turn captures a protein, which in turns provides an affinity for the cell to be patterned subsequently through the first layer 150 or the second layer 160.

Preferred surface portions of the patterned self-assembled monolayer are cytophilic, that is, adapted to promote cell attachment. Molecular entities creating cytophilic surfaces are well known to those of ordinary skill in the art and include antigens, antibodies, cell adhesion molecules, extracellular matrix molecules such as laminin, fibronectin, synthetic peptides, carbohydrates and the like.

Figure 14A:
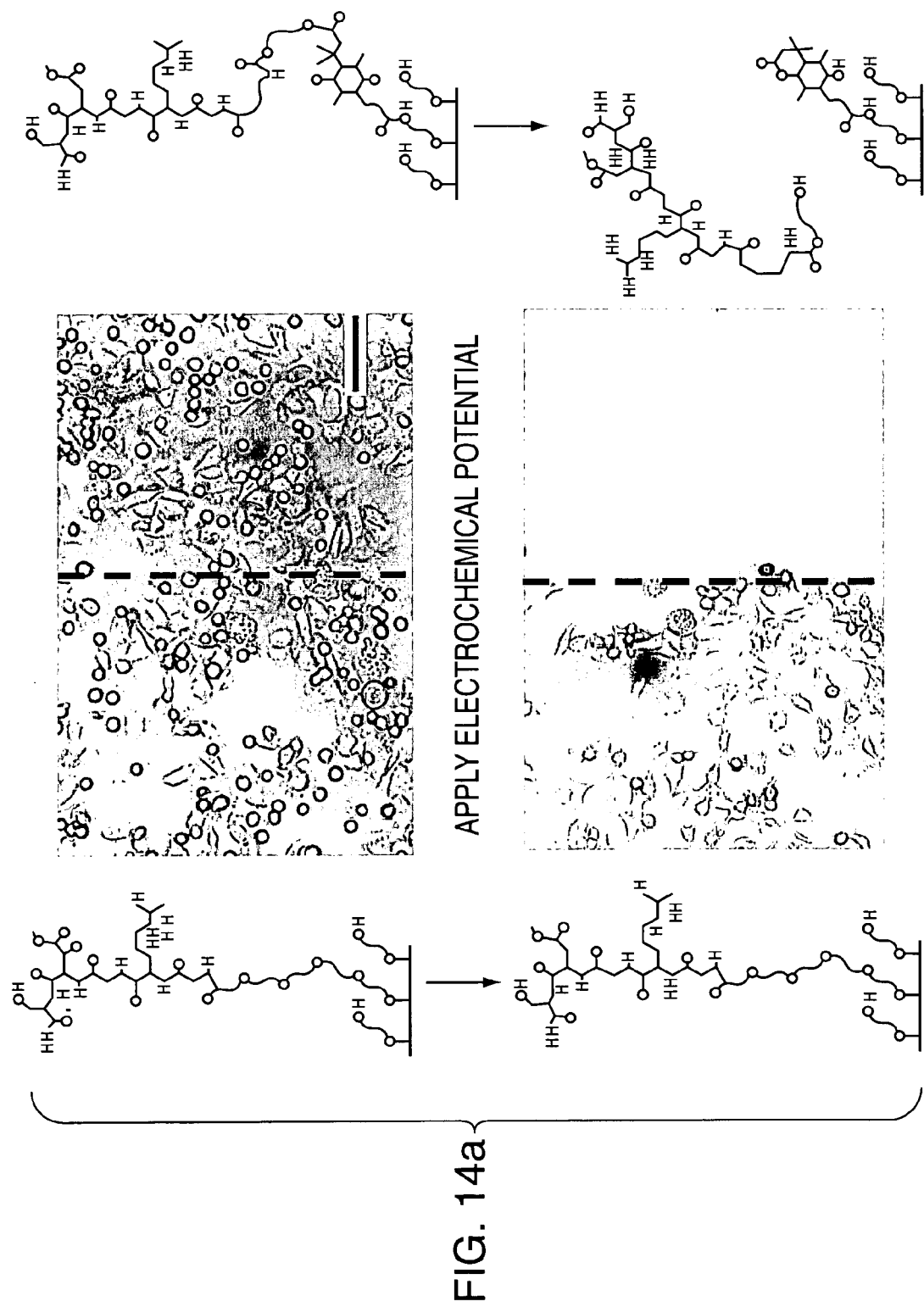
FIG. 14(a) illustrates a self-assembled monolayer having a "switchable head," in accordance with one embodiment of the present invention.

In a preferred embodiment of the present invention, the self-assembled monolayers are modified to have "switchable surfaces." For example, self-assembled monolayers can be designed with a "head group" that will capture a desired molecule. The head group is then subsequently modified at a desired point in time to release the captured molecule. In a preferred embodiment of the present invention, the head group is modified such that after release of the captured cell, the head group no longer will attract and attach subsequent cells. This release is important to allow the patterned cells to migrate. If a self-assembled monolayer did not have a "switchable" head group, the migration of the cell may be hindered. An example of a "switchable" control is depicted in FIG. 14. This figure depicts a particular peptide-presenting compound that allows cells to attach to itself. Upon application of an electrical potential, the peptide presenting compound is cleaved causing the release of cells from the support. Importantly, the portion of the peptide presenting compound that remains after application of the electrical potential is unable to bind cells, and thus eliminates the potential for non-specific cell binding.

It is also often desirable to utilize a bioinert support material to resist non-specific adsorption of cells, proteins, or any other biological material. The most successful method to confer this resistance to the adsorption of protein has been to coat the surface with poly(ethylene glycol) PEG. A variety of methods, including adsorption, covalent immobilization, and radiation cross-linking, have been used to modify surfaces with PEG. Polymers that comprise carbohydrate units also passivate surface, but these material are less stable and less effective than PEG. A widely used strategy is to preadsorb a protein—usually bovine serum albumin—that resists adsorption of other proteins. In addition, self-assembled monolayers that are prepared from alkanethiols terminated in short oligomers of the ethylene glycol group $[HS(CH_2)_{11}(OCH_2CH_2)_n OH:n=2-7]$ resist the adsorption of several model proteins. Even self-assembled monolayers that contain as much as 50% methyl-terminated alkanethiolates, if mixed with oligo(ethylene glycol)-terminated alkanethiolates, resist the adsorption of protein. Further, self-assembled monolayers that are terminated in oligo (ethylene glycol) groups may have broad usefulness as inert supports, because a variety of reactive groups can be incorporated in self-assembled monolayers in controlled environments.

In contrast to using a bioinert treatment or support material, by choosing an appropriate support or treatment, the surface can be modified to have any desired functionality. For example, the support can be treated to have immobilized biomolecules such as other cells, DNA/RNA, chemicals, or other biological or chemical entity. For example, the attachment and spreading of anchorage dependent cells to surfaces are mediated by proteins of the extracellular matrix, e.g. fibronectin, laminin, vitronectin, and collagen. A common strategy for controlling the attachment of cells to a surface therefore relies on controlling the adsorption of matrix proteins to the surface. Therefore, a preferred coating 220 includes extracellular matrix proteins, or hydrogels, including matrigel, or other coatings that mimic the extracellular matrix.

In another example, the coating comprises an immobilized entity that may or may not affect the behavior of the cell migration or motility, such as drugs, toxins, metabolites, test agents, etc. After placing the cells into the orifices of the first layer 150, the cells settle onto the surface of the support and are thus affected by the immobilized entity.

In yet another preferred embodiment, coating 220 may comprise coatings that provide a more in vivo-like environment for the arrayed cells. Since cells in vivo are usually in contact with other cell types, and since it has been observed that cell to cell contact effects the behavior of cells, a preferred coating 220 also comprises a secondary cell type to that of the primary cells to be arrayed. For example, cancer cells are surrounded by stromal cells. Thus, to more accurately correlate the migration or movement of cancer cells in vitro with what occurs in vivo, it is desirable to provide a coating 220 of stromal cells before patterning the cancer cells onto the coating. The growing of two different cell types together has been coined "co-culture" by those skilled in the art. Some commonly known co-cultures include hepatocytes/fibroblasts; astrocytes/dendrocytes; endothelial cells/leukocytes; and neural cells/glial cells. The present invention contemplate employing co-culture systems by providing a coating of one cell type and then arraying the second type onto the cellular coated support.

In yet another embodiment of the present invention, the support 140 may have a surface treatment in the form of "physical" modifications, such as striations, grooves, channels and indentations to effect cell motility and migration.

Figure 6A:
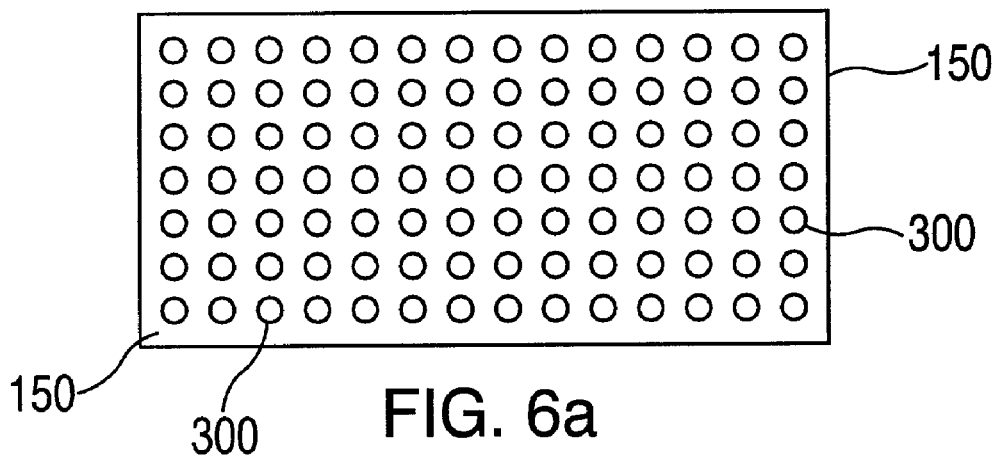
FIG. 6(a) is a top view of a first layer for a qualitative cell migration system, in accordance with one embodiment of the present invention.
Figure 6B:
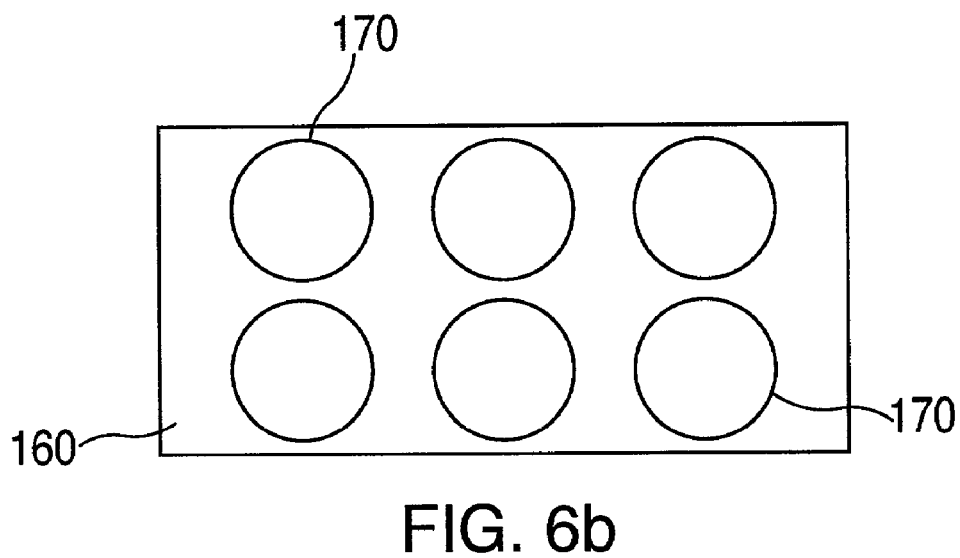
FIG. 6(b) is a top view of a second layer for a qualitative cell migration system, in accordance with one embodiment of the present invention.
Figure 6C:
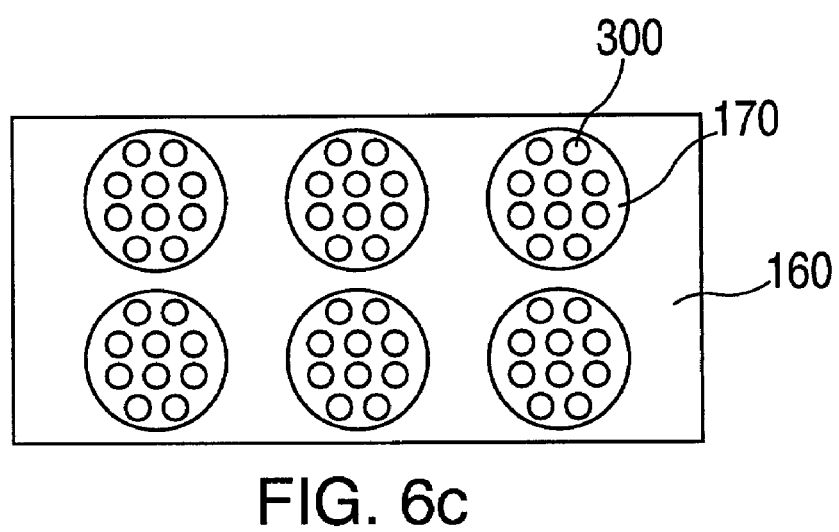
FIG. 6(c) is a top view of the second layer shown in FIG. 6(b) positioned on the first layer shown in FIG. 6(a).

The cell migration assay plate of the present invention allows for a broad range of patterns to be applied. For example, the entire support may define a pattern that is uniformly distributed across the support. FIG. 6(a) depicts one embodiment of the present invention wherein the first layer 150 has a plurality of micro-orifices uniformly distributed across the first layer 150. When the second layer 160 of FIG. 6(b) is placed onto the first layer 150 shown in FIG. 6(a), the arrangement of micro-wells 300 with macro-wells 170 as shown in FIG. 6(c) is created.

Figure 7A:
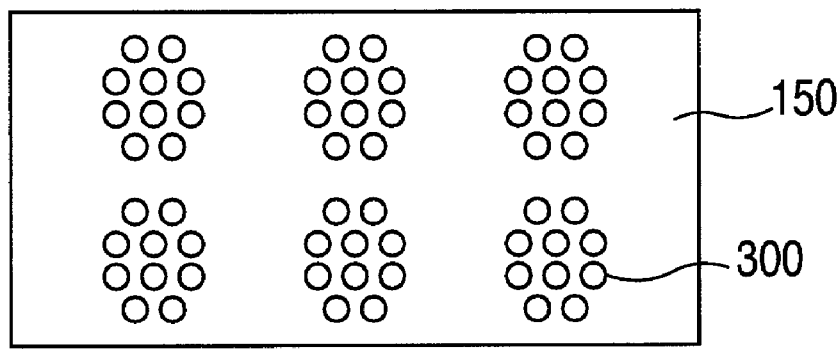
FIG. 7(a) is a top view of a first layer for a qualitative cell migration system, in accordance with another embodiment of the present invention.
Figure 7B:
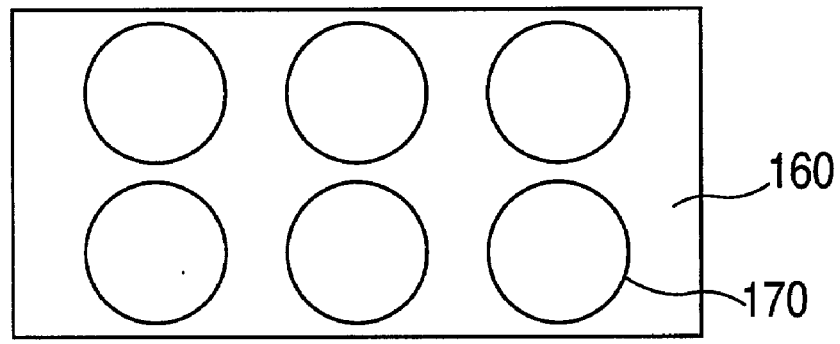
FIG. 7(b) is a top view of a second layer for a qualitative cell migration system, in accordance with another embodiment of the present invention.
Figure 7C:
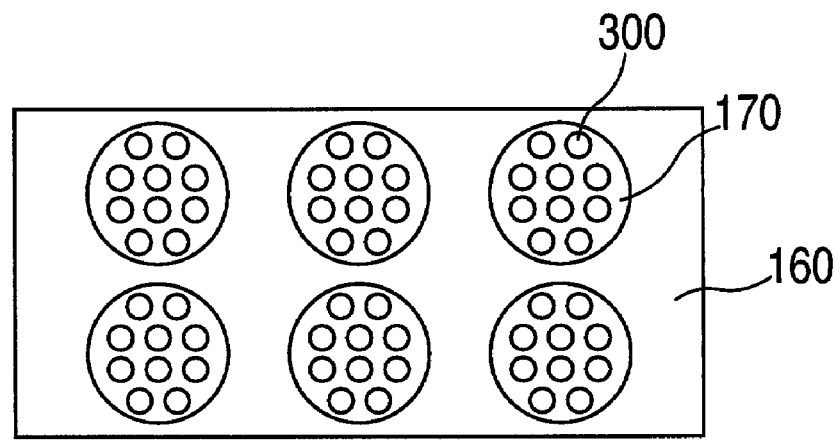
FIG. 7(c) is a top view of the second layer shown in FIG. 7(b) positioned on the first layer shown in FIG. 7(a).

FIG. 7(a) depicts another embodiment of the present invention, in which the support 140 is configured by arraying the micro-orifices 300 of the first layer 150 into discrete geometric patterns. When the second layer 160 of FIG. 7(b) is then placed onto the first layer 150 shown in FIG. 7(a), the arrangement of micro-wells 300 with macro-wells 170 as shown in FIG. 7(c) is created. These discrete areas preferably have the same size and pitch of standard micro-titer plates. The discrete areas may contain any desired number of individual patterned cells. For illustration purposes, FIGS. 7(a) depicts the first layer 150 having 6 discrete geometric patterns, each pattern occupying a corresponding area of the first layer 150. Within each of these 6 discrete areas are 10 micro-orifices. After applying cells to the support 140 through the micro-orifices 300, the resulting patterned support 140 will define six macro-regions, each of these macro-regions defining ten micro-regions of patterned cells. Each micro-region may contain one cell or a plurality of cells.

The description of the embodiment of the present invention set forth above with respect to FIGS. 7(a)–7(c) demonstrates the flexibility of the cell migration assay plate of the present invention. By varying the number, size, and pitch of the micro-orifices 300 of the first layer 150 and/or macro-orifices 170 of the second layer 160 of assay plate 100, any desired configuration or pattern of cells can be achieved. According to the present invention, any number of macro-wells 151 could be defined by an assay plate, and in addition, each macro-well could circumscribe any number of micro-wells 141 to create a desired geometric pattern. As previously mentioned, preferred embodiments of the present invention have discrete areas that match the number, size and pitch of the footprint of standard micro-titer plates used in the industry. For example, one preferred embodiment comprises a second layer 160 having 96 discrete macro-orifices 170 that match the footprint of a 96-well micro-titer plate. Arranged on the first layer 150 so as to be situated within each one of the 96 discrete macro-orifices 170 are, for instance, 100 micro-orifices 300 configured to receive solutions of cells. The resulting arrayed support 140 has 96 areas, each having 100 separate micro-regions of cell(s).

In another embodiment of the cell migration assay plate of the present invention, there are means for aligning the layers of the device. For instance, in order to align the micro-orifices 300 of the first layer 150 with the macro-orifices 170 of the second layer 160, the first layer 150 may need to be aligned precisely on the second layer 160. FIG. 3(a) depicts physical aligning means 190 and visual aligning means 192, one or both of which may be employed in the present invention. Physical aligning means 190 may comprise protrusions, pins, prongs, or the like that extend from the support. In one embodiment of the present invention, physical aligning means 190 are prongs that protrude from the support 140 and extend through guidance orifices 194 in layers placed thereon. An example of guidance orifices 194 is shown in FIG. 4(a). In another embodiment, the support 140 has a raised outer frame or ridge comprising a wall made of rigid material on the perimeter edge of the support 140, such as wall 196 illustrated in FIG. 3(a). The spatial constraints of the frame or wall 196 guide layers placed thereon into the correct position. The visual means 192 may include markings on the support 140 and/or on other layers to guide the placement of each additional layer on top of the next layer. Visual aligning means 192 include, but are not limited to, markings such as dots or cross hatches.

Figure 8A:
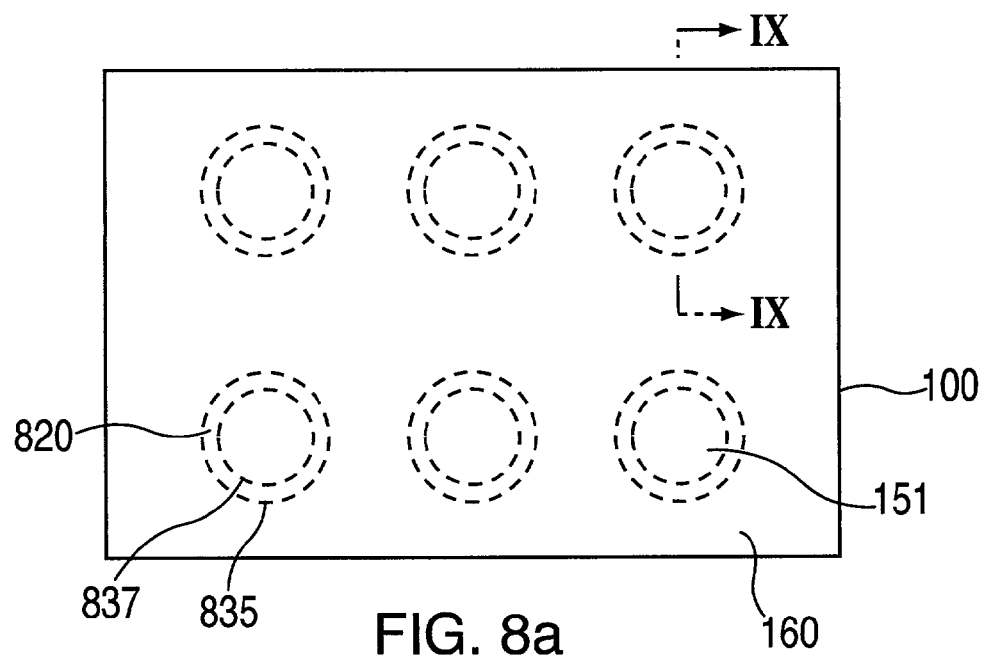
FIG. 8(a) is a top view of a qualitative cell migration assay plate, in accordance with another embodiment of the present invention.

FIG. 8(a) is a top plan view of a cell migration assay plate 100 in accordance with still another alternative embodiment of the present invention. In this embodiment, rather than being cylindrically shaped, the macro-wells 151 are funnel-shaped. Moreover, rather than being open and exposed to the atmosphere, the macro-wells 151 in this embodiment are shown as being capped with a cap 820. The cap 820 may comprise one or more materials configured to conform to at least in part an upper surface of the second layer 160 and sealably engage itself with the openings of the macro-wells 151. In the embodiment of the present invention shown in FIG. 8(b), cap 820 includes a seal 930 made of a first material that acts as a plug with respect to the macro-well 151, and a continuous covering layer 835 made of a second material and extending across an upper surface of the second layer 160. The cap 820 may be useful for preventing evaporation of assay solutions that may be placed into the macro-wells 151 and/or during the storage and transport of the cell migration assay plate.

Figure 8B:
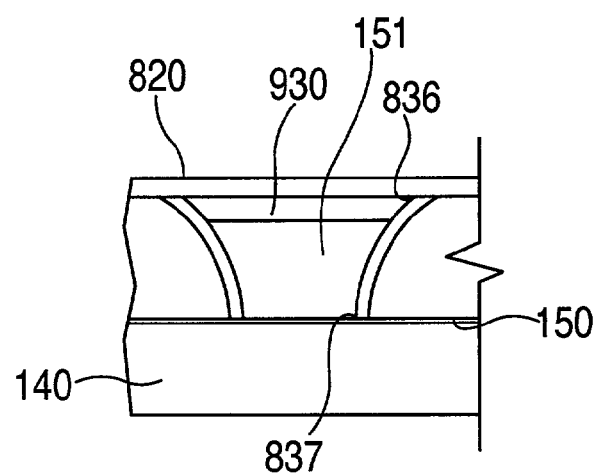
FIG. 8(b) is a cross-sectional view of the qualitative cell migration assay plate shown in FIG. 8(a), taken along the lines IX—IX.

FIGS. 8(a) and 8(b) also depict a lining 835 that may be used to form and line each macro-well 151 of the cell migration assay plate 100. This lining, which has a top edge 836 and bottom edge 837, may be made from a material different from the material of the cell migration assay plate 100 in order to provide the macro-wells 151 with properties other than those attributable to the cell migration assay plate 100 material. Moreover, the lining 835 may also be used to form the cell migration assay plate 100 during its manufacture by positioning the linings in space and then by pouring the material of the cell migration assay plate material around them.

The funnel shape of the linings 835 and of their corresponding macro-wells 151 is seen in FIG. 8(b). The first layer 150, support 140, cap 820, seal 930, top edge 836, and bottom edge 837 can also be seen in this figure. Moreover, as is also seen in FIG. 8(b), the linings 835 define and form the shape of the macro-wells 151 and sealably engage the first layer 150 located on top of the support 140.

Figure 8C:
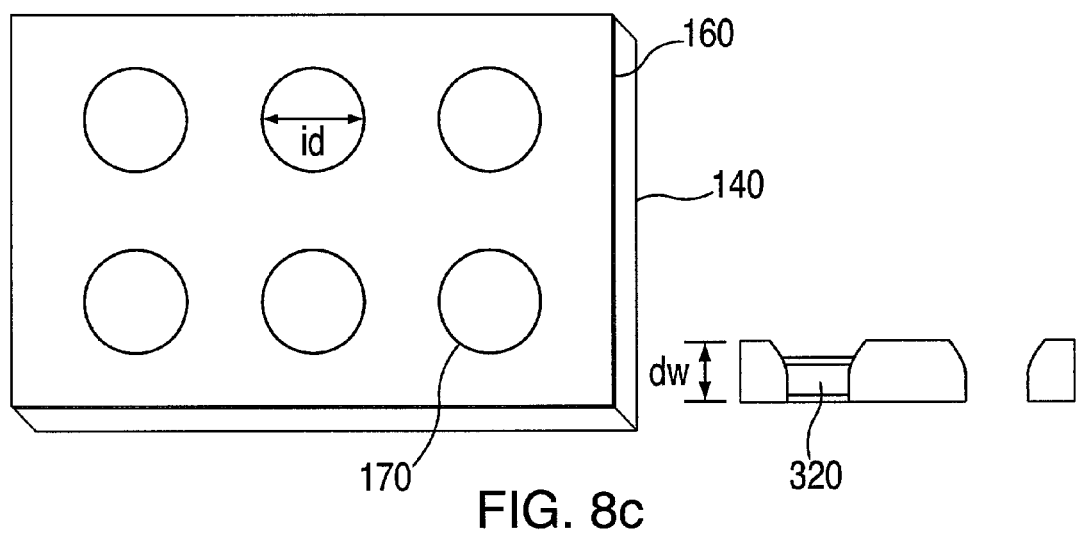
FIG. 8(c) is a top-view of a qualitative cell migration assay plate, in accordance with another embodiment of the present invention.
Figure 8D:
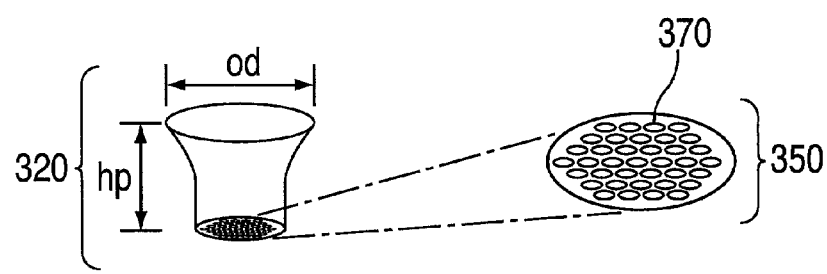
FIG. 8(d) is a cross-sectional view of a plug insertable into the qualitative cell migration assay plate shown in FIG. 8(c).

FIGS. 8(c) and 8(d) depict another embodiment of a cell migration assay plate 100 comprising plugs 320. In the shown embodiment, a second layer 160 defining macro-orifices 170 is placed onto a support 140. According to one embodiment of the invention, plugs 320 having an outside diameter "OD" smaller than an inner diameter "ID" of a macro-well 151 is configured for insertion into each macro-orifice 170. In the embodiment shown, the height of the plug, designated as "HP," is shorter than the depth of the second layer corresponding to a depth of the macro-well 151 and, designated as "DW," so as to enable test substances to be added at a subsequent time into the openings of the macro-orifices 170. Each of these plugs 320 has a membrane 350 at a bottom surface thereof, membrane 350 defining micro-regions 370 of cells in a defined geometric pattern. Plugs 320 are preferably dimensioned so as to be insertable into respective macro-wells 151 of the assay plate 100.

In another embodiment of the cell migration assay plate according to the present invention, cap 185 (not shown) is placed on top of the second layer 160. Cap 185 may be composed of rigid or flexible materials, described previously. Cap 185 is useful for preventing evaporation of assay solutions that will be placed onto the device through the macro-orifices 170.

Fabrication of the Qualitative Cell Migration Assay Plate

The cell migration assay plate according to the present invention having a first layer 150 and a second layer 160 may be manufactured according to the present invention by two methods: a single-piece fabrication method on the one hand, and a two-piece fabrication on the other hand, as will be described further below. It is understood, however, that the present invention includes within its scope other methods for manufacturing the assay plate according to the present invention that would be within the knowledge of a person skilled in the art.

Figure 9A:
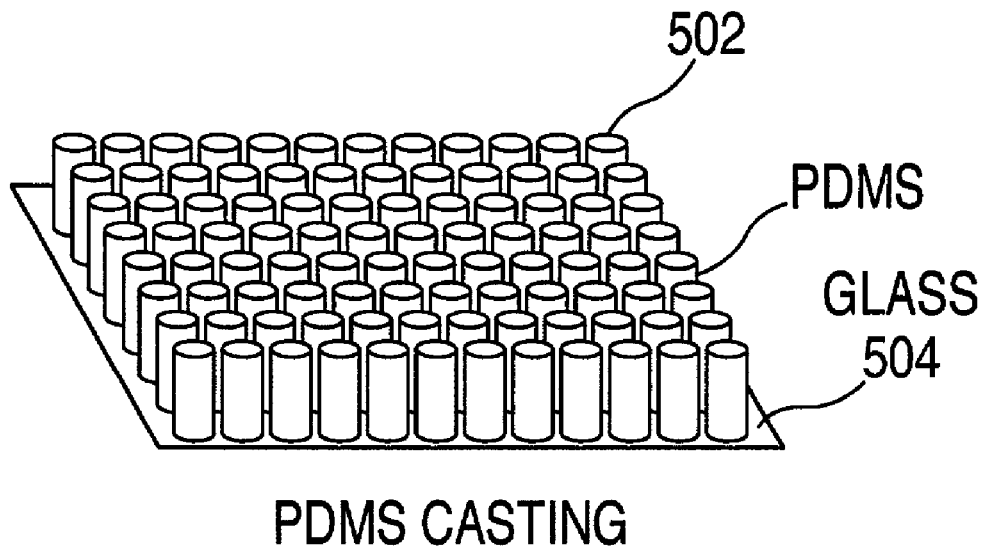
FIG. 9(a) is a perspective view of a PDMS casting having a plurality of macroposts disposed thereon, in accordance with one embodiment of the present invention.
Figure 9B:
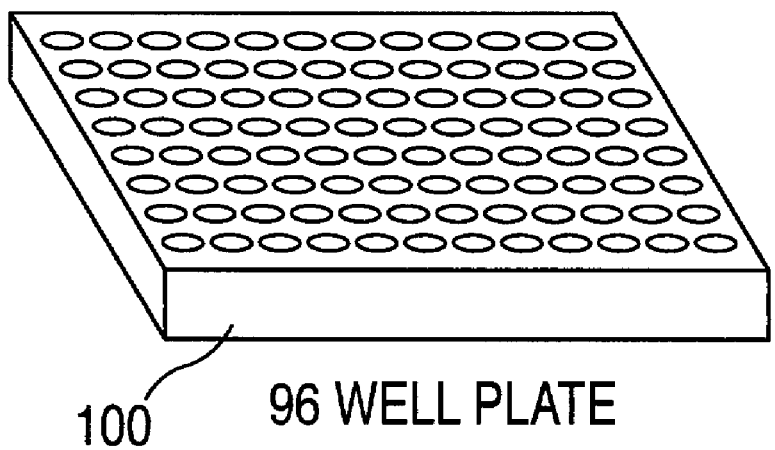
FIG. 9(b) is a perspective view of a 96-well microtiter plate that may be employed for casting the macrocosms shown in FIG. 9(a).

By forming the cell migration assay plate of the present invention in a single sequence of pouring, degassing, and curing, the manufacturing cycle time is reduced and a seal between the first layer and the second layer of the device is improved. The main advantage of this method is that it requires no manual handling of a preferred material (a thin PDMS membrane). According to various embodiments of the invention, a single-piece fabrication method may be employed wherein the device is formed on an original silicone/photoresist membrane master. FIG. 9(a) depicts a device comprising a silanized array of PDMS macrocosms 502 to form the macro-orifices in the second layer. These macrocosms 502 are formed by casting PDMS against a standard micro-titer plate 100 as shown in FIG. 9(b), such as a 96-well micro-titer plate, for example, and by sealing the resulting structure to a glass slide 504.

The use of PDMS macrocosms 502 provides a convenient method for fabricating the patterning layers. Silanization of PDMS using a perfluorosilane renders its surface resistant to lesion by the PDMS precursor and eliminates cross-linking of PDMS into the posts. The macrocosms are preferably prepared using PDMS, but many other materials May be used, such as Teflon, metal (e.g., aluminum), and other polymers. As previously mentioned, a 96-well plates may be used as a master, though lower and higher densities based on 12, 24, 384 and 1586 well configurations may also be used. The standard micro-titer plate footprints are preferred because many detection schemes have been developed for the same. After the PDMS macrocosms 502 are oxidized in air plasma (1 minute at 300 mTorr, 6 watts), they are silanized by immersion in a fluorosilane solution (1% by volume in methanol).

Figure 10A:
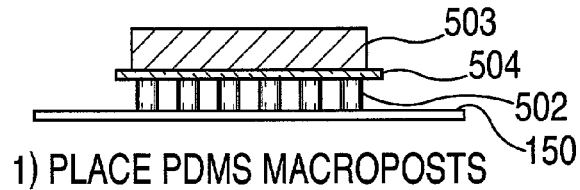
FIGS. 10(a) through 10(c) illustrates steps that may be performed in order to fabricate first and second elastomeric layers, in accordance with one embodiment of the present invention.
Figure 10B:
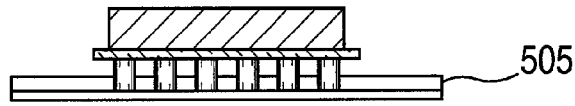
Figure 10C:

FIGS. 10(a) through 10(c) illustrate schematically respective stages corresponding to one embodiment of a method according to the present invention in which the first layer and the second layer of an embodiment of the assay plate of the present invention may be fabricated using the macrocosms 502 as previously described. Although the following description is with respect to the embodiments of the assay plate of FIGS. 1(a)–7(c), it is understood that the methods described with respect to FIGS. 10(a)–11(c) and with respect to cell patterning are equally applicable to other embodiments of the assay plate of the present invention. Prior to the performance of the step shown in FIG. 10(a), a PDMS precursor is spin-coated onto a pattern of photoresist posts arranged in an array of any desired shape, diameter and pitch in order to produce a first layer, such as first layer 150. A preferred array has 100 μm-diameter posts in a 3"×3" array (200 μm center-to-center period). The first layer 150 is then cured on the master. Next, as is shown in FIG. 10(a), the silanized macrocosms 502 are placed on top of the membrane and a weight 503 (approximately 500–1000 g) is placed onto the glass backing 504. The macrocosms 502 seal against the first layer 150, i.e., the PDMS membrane. As shown in FIG. 10(b), PDMS prepolymer 505 is poured onto the first layer 150, and flows around the macrocosms 502 and forms a thick (~5 mm) plate 505 on top of the first layer 150. As shown in FIG. 10(c), after curing the PDMS, the weight 503 and the macrocosms 502 are removed, and the resulting first layer 150 and second layer 160 together can be peeled off the master more easily and reproducibly than the first layer 150 alone.

Figure 11A:
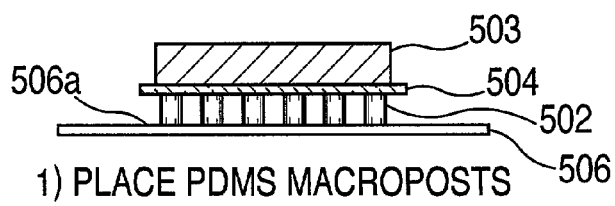
FIGS. 11(a) through 11(c) illustrates steps that may be performed in order to fabricate first and second elastomeric layers, in accordance with another embodiment of the present invention.
Figure 11B:
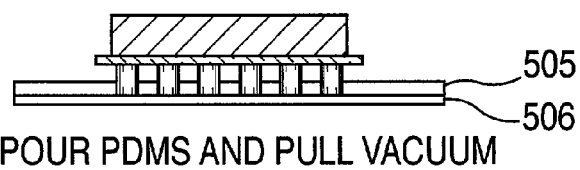
Figure 11C:

FIGS. 11(a) through 11(c) illustrate schematically respective stages corresponding to another embodiment of a method of the present invention according to which the first layer and the second layer of an embodiment of the assay plate of the present invention may be fabricated using the macrocosms 502 as previously described. The shown method, contrary to that of FIGS. 10(a)–10(c), does not incorporate a spin-coating step. Instead, the first layer, such as first layer 150, and the second layer, such as second layer 160, are formed and cured simultaneously. Here, as shown in FIG. 11(a), the macrocosms 502 are placed directly onto a silicon wafer 506 patterned with photoresist posts 506a. Then, as shown in FIG. 11(b), a PDMS precursor is poured onto the silicon wafer 506. Then, as shown in FIG. 11(c), a vacuum is applied to the device so as to remove any air trapped under the macrocosms and to urge the PDMS to fill the spaces between the photoresist posts 506a and between the macro-posts 502.

An alternative fabrication method (not shown) involves the separate formation of the second layer, such as second layer 160, and the first layer, such as first layer 150, followed by the assembly, via adhesion, of the layers. This method is advantageous as it lends itself well to high throughput—the first layer and the second layer are relatively straightforward to make using conventional processes such as spin-coating and molding. After the first layer and the second layer are made, they are aligned and bonded together. Care must be taken when handling the thin membrane component.

The assembly of the two layers 150 and 160 may be accomplished using one of multiple methods, for instance plasma oxidation, using an adhesive layer, using double sided tape or using mechanical methods. When an adhesive layer is used, a PDMS precursor may be used to bond the two layers. This precursor may be crosslinked either thermally or photochemically. Additionally, any other "glue" that can adhere to the PDMS surface may be used. The present invention also contemplates that double-sided adhesive tapes that can adhere strongly to the surface of PDMS can be used. In various other embodiments, mechanical methods may also be employed. In some applications, mechanical pressure may be maintained on the layers throughout the course of an experiment. Because PDMS can deform under pressure and act as a "gasket," mechanical sealing is a practical solution to assembling the components. One of the advantages to using mechanical methods over glues and tapes is that the assembled structure may be disassembled quickly without resulting in any damage to the device or the patterned material.

The present invention is also directed to methods of patterning cells using the cell migration assay plate of the present invention. In a preferred method of patterning cells according to the present invention, a first layer, such as first layer 150, is placed on a support 140, and the second layer, such as second layer 160, is placed on top of the first layer. The positioning of the macro-orifices 170 over the micro-orifices 300 may be assisted by the use of an alignment means as discussed above. In one embodiment, cells are patterned through the first layer 150 and allowed to settle and are applied to the support 140 to create an arrayed support 140 having micro-regions of adhered cells. Each micro-orifice 300 can receive the same cell containing solution or a different cell containing solution. The first layer 150 may then be removed. In this embodiment, it is preferred that the first layer 150 is coated with BSA or other cytophobic materials to resist cellular attachment. The second layer 160 is then aligned over the arrayed support 140. The macro-orifices 170 define macro-wells 151 encompassing a plurality of micro-regions of cells. Test agents can then be added through the macro-wells 151 to contact the micro-regions of arrayed cells. Each macro-well 151 can receive the same or a different test agent.

Figure 12A:
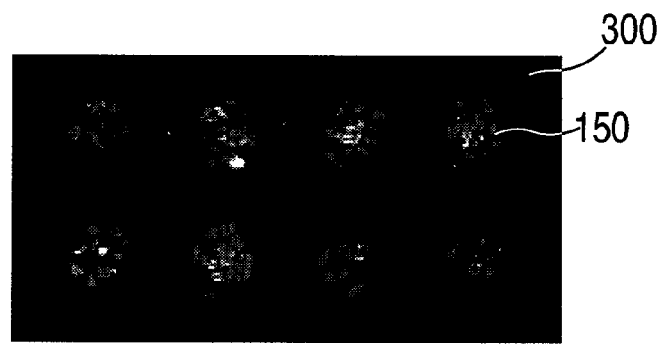
FIG. 12(a) illustrates a first cell type patterned into micro-orifices, in accordance with one embodiment of the present invention.
Figure 12B:
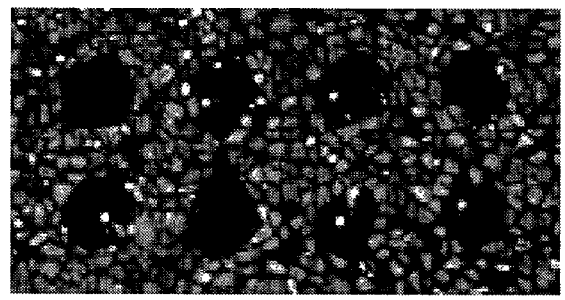
FIG. 12(b) illustrates a second type of cells arrayed around the first cell type shown in FIG. 12(a).
Figure 12C:
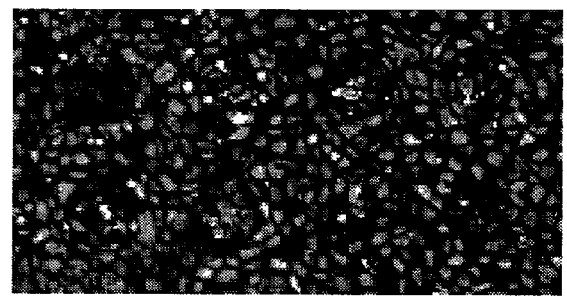
FIG. 12(c) illustrates an overlayed arrangement of the first and second cell types shown in FIGS. 12(a) and 12(b).

In an alternate embodiment, the first layer 150 is placed on the support 140, and the second layer 160 is placed on top of the first layer 150. The positioning of the macro-orifices over the micro-orifices 300 may be assisted by the use of an alignment means as discussed above. Cells of a first type are patterned through the first layer 150 and are applied to the support 140 in a pattern to create micro-regions of adhered cells. The first layer 150 is removed. The second layer 160 is then mated to the support. The second layer 160 has macro-wells 151 that encompass a plurality of micro-regions of the first cell type. A solution having cells of a second type is then placed into each of the macro-wells 151 to fill in around the micro-regions of the first cell type. The cells are allowed to attach to the support. Test agents then may be added into the macro-wells to contact the cells on the support 140. Each macro-well 151 can receive the same or a different test agent. FIG. 12(a) depicts a first cell type, e.g., MS1 (endothelial cancer cells), patterned into micro-orifices 300 of the first layer 150. After removal of the first layer 150, a second type of cells, e.g., 3T3 normal fibroblast cells, as shown in FIG. 12(b) is arrayed around the first cell type to create an overlayed arrangement as shown in FIG. 12(c). Then method illustrated in FIGS. 12(a)–(c) is commonly referred to as resulting in a "co-culture."

In another embodiment, both the first layer 150 and the second layer 160 are brought into contact with each other and are placed on top of the support 140. The cells are patterned through the macro-wells 151 of the second layer 160 and through the micro-orifices 300 of the first layer 150 to contact and attach to the underlying support 140. The resulting patterned support 140 has micro-regions of attached cells. Test agents are then added to the macro-wells 151 to contact the patterned cells. Each macro-well 151 can receive the same or a different test agent. In another embodiment, discussed previously above, the support 140 is first coated with a coating 220 before the first layer 150 is mated to the support and before the micro-orifices receive a solution of cells.

Because the cells are patterned in predetermined arrays by their placement through the micro-orifices 300 of the first layer 150, the exact positions of the cells are known and identifiable. The effects on movement or migration of the arrayed cells can be studied more precisely by measuring the movement or lack of movement of the cells away from their starting positions. In addition, since the arraying is brought about by the constraints of the micro-orifices 300 of the first layer 150, the precise pattern can be duplicated across the support in the areas encompassed by each of the plurality of macro-wells 151 by having the same geometric pattern of micro-orifices 300 in each macro-well 151. This reproducibility of cellular patterns on a support 140 provides for a quick and reliable comparison of cellular movement of the cells in each macro-well 151 against other macro-wells 151. Furthermore, within each macro-well 151, each micro-region of cell(s) is illustrative of the other micro-regions within that macro-well 151. For example, because each of the micro-orifices 300 can be fabricated to be of the same size and shape, and the same amount of cell(s) can added to each micro-orifice 300, one can observe a micro-region of cells patterned by a first micro-orifice 300 at a first time point and later observe a second micro-region of cells patterned by a second micro-orifice 300 at a second time point and compare the observations recorded at the two time points. Since the cell(s) in each of the micro-orifices 300 were exposed to the same conditions, and were patterned by identical micro-orifices 300, one need not go back to the previously observed micro-region 300 over the time course of the assay.

Further, having cells patterned in identical predetermined starting positions in each macro-well 151, the effects of a first test agent on a cell population in a first macro-well 151 can more accurately be compared to effects of a second test agent on a cell population in a second macro-well 151.

The flexibility of the cell migration assay plate of the present invention and the flexibility in the methods of patterning cells using the cell migration assay plate of the present invention provide for numerous cell migration assay configurations. A virtually unlimited amount of configurations can be achieved simply by choosing various dimensions, numbers, shapes and pitch of micro-orifices 300 and macro-orifices 170, as well as by modifying the coating 220 on the support 140.

Using the cell migration system and the cell migration assay plate of the present invention, novel cell migration assays can be performed. These assays measure the migration or motility of patterned cells. Since the present invention provides for patterning cells in discrete arrays, the measurement of cell movement/migration is more accurate as it measures motility or migration away from a predetermined starting position created by the micro-orifices of the first layer. In addition, the cell migration/motility assays of the present invention provide for ongoing/real-time monitoring of the cells as the cells can be visualized through light or flourescent microscopy and need not be stained and fixed for counting as previously required by the Boyden chambers. The present invention contemplates the monitoring and observation of cellular movement or migration of numerous cell types, which will provide much needed information about processes in the body that occur as a result of cell movement.

Cellular movement is implicated in numerous systems and responses in the body. For example, leukocyte movement is involved in inflammatory and immune responses. Leukocyte cell classes that participate in cellular immune responses include lymphocytes, monocytes, neutrophils, eosinophils, and mast cells. Leukocytes accumulate at a site of inflamation and release their granular contents such as various hydrolytic enzymes an other toxic components into the extracellular-spaces. As a result, the surrounding tissue is damaged. Numerous chronic inflammatory disease are thought to involve the aberrant presence of leukocytes in tissues. Infiltration of these cells is responsible for a wide range of chronic inflammatory and autoimmune diseases, and also organ transplant rejection. These diseases include rheumatoid arthritis, psoriasis contact dermatitis, inflammatory bowel disease, multiple sclerosis, atherosclerosis, sarcoidosis, idiopathic pulmonary fibrosis, allograft rejection and graft-versus-host disease, to name a few.

In another process of the body, cancer cells break off from a tumor and metastasize to other parts of the body. Thus, cell migration assays that provide a reliable study on the ability of potential drug candidates to inhibit cancer cell growth and/or metastasis would provide valuable information to the field of oncology.

In one embodiment of the cell migration/motility assay of the present invention, cells are first allowed to migrate through the micro-orifices 300 of the first layer 150 onto the support 140 to produce an arrayed support 140. The cells are allowed to attach and grow to confluence within the micro-orifices 300. The first layer 150 is then removed. The second layer 160 is placed on top of the arrayed support 140 to form macro-wells 151 encompassing areas of patterned cells. A test solution is added through the macro-orifices 170 of the second layer 160 and allowed to contact the arrayed cells. The effects of this test solution on cell movement or migration is then observed. FIGS. 13(a) through 13(c) illustrate the stages according to the above embodiment of the assay of the present invention. FIG. 13(a) illustrates a second layer 160 sealed to a first layer 150. FIG. 13(b) illustrates cells that have been patterned through the first and second layers 150 and 160 onto the support 140 and are allowed to grow to confluence within the micro-orifices 300. An example of this is shown in FIG. 13(d). As shown in FIG. 13(c), the first layer 150 is then removed, and the cells arrayed on the support 140 are permitted to migrate, an example of which is shown in FIG. 13(e). The observation can be performed using any method known in the art, including but not limited to light microscopy and fluorescent microscopy.

In another embodiment of the cell migration/motility assay of the present invention used in conjunction-with embodiments shown in FIGS. 1(a)–7(c), the support 140 is treated directly with test agents or coated with a membrane having test agents coated thereon. The agents are then tested to determine whether they exert any chemotactic effect. In such a scenario, the micro-orifices 300 of the first layer 150 are smaller in diameter than the size of an individual cell to be plated. The cells are plated and allowed to squeeze through pre-defined arrays of micro-orifices 300 in response to the chemotactic agent on the support 140. The support 140 or the membrane is then observed for the cells. Since the micro-orifices 300 are designed in a pre-determined geometric pattern, the analysis and determination of cell migration through the first layer 150 onto the support results from a quick visual inspection of the support 140 for cells. For example, if the micro-orifices are arrayed in a 10×10 pattern (for a total of 100 cells), a quick visual review of the support or membrane would inform the scientist what percentage of cells migrated through the microoorifices. A high percentage of cells migrating corresponds to a strong chemotactic substance and a low percentage corresponds to a weak chemoattractant. In contrast to transwell chemotactic assays that involve establishing a top and bottom base line, no base line measurements are needed for the above assay to analyze the strength or weakness of a chemotactic substance.

In another embodiment of the cell migration/motility assay of the present invention, the support, such as support 140, is first coated with a coating 220 such as extracellular matrix proteins or matrigel (not shown). Cells are then plated onto the coated support. The migration or movement of the cells through the matrigel is observed. In still another embodiment of the assay of the present invention, the matrigel can contain test agents.

Figure 15A:
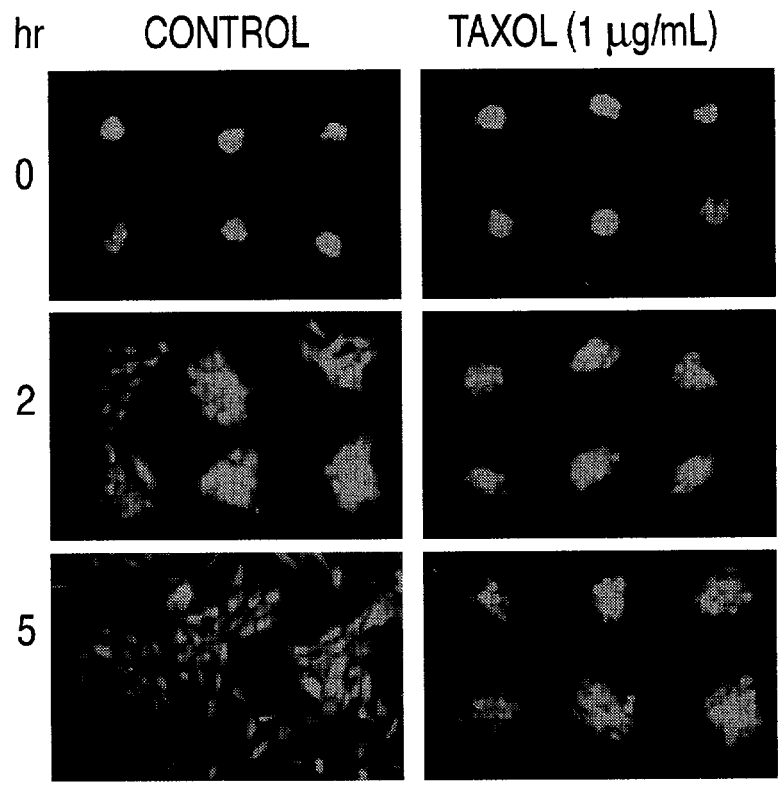
FIG. 15(a) illustrates the effect of a test agent on cell motility for a control group and a particular cell type, in accordance with one embodiment of the present invention.
Figure 15B:
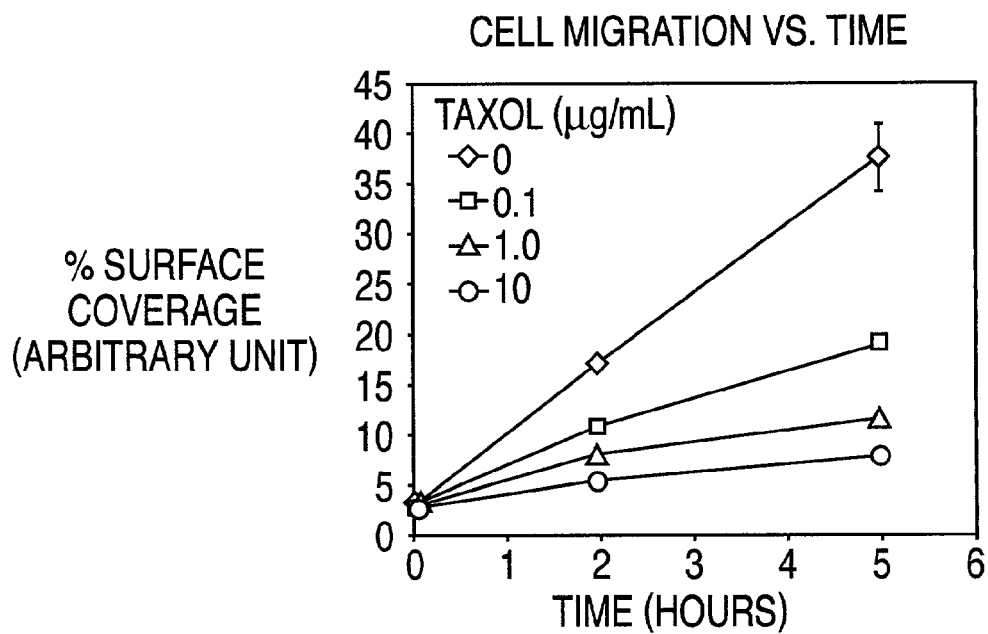
FIG. 15(b) is a graphical representation of the effects of the test agent on cell motility as shown in FIG. 15(a).

The cell migration/motility assay of the present invention allows one to study the effect of test agents and others both on cell motility and on cell shape. For example, cells may be patterned through micro-orifices, such as micro-orifices 300, of the first layer 150. The cells are allowed to attach to the support 140 and to grow to confluence. The walls of the micro-orifice 300 constrain the cell(s) and the cells take on the shape of the micro-orifice 300, e.g., circular. A test agent is applied through the micro-orifices 300 and is allowed to contact the cells. The first layer 150 is removed and the cells are observed. If the test agent affects cell movement, the cell will be "stuck" in place as it was patterned and may not change shape, i.e., it will remain circular if the patterning member had circular orifices. On the other hand, if the test agent does not effect cell movement, the cell will move away from its original patterned position and change shape from the patterned circular shape since the constraints of the first layer 150 had been removed. FIG. 15(a) illustrates, in its left column, an example wherein control cells, at various time intervals, e.g., 2 hours and 5 hours, are shown to have migrated away from their original pattern, designated as "hr 0." In contrast, cells treated with a common cancer drug, taxol, have retained their original circular pattern after these same time intervals, as shown in the right column of FIG. 15(a). FIG. 15(b) is a graph of the effect of various concentrations of taxol on cell movement as performed by a cell migration/motility assay of the present invention.

Figure 16:
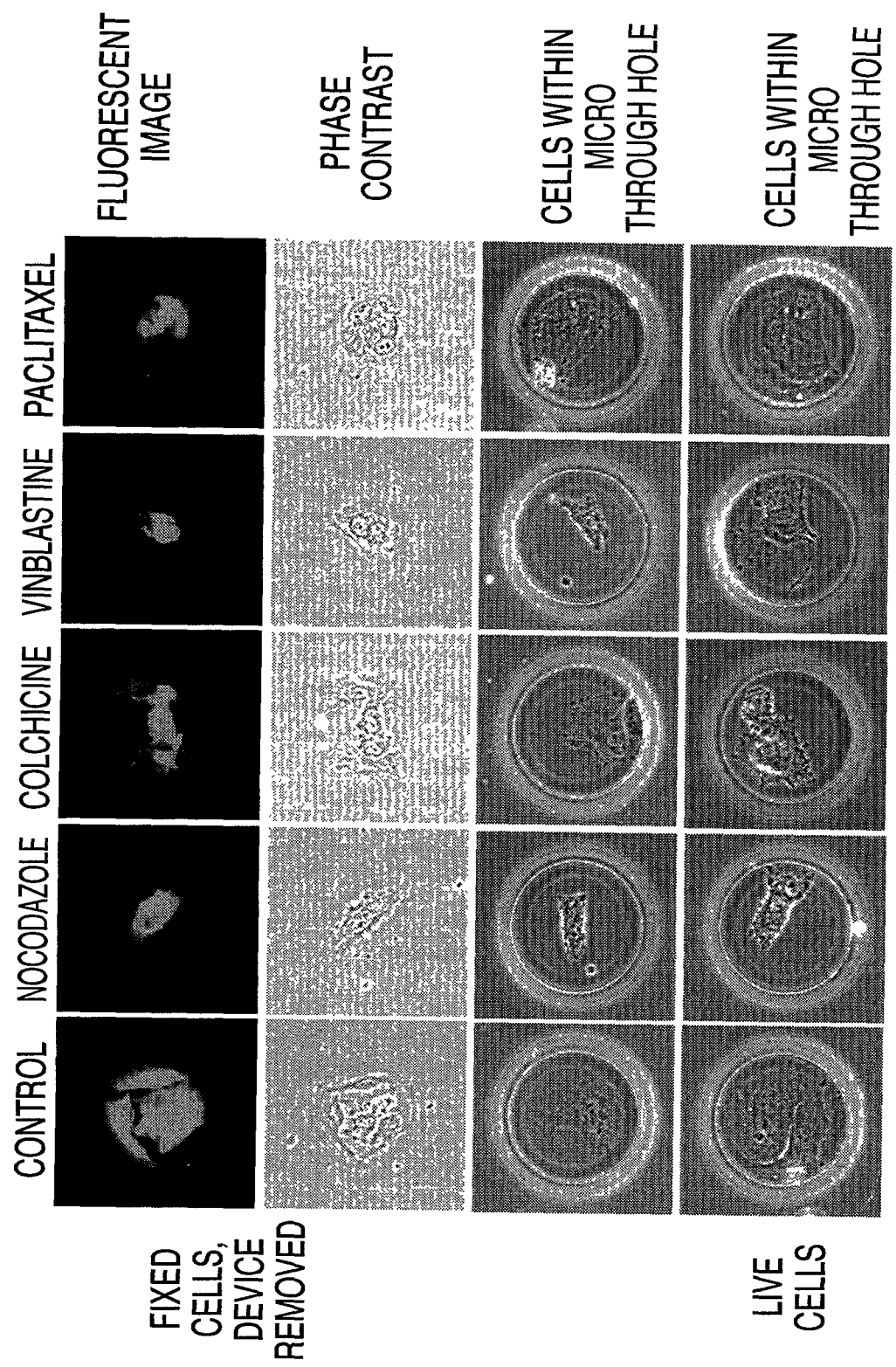
FIGS. 16 and 17 illustrate the effect of a various agents on cell motility for a group of cell, in accordance with various embodiments of the present invention.
Figure 17:
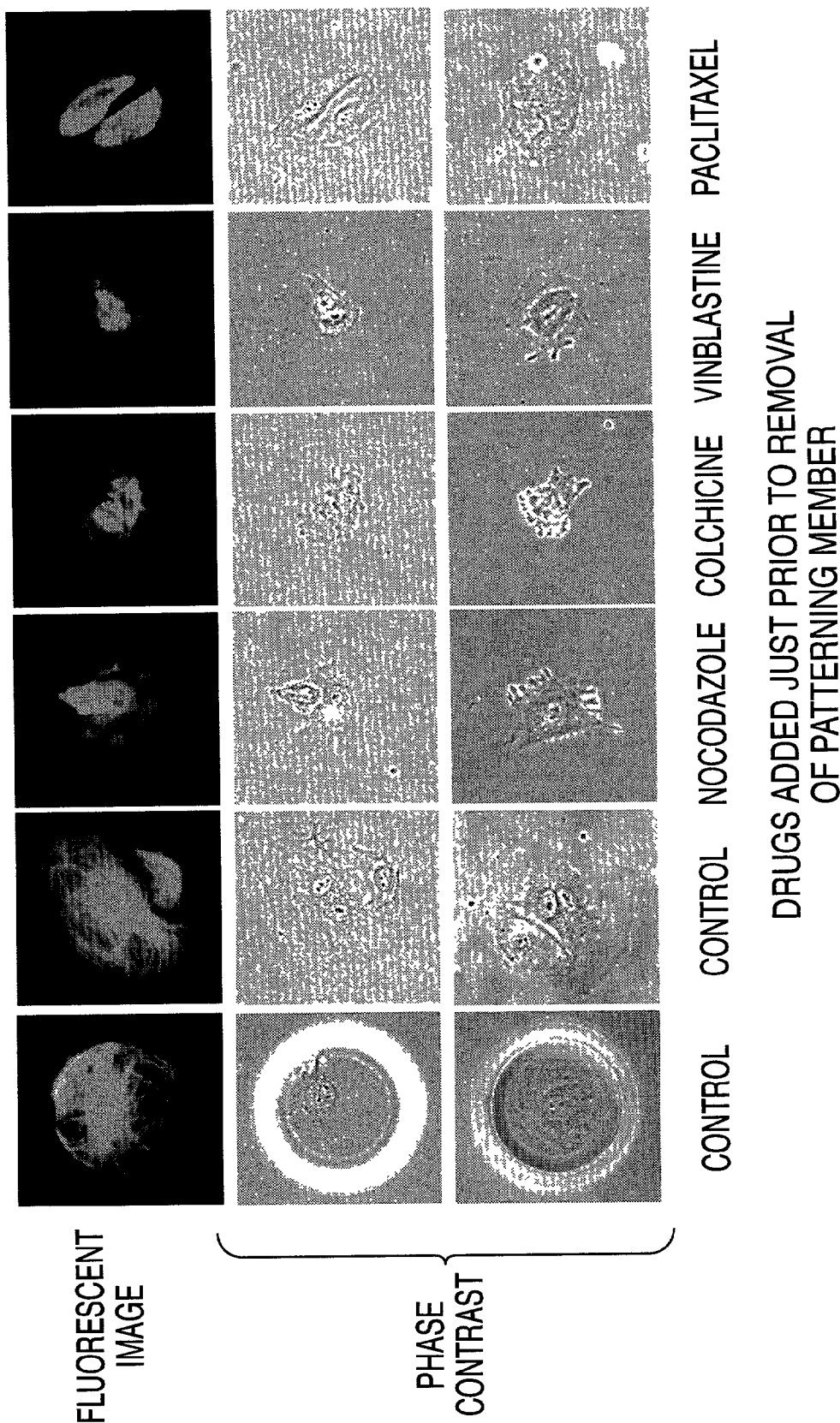

Alternatively, the test agent can be added before the cells have grown to confluency, i.e. the test agent is added to the cells before being patterned through the micro-orifices 300. If the test agent has no effect on cell motility, the cells will spread and achieve the shape of the micro-orifice 300. In FIGS. 16 and 17, a micro-orifice 300 is circular in shape. In the left column of FIGS. 16 and 17 are the control panel, which illustrate the cells having grown to a confluent circular pattern. As shown in the remaining columns, the cells that were treated with various test agents (nocodazole, colchicine, vinblastine, and paclitaxel) had their cellular movement arrested and thus never achieved a circular confluent pattern.

One embodiment of the present invention allows one to study the effect of test agents on cell proliferation as well as cell movement. This is particularly useful in cancer studies where proliferation rates are high. In this embodiment, the cells to be patterned are preferably stained or fluorescently tagged with two different stains or tags: the nuclei are stained with a different dye or fluorescent tag than the rest of the cell (i.e. a cytoplasmic dye or tag). The cells are patterned through the micro-orifices 300 of first layer 150. The cells are allowed to attach to the support 140 and to grow to confluence. A test agent is applied through the micro-orifices 300 and allowed to contact the cells. Alternatively, the test agent is added to the cells before the cells are patterned through the micro-orifices. The first layer 150 is removed. The cells are then observed for migration or movement and/or proliferation. Using two different tags or dyes, allows for the observation and recordation of cell number and increase thereof, and/or cell movement. Using this information in combination allows one to deconvolute the effect of motility from proliferation. That is, when the cells are later observed, having moved away from the original pattern, one can determine wether it is because of cell movement alone, proliferation alone, or the combination of movement and proliferation, by simply counting and comparing the number of nuclei at some later point in time compared to the number of nuclei at the beginning of the assay, i.e. at time zero.

Figure 18:
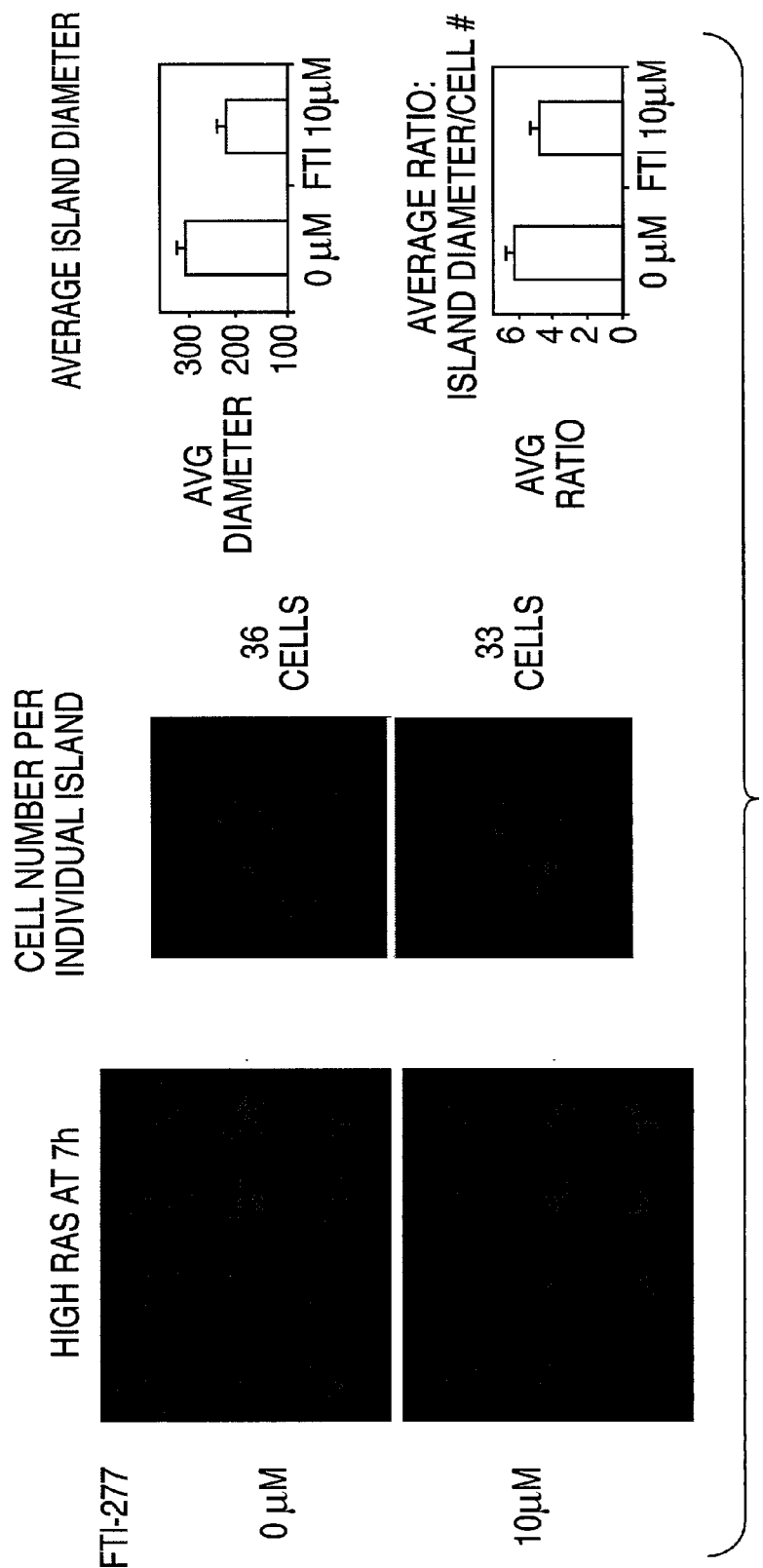
FIG. 18 is a graphical representation of the amount of cell motility relative to an amount of cell proliferation, in accordance with one embodiment of the present invention.

FIG. 18 demonstrates that the assays of the present invention can measure cell movement and are not merely measuring cell division. Over time the cells are seen to spread/move away form their original pattern, but their number remains essentially constant.

The present invention also includes methods of identifying microbes, methods of screening for the activity of drugs, methods for detecting toxic substances and methods for detecting intercellular reactions. In these various methods, solutions or suspensions containing the desired cell affecting agent are flowed in intimate contact with the living cells through the macrowells/macro-orifices. The effect(s) of the cell affecting agent on cell motion or migration is then monitored and measured.

The present invention may be used with a wide variety of prokaryotic and/or eukaryotic cells. Examples of such cells include, but are not limited to, human keratinocytes, murine L fibroblastic cells, canine MDCK epithelial cells, hamster BHK fibroblastic cells, murine CTLL lymphocyte cells, tumor cells and bacteria. In general, any living cells, including transfected cells, that can be successfully patterned may be used. The cells may be labeled with fluorescent markers known in the art, such as fluorescein, to assist in microscopic viewing.

Cell affecting agents can be anything that affects cell motility or migration. Examples of cell affecting agents include, but are not limited to, irritants, drugs, toxins, other cells, receptor ligands, receptor agonists, immunological agents, viruses, pathogens, pyrogens, and hormones. Examples of such cell affecting agents further include irritants such as benzalkonium chloride, propylene glycol, methanol, acetone, sodium dodecyl sulfate, hydrogen peroxide, 1-butanol, ethanol, and dimethylsulfoxide, drugs such as valinomycin, doxorubicin, vincristine, ribavirin, amiloride and theophylline; hormones such at $T_3$ and $T_4$, epinephrine and vasopressin; toxins such as cyanide, carbonylcyanide chlorophenylhydiazone, endotoxins and bacterial lipopolysaccharides; immunological agents such as inter-leukin-2, epidermal growth factor and monoclonal antibodies; receptor agonists such as isoproterenol, carbachol, prostaglandin $E_1$ and atropine; and various other types of cell affecting agents such as phorbol myristate acetate, magnesium chloride, other cells, receptor ligands, viruses, pathogens and pyrogens. In addition, the present invention can also test the synergistic effect that some of the cell affecting agents may have on other agents. In other words, the test agents maybe combined and mixed as necessary to better understand their combined synergistic properties.

In one cell migration/motility assay of the present invention, cells are patterned onto the support 140 through the micro-orifices 300 of the first layer 150. The cells are grown to a certain cell cycle stage and arrested in that stage of cell growth. Test agents are then added to the patterned cells and the effects of the agents are observed and monitored. The same test agent may be applied to the same cells at different life cycle stages and compared against each other to shed light on the effect of the test agent at different points along the cell cycle. In another embodiment, cells are "captured" at a certain cell stage by incubating them elsewhere but capturing them on a support having a coating of a ligand that would "grab" a cellular "tag" such as a protein, that is expressed only at a specific desired cell life cycle (e.g. G1, S, G2, M(standard cell cycle) or S, M(early embryonic cell cycle). In such an embodiment, the coated support would capture only those cells at desired life cycle stage.

In the qualitative cell migration system of the present invention, such as system 190 shown in FIG. 1(a), the observation system 110 and the controller 120 may be used to observe and analyze the real-time movement and behavior of cells as they respond to different and various stimuli. The observation system 110 and controller 120 may provide for real-time observation via a monitor (which is not shown). They may also provide for subsequent playback via a recording system either integrated with these components or coupled to them. In either case, these components may also monitor and analyze the cells as they progress through their reaction to the stimulus. System 190 may include any suitable observation system and controller as would be within the knowledge of a person skilled in the art.

The observation system 110 may include a microscope, high-speed video camera, or high-resolution digital camera, and/or an array of video cameras, and an array of individual sensors. Standard optical microscopy techniques can be used in a parallel setup to quantify the migration. Preferably, an inverted light field phase contrast microscope can be used to view the live cells. The observation system is connected to a controller to receive input for various observation parameters. The data observed by the observation system is sent to the controller for processing in a conventional manner.

Each of these embodiments allow the monitoring of the movement and behavior of the cells before, during, and after the stimuli, reactant or other test compound is introduced. At the same time, the observation system 110 may also generate signals for the controller 120 to interpret and analyze. This analysis can include determining the physical movement of the cells over time as well as their change in shape, activity level or any other observable characteristic. In each instance, the conduct of the cells being studied may be observed in real-time, at a later time or both.

Figure 19:
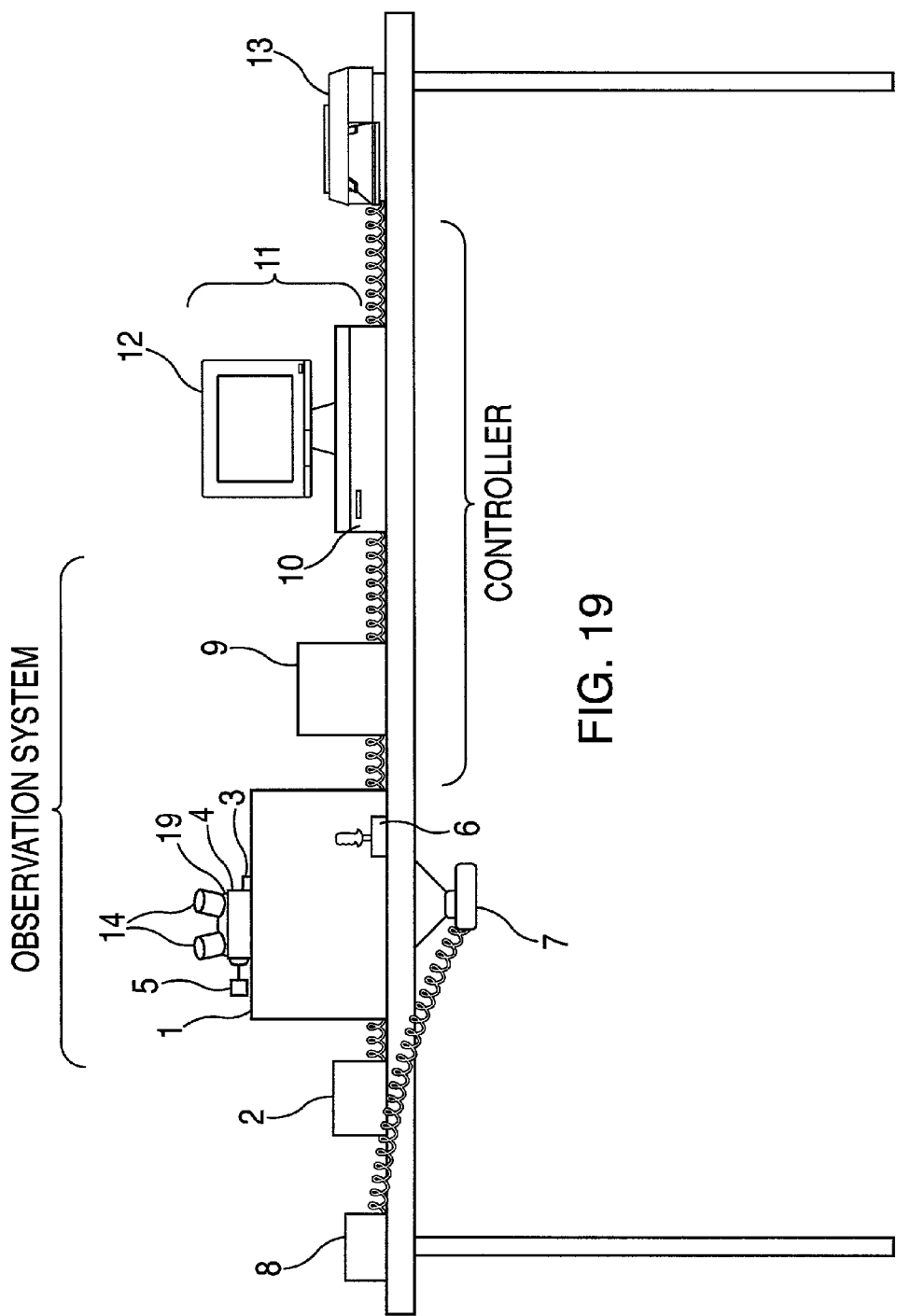
FIG. 19 is a schematic diagram of a system for measuring the migration or motility of cells, in accordance with one embodiment of the present invention.
Figure 20:
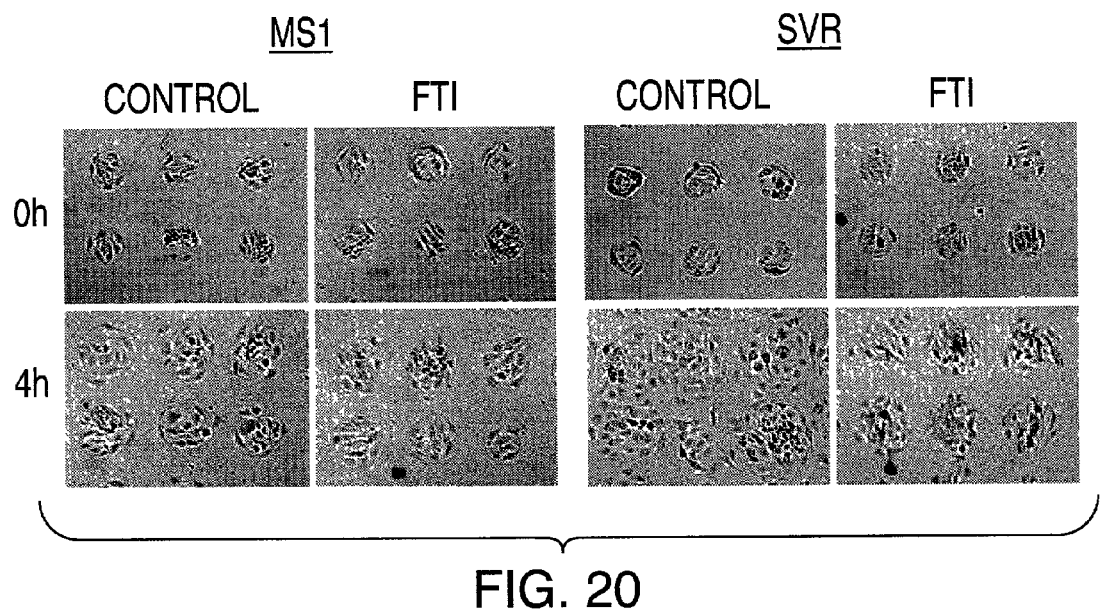
FIG. 20 contains the pictorial results of an assay using a qualitative cell motility assay plate showing farnesyl transferase inhibition in MS1 and SVR cells, in accordance with one embodiment of the present invention.

FIG. 19 is a schematic diagram of a system for measuring the migration or motility of cells, in accordance with one embodiment of the present invention. The system may use an inverted microscope 1 as shown in FIG. 19, which uses standard objectives with magnification of 1–100× to the camera, and a white light source (e.g. 100 W mercury-arc lamp or 75 W xenon lamp) with power supply 2. In alternate embodiments, the system may use an upright microscope. The system also includes an XY stage 3 to move the qualitative cell migration assay plate 4 in the XY direction over the microscope objective. A Z-axis focus drive 5 moves the objective in the Z direction for focusing. A joystick 6 provides for manual movement of the stage in the XYZ direction. A high resolution digital camera 7 acquires images from each well or location on the qualitative cell migration assay plate 4. A camera power supply 8 provides power to the camera 7. An automation controller 9 controls the automated aspects of the observation system, and is coupled to a central processing unit 10. A PC 11 provides a display 12 and has associated software, as is described briefly below. A printer 13 prints data corresponding to the observed cell migration/motility. Microscope oculars 14 are positioned so as to be looked through by a user of the system.

In a preferred embodiment of the present invention, the observation and control systems may be automated and motorized to acquire images automatically. In one embodiment, at the start of an automated scan, the operator enters assay parameters corresponding to the sample to be observed and to the arrangement of the qualitative cell migration assay plate. Assay parameters can include variables such as cell type, number of cells to be patterned into each micro-orifice, shape and pitch of micro-orifices, shape and pitch of macro-orifices, time periods between each image capture (scan), number of images to capture per macro-well and per scan, etc. Other parameters may include filter settings and fluorescent channels to match biological labels being used, etc. The camera settings may be adjusted to match the sample brightness. These parameters are advantageously stored in the system's database for easy retrieval for each automated run. The user specifies which portion of the assay plate the system will scan and how many fields in each macrowells to analyze on each plate. Depending on the setup mode selected by the user at step, the system either automatically pre-focuses the region of the plate to be scanned using an autofocus procedure to "find focus" of the plate or the user interactively pre-focuses the scanning region.

During an automated scan, the software dynamically displays the status of a scan in progress, such as by displaying data corresponding to the number of fields in macrowells that have been analyzed, the current macrowell that is being analyzed, and images of each independent wavelength as they are acquired, and the result of the screen for each macrowell as it is acquired. The assay plate may be scanned in any number of scanning patterns such as top to bottom, left to right, or in a serpentine style as the software automatically moves the motorized microscope XY stage 3 from macrowell to macrowell within the device. Those skilled in the programming art will recognize how to adapt software for scanning of standard microplate formats such as 24, 48, 96, and 384 well plates. The scan pattern of the entire plate as well as the scan pattern of fields within each well are programmed. The system adjusts sample focus with an autofocus procedure 104 through the Z axis focus drive 5, and optionally controls filter selection via a motorized filter wheel 19 and acquires and analyzes images.

Automatic focusing algorithms are described in the prior art in Harms et al. in Cytometry 5 (1984), p. 236–243, Groen et al. in Cytometry 6 (1985), p. 81–91, and Firestone et al in Cytometry 12 (1991), p. 195–206, which is incorporated by reference herein in its entirety. U.S. Pat. No. 5,989,835 describes a variation on the above methods, which is incorporated by reference herein in its entirety. The autofocus procedure is called at a user-selected frequency, typically for the first field in the first macrowell and then once every 4 to 5 fields within each macrowell. The autofocus procedure calculates the starting Z-axis point by interpolating from the pre-calculated plane focal model. Starting a programmable distance above or below this set point, the procedure moves the mechanical Z-axis through a number of different positions, acquires an image at each, and finds the maximum of a calculated focus score that estimates the contrast of each image. The Z position of the image with the maximum focus score determines the best focus for a particular field.

Because the locations and geometric patterns of the micro-regions and the macro regions are predetermined, the system can be designed or programmed to scan the plate at those locations. The migration or motility of a cell may be detected by any of a variety of known methods in the art, including visual monitoring, fluorescence or spectrophotometric assays based upon binding of fluorescently labeled antibodies or other ligands, cell size or morphology, or by the cells' spectrophotometric transmission, reflection or absorption characteristics either with or without biological staining. Standard light or electron microscopy can also be employed. When the detection system is a microscope, it may be positioned either above or below the assay plate. In the case of fluorescence assays, a detector unit may be placed above the assay plate or, if the assay plate is translucent, below the assay plate. In the case of transmission spectrophotometric assays, a translucent assay plate is used, a source of electromagnetic radiation is placed on one side of the assay plate and a detector unit on the other. In addition to visual monitoring, physical monitoring may also be employed. For example, movement of the cells may contact detectors placed on the assay plate causing changes in the detectors, which can be received and analyzed by the CPU. Because of the small distances between individual isolated cells permitted by the present invention, detectors employing fiber optics are particularly preferred. Such sources of electromagnetic radiation and such detectors for electromagnetic transmission, reflection or emission are known in the applicable art and are readily adaptable for use with the invention disclosed herein.

When an automated detector unit is employed, a standard or control plate may also be provided. Such an assay plate would contain micro-regions including micro-regions to which the cells have not migrated so that a reference would be provided and the detector would recognize such micro-regions. In addition, micro-regions bearing cells of known types could be provided to act as references to allow the detector unit to classify the cells on a subject assay plate. Furthermore, depending upon the nature of the support or treatment on the support which is chosen, cells of different types may adhere to the assay plate with differing affinities. Thus, depending upon the cells to be studied and the nature of the support or coatings, a standard cytometric method may be employed on a sample first and then the assay plate and method of the present invention may be employed on the same or a substantially similar sample to calibrate the system.

For acquisition of images, the camera's exposure time may be separately adjusted. If the cells are labeled with fluorescent dye, the exposure time is adjusted for each dye to ensure a high-quality image from each channel. Software procedures can be called, at the user's option, to correct for registration shifts between wavelengths by accounting for linear (X and Y) shifts between wavelengths before making any further measurements. The electronic shutter of the camera is controlled so that sample photo-bleaching is kept to a minimum. Background shading and uneven illumination can also be corrected by the software using algorithms known in the art.

Figure 31:
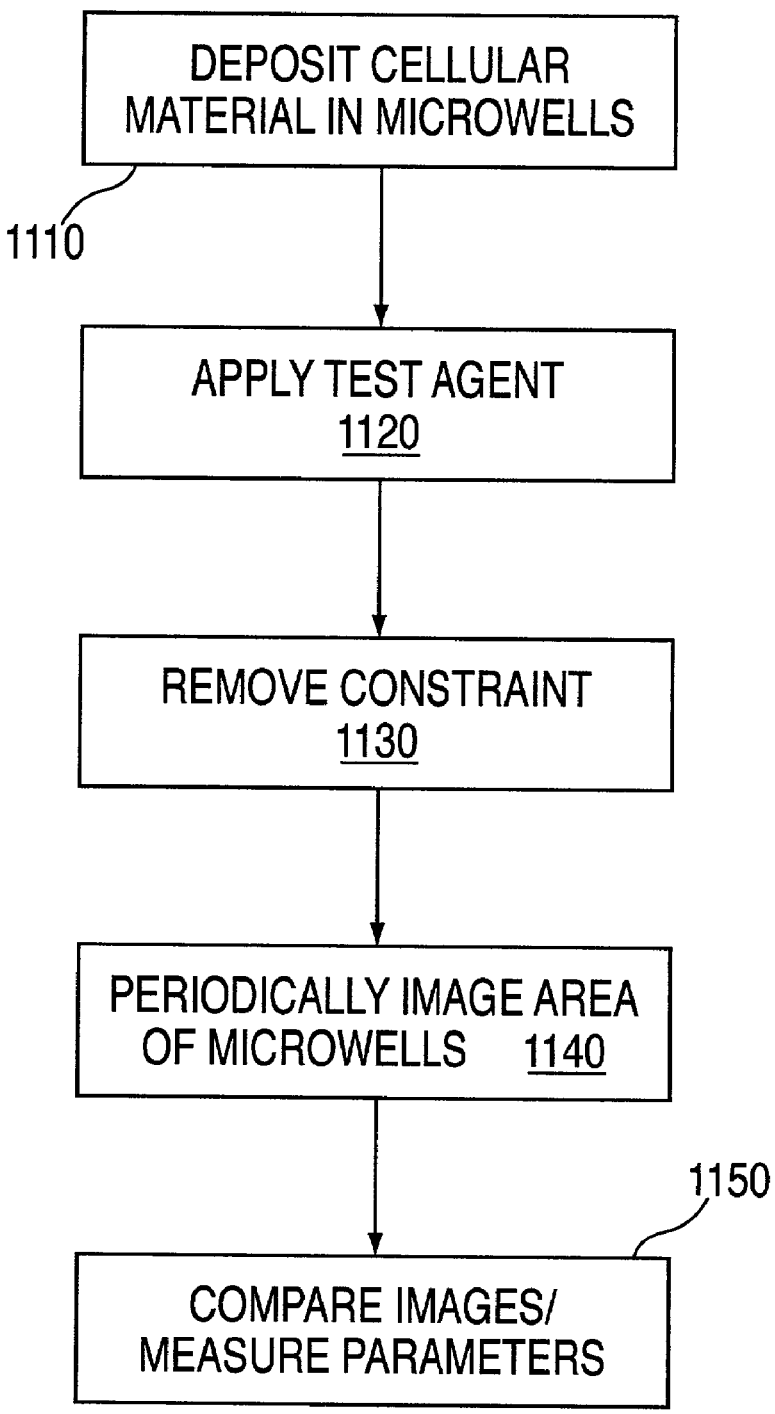
FIG. 31 illustrates a flow chart of a assay according to an embodiment of the present invention.
Figure 32:
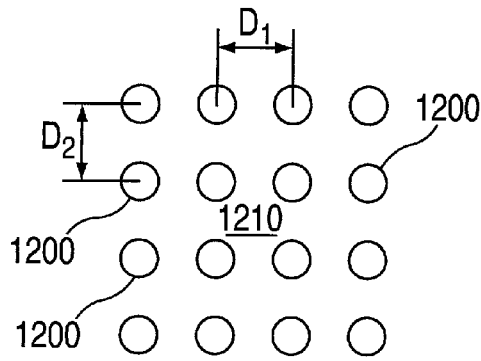
FIG. 32 illustrates exemplary test apparatus according to an embodiment of the present invention.

FIG. 31 illustrates a method 1100 for testing cellular material according to an embodiment of the present invention. According to the method, cellular material may be provided in a test bed that initially defines a constraint that imposes physical limitations to migration and growth of the material (block 1110). A testing agent may be applied to the cellular material and the constraint may be removed (blocks 1120, 1130). Thereafter, the cellular material may be imaged periodically (block 1140). Resultant image data may be compared over time to measure parameters to be-captured under test (block 1150).The parameters, as noted, may include cellular growth, cellular multiplication or cellular migration under influence of the reactant.

For example, cells may be patterned through micro-orifices, such as micro-orifices 1300, of the first layer 1150. The cells are allowed to attach to the support 1140 and grow to confluence. The walls of the micro-orifice 1300 constrain the cell(s) and the cells take on the shape of the micro-orifice 1300, e.g. circular. A test agent is applied through the micro-orifices 1300 and is allowed to contact the cells. The first layer 1150 is removed and the cells are observed Embodiments of the present invention provide image acquisition and analysis processing for use in connection with the foregoing method and apparatus. During one or more stages of testing, imaging apparatus may capture image data of the test apparatus and cellular material therein. As noted the captured image data may represent fluorescent cellular material, stained nuclear material or both among other image content contributed by background objects or noise. Image processing stages may analyze the contents of the captured image data to identify groups of cells, also referred to as "islands," within the test apparatus. From the identified islands, multiple measurements may be calculated to evaluate parameters such as movement (cell motility), reproduction or multiplication (cell proliferation), growth (cell spreading), shrinking or decrease in size (cell rounding), or cell death.

According to an embodiment of the present invention, acquisition of islands from within image data may occur according to a coarse acquisition stage and a fine acquisition stage. The image acquisition phase attempts to identify islands and individual cells within an island throughout the test apparatus.

Figure 34:
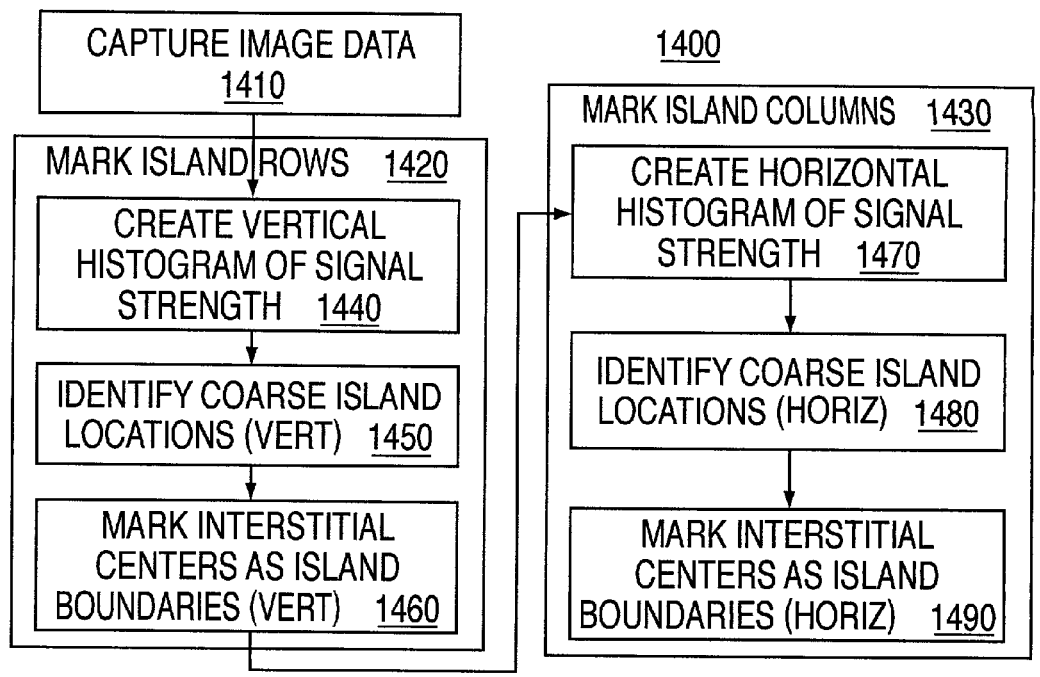
FIG. 34 illustrates a method of performing island acquisition according to an embodiment of the present invention.

FIG. 34 illustrates a method 1400 of performing coarse island acquisition according to an embodiment of the present invention. The method may begin from captured image data (block 1410) in which the micro-orifices 1210 are oriented with respect to horizontal and vertical axes of the image data. From the image data, the method 1400 may attempt to identify island rows and columns of micro-orifices at a coarse granularity (blocks 1420, 1430). Identification of island rows may occur by creating a histogram of image data energy along a first axis of the image data (say, a vertical axis) (block 1440). From the histogram, coarse island locations may be identified (block 1450) and island boundaries may be marked between the islands (block 1460).

Figure 35:
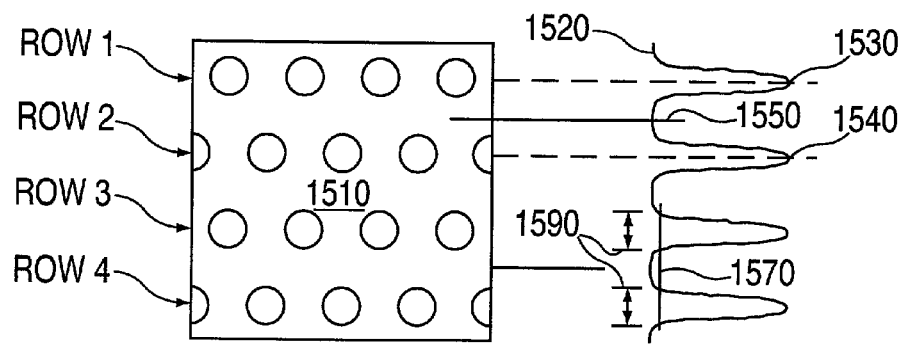
FIG. 35 illustrates idealized, exemplary image data for use in an embodiment of the present invention.

FIG. 35 illustrates exemplary image data 1510 (created within the constraints of the draftsperson's graphics application) and a histogram 1520 that may be created therefrom. FIG. 35 illustrates two alternate approaches to the identification of island locations. In the first approach, shown with reference to rows 1 and 2 of micro-orifices, island centers may be identified from relative maxima 1530, 1540 of the histogram. The maxima 1530, 1540 may be taken as coinciding with the center of respective rows of micro-orifices. Island boundaries 1550, 1560 may be taken as the midpoints between these calculated row centers. Alternatively, when it is known, for example, that micro-orifices occur with a predetermined spatial distance between rows, row centers may be generated from a calculation that considers both the histogram maxima 1530, 1540 and the predetermined row spacing, such as a least squares fit FIG. 35 illustrates a second approach for detecting island positions from the histogram 1520 in connection with rows 3 and 4 of the image data. In this approach, coarse island locations may be generated from a threshold-tested histogram 1520. A predetermined energy threshold 1570 may be applied to the histogram and all vertical regions for which the histogram exceeds the threshold may be assigned to respective islands. A midpoint 1580 between adjacent region boundaries 1590 may be taken as a dividing line between rows of islands. Again, where predetermined geometric relationships between the micro-orifices are known, such as micro-orifice spacing, midpoint 1580 information may be integrated into a larger calculus with the geometric information to identify island locations.

Returning to FIG. 34, the method 1400 may identify island columns from the image data as well (block 1430). From a set of image data, the method 1400 may create another histogram of signal strength, taken along another axis of the image data (say, a horizontal axis) (block 1470). The method may identify coarse island locations from the histogram (block 1480) and, thereafter, mark island boundaries to be between the island locations (block 1490).

Figure 33:
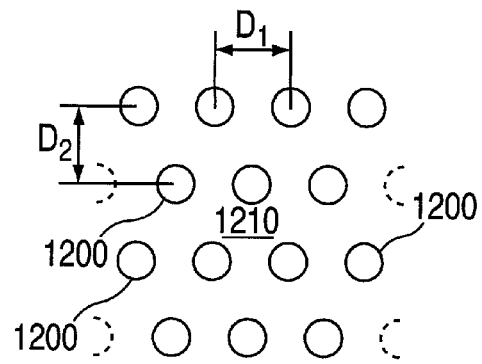
FIG. 33 illustrates exemplary test apparatus according to another embodiment of the present invention.
Figure 36:
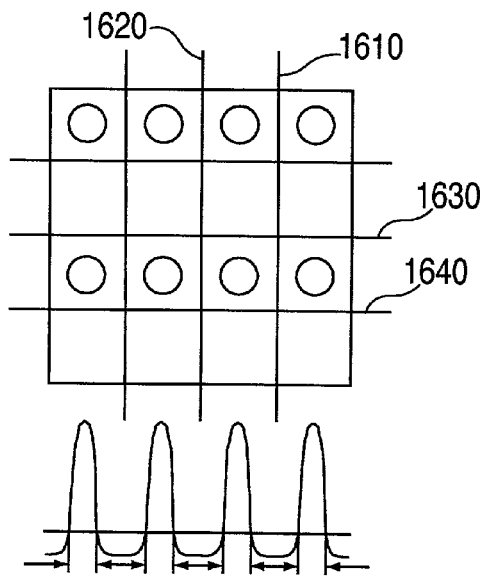
FIG. 36 illustrates idealized, exemplary image data for use in an embodiment of the present invention.
Figure 37:
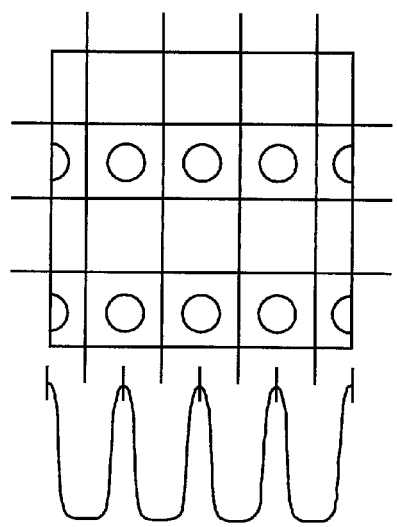
FIG. 37 illustrates idealized, exemplary image data for use in an embodiment of the present invention.

FIGS. 36 and 37 illustrate operation of the column identification performed with respect to the exemplary image data of FIG. 35. In certain embodiments, it may be expected that individual islands will not coincide with each other in predetermined columns. Thus, where micro-orifices are deployed according to a staggered layout, such as that shown in FIG. 33, or some other layout, it may be appropriate to perform the column identification individually on subsets of image data rather than the entirety of the image data. Thus, FIGS. 36 and 37 illustrate operation of the column identification performed respectively on odd numbered and even numbered rows of the captured image data. FIG. 36 illustrates operation of the column identification process with threshold-testing of the histogram defines island regions. FIG. 37 illustrates operation of the column identification where histogram maxima are used to identify column centers. These operations may be performed in a manner that is similar to the row identification described above.

The row and column identification processes 1420, 1430 generate dividing lines between respective rows and columns of islands in the image data. These dividing lines may be used to identify boxes that define a boundary (herein, "bounding boxes") for each island of cells in the captured image data. Shown with respect to FIG. 36, dividing lines 1610, 1620, 1630 and 1640 define a bounding box for an island 1650 of cells. Captured image data of each bounding box may be further analyzed in a fine analysis process, described below.

The foregoing processing may be performed on captured image data of almost any format. Conventionally, image data occurs as black-and-white image data, grayscale image data or color image data. In the case of black-and-white image data, typically each pixel is assigned a single bit value (either 0 or 1). Grayscale image data typically represents each pixel by a multi-bit value, such as an eight bit value which would permit 256 quantization levels to be assigned to each pixel. In either of the foregoing cases, the histograms described above may be created simply by summing the pixel values along each axis. For example, if a histogram is to be created along a vertical axis of the image data, the summing may occur along each pixel row to generate a histogram value at a corresponding position along the vertical axis.

Color image data typically includes separate values for each color component at each pixel. Thus, a pixel may-have a red color component, a green-color component and a blue color component. An alternative color system may represent image information as a luminance color component and a pair of chrominance color components. Histograms may be generated by summing a predetermined one of the color components, by summing all of the color components or by calculating an "energy value" of each pixel from the components and summing the calculated energy values.

Figure 38:
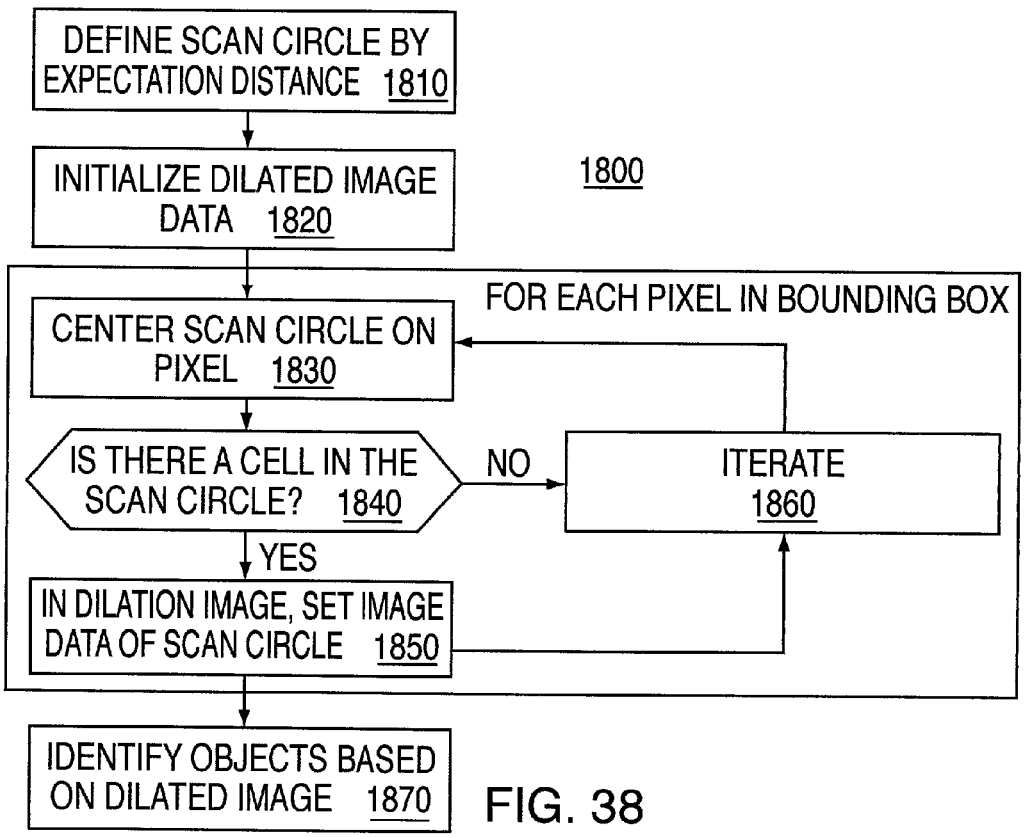
FIG. 38 illustrates a method of identifying islands according to an embodiment of the present invention.

A fine island identification process may follow the coarse identification process described above. FIG. 38 illustrates a method 1800 of identifying islands from image data of bounding boxes, such as the bounding boxes described from the foregoing embodiments. The method 1800 may begin by defining a dilation kernel dimensioned according to a predetermined expectation distance (box 1810). The expectation distance may be an arbitrary distance chosen by an operator and is related to the size of the identified island. The operator may alter the expectation distance at any time to achieve a larger or smaller identified island as desired. For example, the expectation distance may define the radius or diameter of the dilation kernel. The method 1800 also may initialize data of a "dilated image" (box 1820). Thereafter, the method may consider each pixel in the bounding box. For each pixel, the method considers the captured image data that falls within a dilation kernel centered at the current pixel (box 1830). If the image data of the dilation kernel indicates that cellular material is represented therein, the method 1800 may set pixels occupied by the dilation kernel in the dilated image data (boxes 1840, 1850). Thereafter or if the image data indicates that no cellular material is represented therein, the method may advance to the next pixel (box 1860).

The method 1800 generates a second image from the captured data, a dilated image. Once all pixels have been considered, the resulting image, referred to as the dilated image, may contain one or more dilated islands.

According to an embodiment, the methods of FIGS. 34 and 38 may be applied serially to captured image data to provide both coarse and fine island acquisition. Of course, other implementations are possible. In the circumstance where an image represents a test to be run on a single micro-orifice, it would not be necessary to perform the method of FIG. 34 to identify-bounding boxes of coarse locations of islands.

In an embodiment, it is not necessary for the method to iterate over every pixel of a bounding box. The method may consider pixels having predetermined spacing from each other (e.g., every other pixel, every third pixel, etc.) in each direction. The method need not consider pixels on the outer boundaries of the bounding boxes over which it traverses.

The foregoing description of the island acquisition method 1800 introduces the concept of an expectation distance. Generally, the expectation distance is related to a maximum expected distance of separation that may occur between any two pairs of cells for which it is appropriate to consider the cells as part of the same "island." Typically, the expectation distance may be derived from the biological test to be run and may depend on cell types, number of cells, amount and type of test agents and other factors that are known to influence the biological properties being measured. Therefore, it may be set on a case-by-case basis.

As in the foregoing methods, the method of FIG. 38 finds application with various types of image data and may be used with varying levels of sensitivity. For example, in black-and-white data, white pixels (those having values of 1) may represent the presence of cellular material. Thus, the determination of whether dilation kernel data represents cellular material may be answered affirmatively if even a single pixel had a value of one. Similarly, in grayscale data, cellular material may be identified for a pixel having a predetermined value (say, half scale or greater—a value of 127 in an 8 bit word). Again, if the value of any pixel exceeds the threshold value, the method would be permitted to indicate that cellular material is present therein. For color image data, similar calculations may be made. Since cellular material fluoresces at a predetermined wavelength, it may be possible to examine only predetermined color components of the image data to determine if cellular material is present in a dilation kernel.

Figure 39:
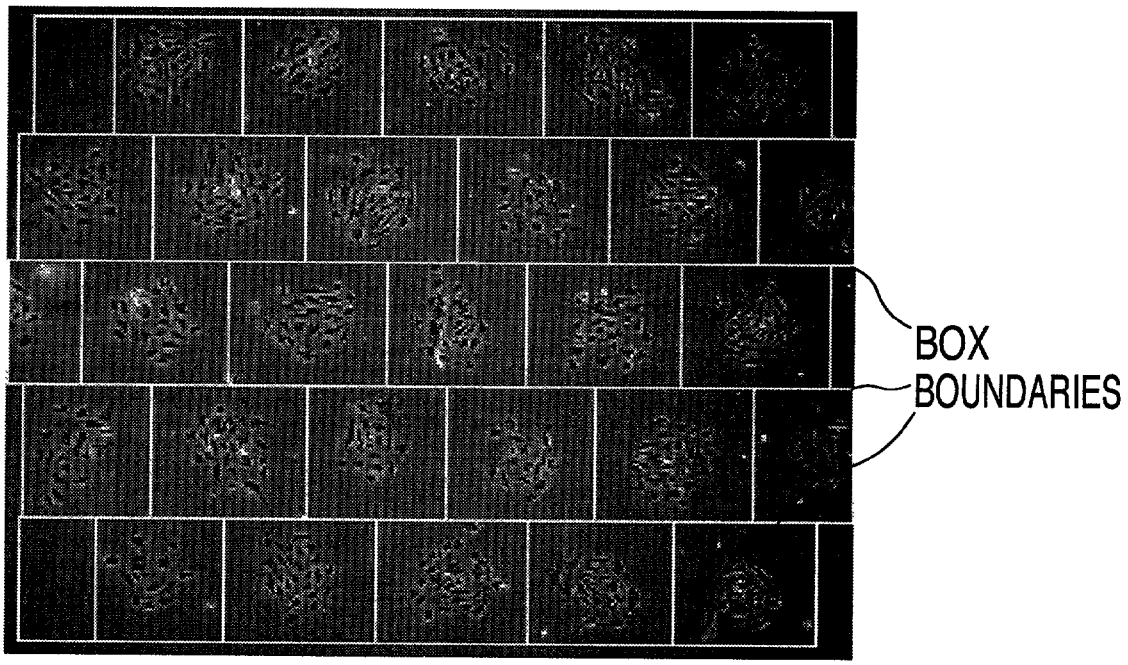
FIG. 39 is a screen shot of exemplary source image data.
Figure 40:
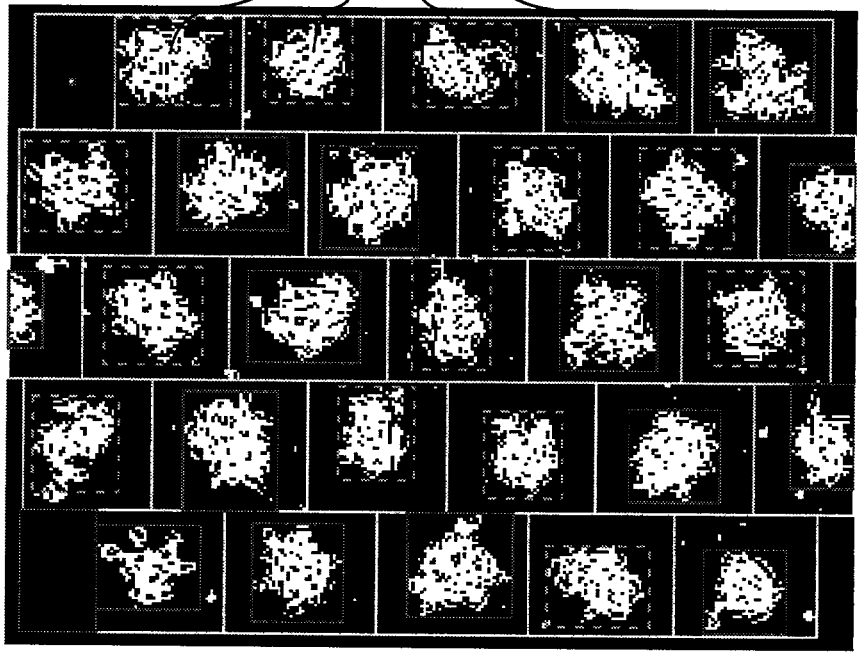
FIG. 40 is a screen shot of exemplary dilated image data.

FIGS. 35–37 illustrate operation of the image processing methods upon idealized data in which cellular material is confined to the micro-orifices. While such presentation is useful to explain operation of the methods, the methods are most useful when applied to image data that captures cellular migration, spreading, proliferation, rounding, or death. FIGS. 39 and 40 are screen shots illustrating operation of the foregoing methods upon image data in which cellular material has been permitted to migrate without limitation. FIG. 39 illustrates exemplary source data and bounding boxes identified from operation of the method 1400 of FIG. 34. FIG. 40 illustrates exemplary dilated image data developed from the source image data of FIG. 39. FIG. 40 also illustrates island that may have been recognized from the source image data. They are circumscribed by bounding boxes of their own.

Having identified islands of cellular material, the image acquisition process may generate several independent measurements of the islands that may provide statistically useful biological information, and more preferably, information related to one or more of cell motility, cell growth, cell proliferation, cell rounding or cell death.

Additionally, where more than one cell type is deposited in the micro-orifice, the measurements may be calculated based on one type of cell within a population of mixed cell types rather than on the entire population of cells. These measurements may be calculated for each type of cell within the micro-orifice and then may be compared to each other to produce relevant biological information.

For example, prior to deposition in the micro-orifice, each cell type may be treated with an appropriate label, tag, stain, or dye so as to distinguish and identify each cell type within the same micro-orifice.

Such information may include, for example:
Pixelated cellular area;
Dilated cellular area;
Vertical and horizontal lengths;
Average minimum distance between cells;
Average distance between cells;
First polar moment of inertia taken about the island centroid;
Second polar moment of inertia taken about the island centroid; and
First and/or second polar moments of inertia taken about the island centroid, normalized to cellular area.

Each Measurement is Discussed in Turn.

The pixelated cellular area calculus counts from source image data the number of pixels in a given island that represents the presence of cellular material. The dilated cellular area counts from dilated image data the number of pixels in a dilated island that represents the presence of cellular material. The vertical and horizontal lengths calculus respectively represents the height and width of a bounding box that surrounds an island or dilated island of cellular material; these dimensions may be taken from the source image data or dilated image data of an island as desired.

The method also may capture the average minimum distance between cells and the average distance between cells. For these measurements, it may be useful to identify cell nuclei and compute distances between them. For example, cells may have a nuclear staining agent applied to them in, addition to a fluorescing agent. Captured image data then may capture not only the cytoplasm as a fluorescent material but they also may captured cell nuclei as a predetermined color that may be distinguishable from the fluorescence within the image. It may be useful to capture two images of the cells, a first image to capture the fluorescent material and a second image to capture the cell nuclei. In either embodiment, cell nuclei may be identified and distinguished from other artifacts within a captured image.

The distance parameters may consider the positions of various cell nuclei in a given island. To compute the average distance between cells within a given population of cells, the distances between the nuclei of each pair of cells within the population are summed and the sum then divided by the number of unique pairs in the population. The image may contain different populations of cells which may include the population of cells defined by a single island within a bounding box, the population of cells defined by two or more islands within a bounding box or the population of cells defined by the bounding box.

The average minimum distance between cells also considers the distance between a given cell and all others in an island. The minimum of these distances is logged. The process may repeat for all other cells in an island until a set of minimum distances is identified, one for each cell. Thereafter, these minimum distance values may be averaged to determine the average minimum distance between cells.

The first polar moment of inertia considers an island's centroid and the distance of cellular material from this centroid. It involves a computation of the island centroid and a measurement of each pixel representing cellular material from this centroid. Thereafter, one integrates the sums of vector distances from the centroid to each of these pixels and multiplies by the area of the island squared.

The second polar moment of inertia also involves a computation of the island's centroid and a measurement of each pixel representing cellular material from this centroid. Thereafter, an integration of the sums of the squares of the vector distances from the centroid to each pixel may be applied.

Either the first or second polar moment of inertia calculations may be made from the source image data or dilated image data of an island.

Additionally, calculations of the first or second polar moments of inertia may be normalized to the island's area. If the source image data is used for the polar moment of inertia calculations, then naturally the island's source image area can be used for normalization. Similarly, if the dilated image data is used for the inertia calculations, the island's dilated image area can be used for normalization.

The foregoing measurements may, alone or in conjunction with at least one other measurement, provide biologically relevant information, and more preferably, information related to cell motility, cell growth, cell proliferation, cell rounding, or cell death.

For example, an increase in pixelated cell area may be indicative of cell spreading and/or cell proliferation. As another example, a decrease in pixelated cell area may be indicative of cell rounding or cell death.

An increase in dilated cell area may indicate one or more of cell proliferation, cell spreading or cell motility. A decrease in dilated cell area may indicate cell rounding or cell death.

A change in the horizontal or vertical lengths of the bounding box or change in the average distance between cells or a change in the average minimum distance between cells may indicate one or more of cell motility, cell proliferation, cell spreading, cell rounding or cell death.

The relative levels of each of these (e.g., cell spreading, cell rounding, etc.) can be measured more easily by combining cytoplasmic and nuclear stains. For example, when the cells are stained with a nuclear stain, individual cell nuclei may be distinguished from other cell nuclei within a population of cells, thus allowing the number of detected nuclei to be summed. The number of detected nuclei may directly correlate to the number of cells in a population. When quantified at different time points, the change in the number of cell nuclei detected over time may be calculated, which may directly correlate to the change in the number of cells in a population over time. A nuclear stain used in conjunction with a cytoplasmic stain may possibly elucidate the cause of a change in an aforementioned measurement. For example, it may be determined that there is no change in the number of cell nuclei detected and thus, no change in the number of cells in a population over time. One may conclude that a change in a measurement (e.g., pixelated cell area) is due primarily or wholly to a parameter other than cell proliferation or cell death.

After a scan of a plate is complete, images and data can be reviewed with the system's image review, data review, and summary review facilities. All images, data, and settings from a scan are archived in the system's database for later review. Users can review the images of the area of the plate analyzed by the system with an interactive image review procedure. The digital images produced by the camera are stored in the computer.

Figure 41:
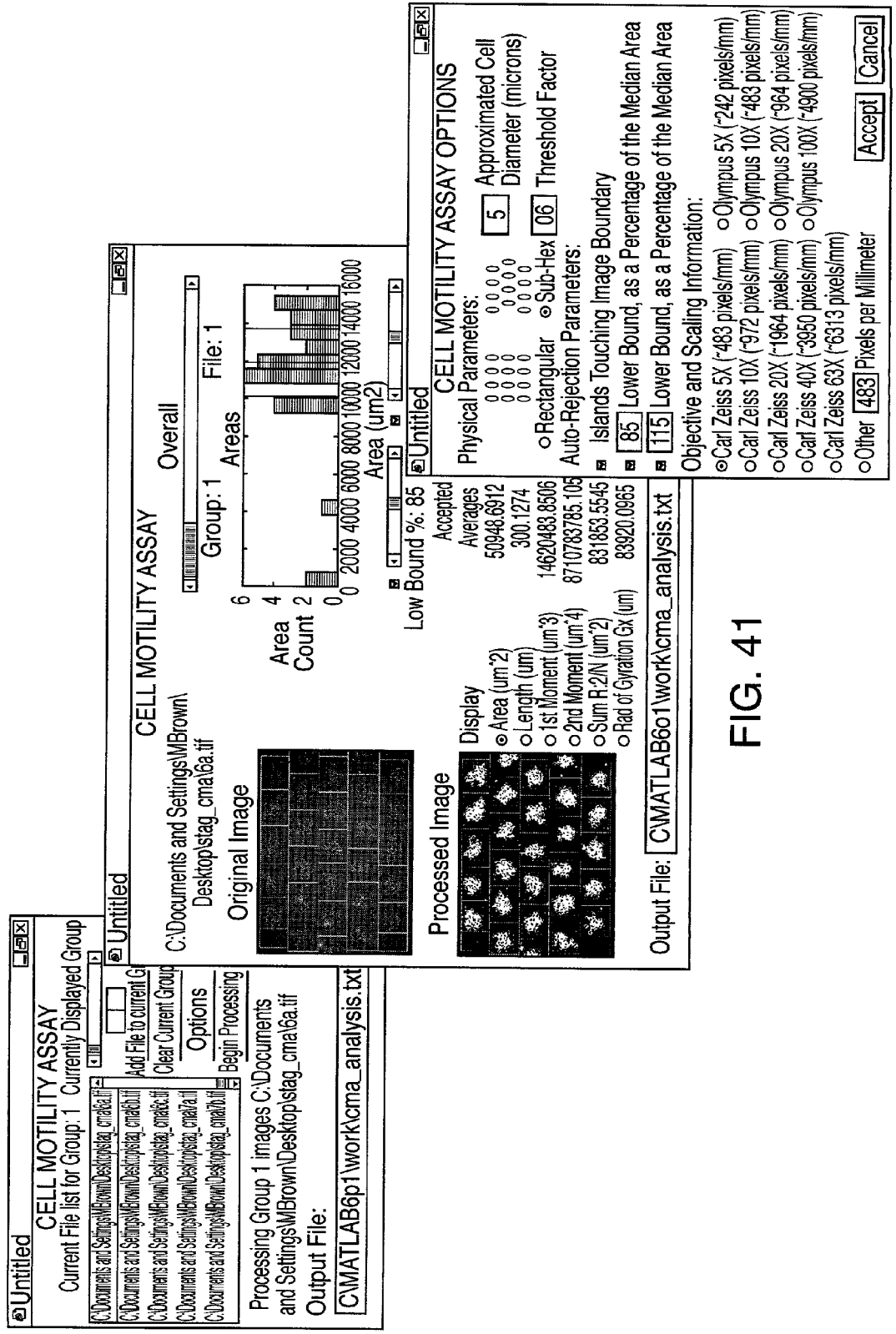
FIG. 41 depicts various images of data and digital images retrieved from an assay according to an embodiment of the present invention. Algorithms are used to convert digital images into computer readable data that is then converted into usable graphic interfaces.

The user can review data using a combination of interactive graphs, a data spreadsheet of features measured, and images of the area of the assay plate of interest with the interactive data review procedure. See FIG. 41. Graphical plotting capabilities are provided in which data can be analyzed via interactive graphs such as histograms and scatter plots. Users can review summary data that are accumulated and summarized for all cells within each micro-region with an interactive micro-region-by-micro-region. Hard copies of graphs and images can be printed on a wide range of standard printers. All images and data may be stored in the system's database for archival and retrieval or for interface with a network laboratory management information system. Data can also be exported to other third-party statistical packages to tabulate results and generate other reports.

As a final phase of a complete scan, reports can be generated on one or more statistics of features measured. Multiple reports can be generated on many statistics and be printed. Reports can be previewed for placement and data before being printed.

EXAMPLES

Example 1

Procedure for Cell Migration Allay Plate Fabrication

A topographically patterned master having a plurality of posts is prepared from a photolithographic mask. These posts are elevated approximately 100 µm above the background. In one embodiment, the pattern is made up of 24 micro-regions, each containing a circular array of 200 µm posts spaced on a 500 µm center. Alternately, instead of having discrete regions of posts, the entire surface of the master may contain posts. In one preferred embodiment, the master is made of photoresist patterned on a 150 mm silicon wafer. To prepare this master, SU-850n photoresist spun at 1300 rpm was used and processed according to the supplier's specifications.

A two-component poly(dimethylsiloxane) (PDMS) prepolymer (Gelest Optical Encapsulant 41) was mixed and degassed under vacuum before it is spun onto the master. This spin coating was done at a speed high enough to produce a polymeric membrane (i.e., the thickness of the resulting PDMS film is less than that of the elevated features on the master). The prepolymer was spun at 2250 rpm for 40 seconds. A rigid frame with the standard microtiter footprint was then placed around the outer perimeter of the membrane. The master/membrane/frame was then placed on a hotplate 109 and the PDMS was cured for seven minutes at 95° C.

After cooling the master to room temperature, a group of 24 rigid plastic rings was "inked" in thin film of liquid PDMS. The rings were then placed around the post arrays on the master and the entire assembly was again heated on a hotplate 100 for two minutes at 95° C.

The final fabrication step involved filling the area between the rings with PDMS to make up the bulk of the device. Here, the PDMS was injected via syringe into the space between the rings. The PDMS "ink" on the rings, which had been partially cured by this point, prevented leakage of PDMS into the membrane regions. The master was again placed on 95° C. hotplate 100 and the PDMS was cured for 30 minutes.

To remove the cured device from the master, the top surface was first covered with a thin layer of ethanol, which quickly wetted the PDMS. A dull knife was used to cut the interface between the inside of the frame and the polymer, which allowed the frame to be removed from the master. While the device may be removed with the frame intact (i.e. the frame becomes part of the final device), in this example the frame was used for molding purposes only.

The device was then covered again with a thin layer of ethanol (to prevent sticking) and manually peeled from the master. Upon removal, the device was rinsed one final time with ethanol before it was dried with nitrogen gas and placed in a 65° C. oven for solvent evaporation. The device was then stored in a polystyrene dish, which can optionally be used as the support for studying cell motility.

Example 2

Patterning of Cells on a Support

In this example, macro-wells of a stencil which is engaged with a the first layer 150 and support are filled with PBS and a vacuum is applied for two minutes to remove air bubbles. The support may then be treated with fibronectin (50 mg/ml) or other extracellular matrix protein for 30 minutes, followed by washing twice with PBS. After aspirating PBS, cells may then be plated in freshly warmed medium at a density of $5–25 \times 10^3$ cells/cm$^2$ (=$1–4 \times 10^4$ cells per macro-well of a 24-well plate 100, in a volume of 300 ml per macro-well; or $5–25 \times 10^4$ cells per 35 mm dish in a volume of 2 ml). The cells deposit through the micro-orifices of the first layer, and attach to the support.

After the cells have attached to the support (30 minutes-2 hours), the cell culture medium in each macro-well is replaced with fresh medium. Cells are left to spread in a 37° C. incubator for two hours to overnight. The cells are washed with PBS and fresh medium containing the treatment of interest is added to the wells. The stencil/first layer is then removed and the effects of the test compound on cell motility; cell-shape or viability are observed.

Example 3

Image Acquisition

Imaging is performed using an inverted microscope equipped with the following: epifluorescence, motorized and programmable stage, autofocus mechanism, and CCD camera. Two to three randomly selected areas per macro-well are imaged. The stage translated from one macro-well to another, and images were focused using automatic focus (Z axis). Images were captured in either phase contrast or epifluorescence.

Acquired images shared a common file name, but different suffix corresponding to the macro-well number and position. For example, an experiment called TEST with 24 wells generated TEST01-TEST24 when one image per macro-well was taken. Images were generated prior to application of a test compound or other external stimulus, and at various times after treatment.

Example 4

Data Analysis

Automated data analysis was performed using software that processed information in the following order: a) recall of files in consecutive order; b) identify cells (using various methods such as thresholding, erosion, and gradient contrasting; c) define cells in a cluster using a clustering algorithm; d) measure relevant parameters. Some of the relevant parameters are based on cellular clusters or micro-regions: average values of perimeter, diameter, surface area, percentage of cell coverage per unit area, perimeter to surface area ratio, and other parameters. The data analysis is capable of correlating any or all these parameters with cell motility. The final data set may be based on normalized average of multiple parameters or one specific parameter based on biological observation.

Example 5

3T3/Taxol

Macro-wells orifices of a stencil engaged with a support were filled with PBS and a vacuum was applied for two minutes to remove air bubbles. NIH-3T3 fibroblast cells (prelabeled with green cell tracker, CMFDA, Molecular Probes) were collected in DMEM/10% bovine calf serum and plated in the macro-wells at a concentration of $2 \times 10^4$ cells/cm2. After one hour, unadhered cells were washed off with fresh medium. After an overnight incubation, fresh medium containing increasing dosages of paclitaxel (Sigma, 0.1–10 mg/ml) was added to the wells and the stencil was peeled off. Control cells were left untreated. Images of migrating cells were taken at time points, from 0–24 h.

Example 6

Farnesyl Transferase Inhibition in MS1 AND SVR

The qualitative cell migration assay plates of the present invention are useful in the study of biological pathways, such as the RAS pathway, for example. The assays allow for the study of various metabolic pathways and allows for analysis of the effect(s) of agents or biological entities such as inhibitors of cell migration and/or motility on cell motility or cell shape. RAS (a guanine nucleotide binding protein) plays a pivotal role in the control of both normal and transformed cell growth. Following stimulation by various growth factors and cytokines, RAS activates several downstream effectors, leading to gene transcription and proliferation. In many cancers, including 90% and 50% of pancreatic and colon cancers respectively, ras gene mutations produce a mutated RAS that remains locked in an active state, thereby relaying uncontrolled proliferative signals. Much is known about the RAS pathway including strategies to inhibit it. For example, Farnesyl Transferase inhibitors inhibit RAS targeting the cell membrane since Farnesyl Transferase is believed to assist RAS in membrane localization. Additionally, it is believed that downstream effectors, P13-K and MAPK, can be inhibited, thus in turn inhibit the effect of RAS.

Figure 21:
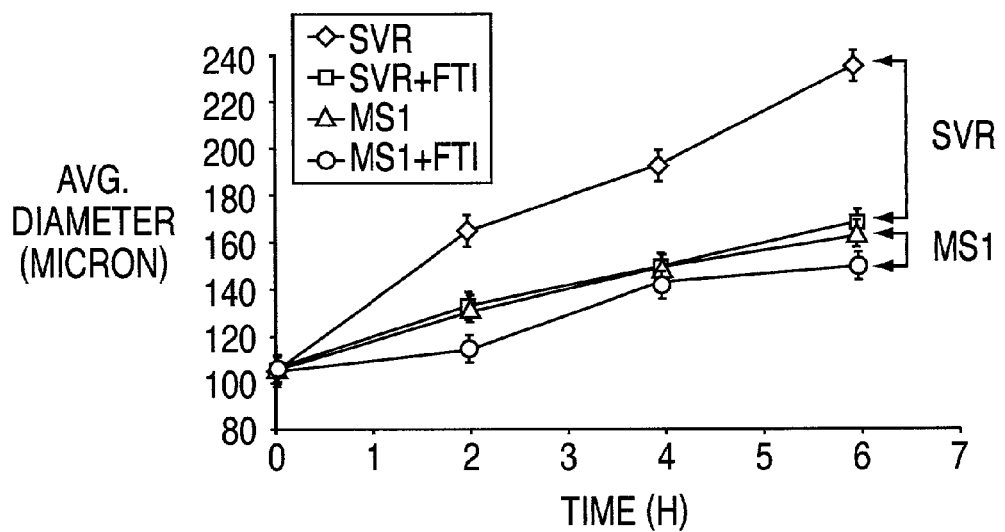
FIG. 21 shows the data analysis of cell motility of MS1 and SVR affected by farnesyl transferase inhibition, in accordance with one embodiment of the present invention.
Figure 22:
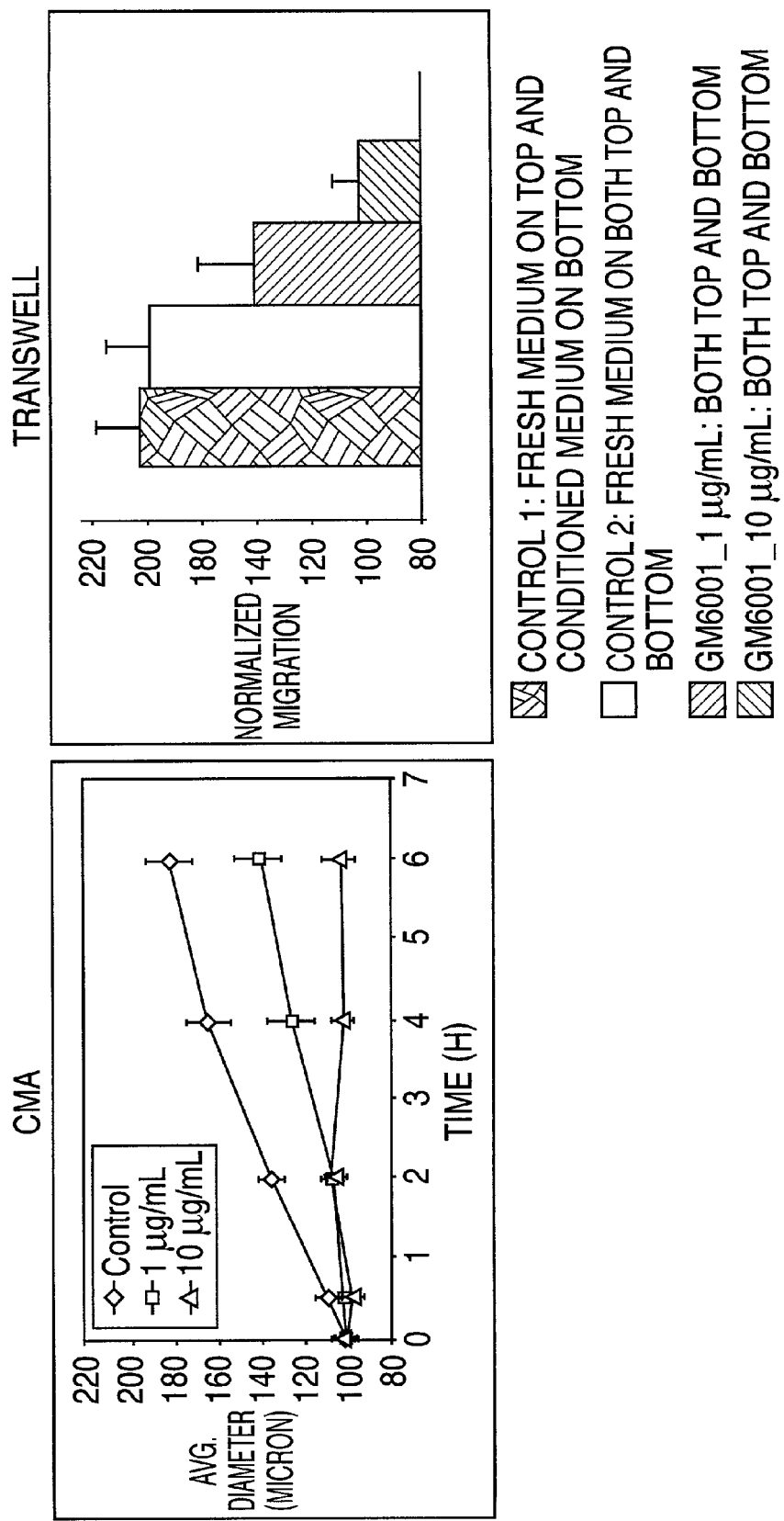
FIG. 22 shows graphs of the results of an assay determining the inhibition of 769-P motility using MMP inhibitor GM6001, and a chart comparing the results of the assay performed in a transwell system and the assay performed in employing the qualitative cell motility assay plate, in accordance with one embodiment of the present invention.

Using standard protocols, MS1 (T antigen-immortalized endothelial cells, ATCC) and SVR (H-ras-overexpressing derivative of MS1, ATCC) were plated into macrowells at densities of $12 \times 10^3$ and $6 \times 10^3$ cells/cm$^2$, respectively, in DMEM/5% fetal bovine serum. Unattached cells were washed off after 1 hour, and the cells were replenished with fresh media. To the media was also added farnesyl transferase inhibitor (FTI-277, Calbiochem) to concentration of 10 mm. Cells were cultured overnight under fresh media in an incubator at 37° C. and 5% $CO_2$. At the start of experiment, the stencil/first layer was removed after first on the support to allow cell migration. At different time points (time zero and time four hours) images were taken and analyzed for effects of FTI-277 on cell motility. FIG. 21 contains the pictorial results of an assay showing farnesyl transferase inhibition in MS1 and SVR cells. The control cells are shown to have migrated further away from their original starting positions than the cells treated with FTI. FIG. 22 graphically depicts the results of the same assay as shown in FIG. 21.

Figure 23:
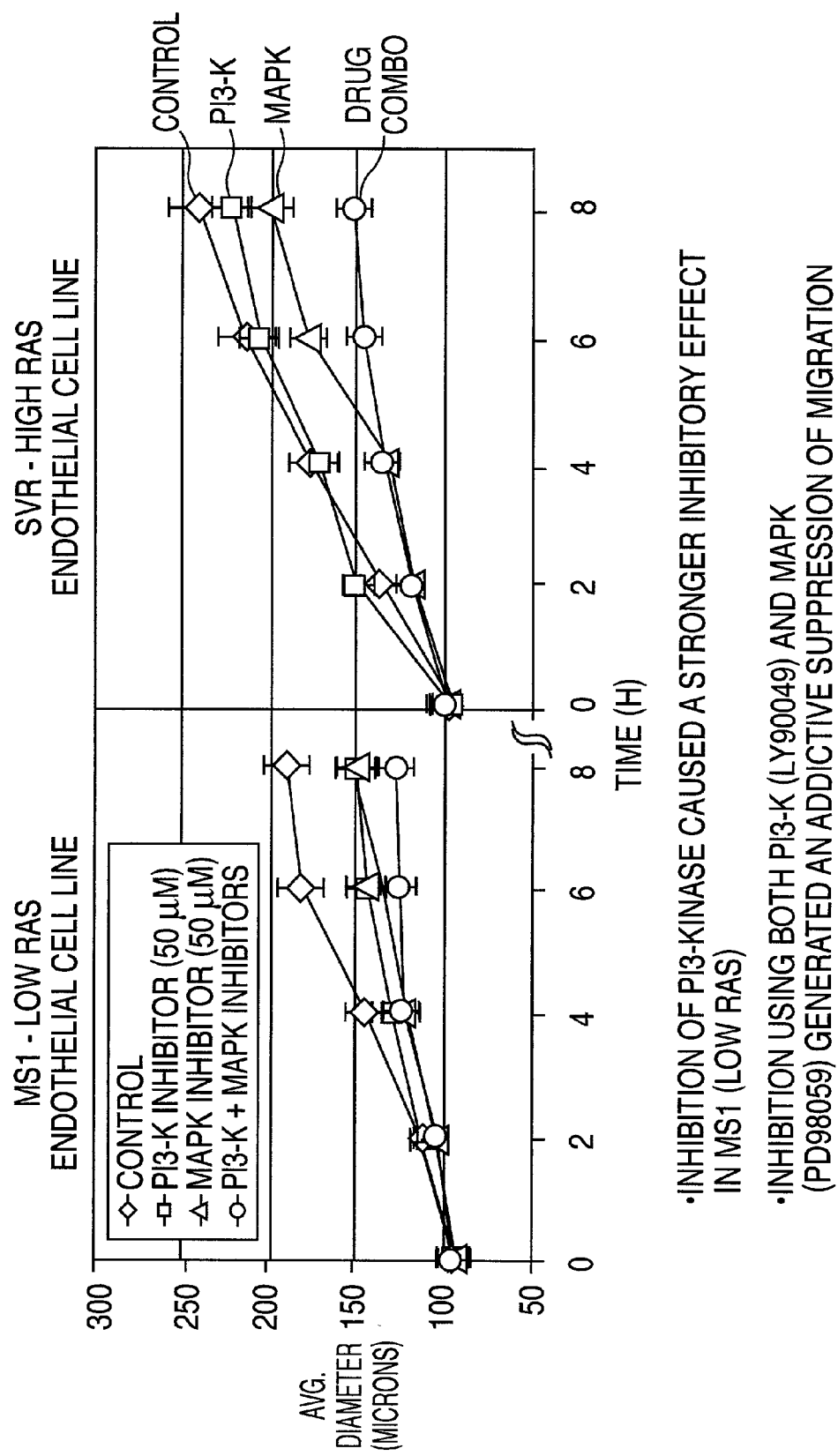
FIG. 23 presents the results of an assay where the effects of several inhibitors in the RAS pathway were measured, in accordance with one embodiment of the present invention.
Figure 24:
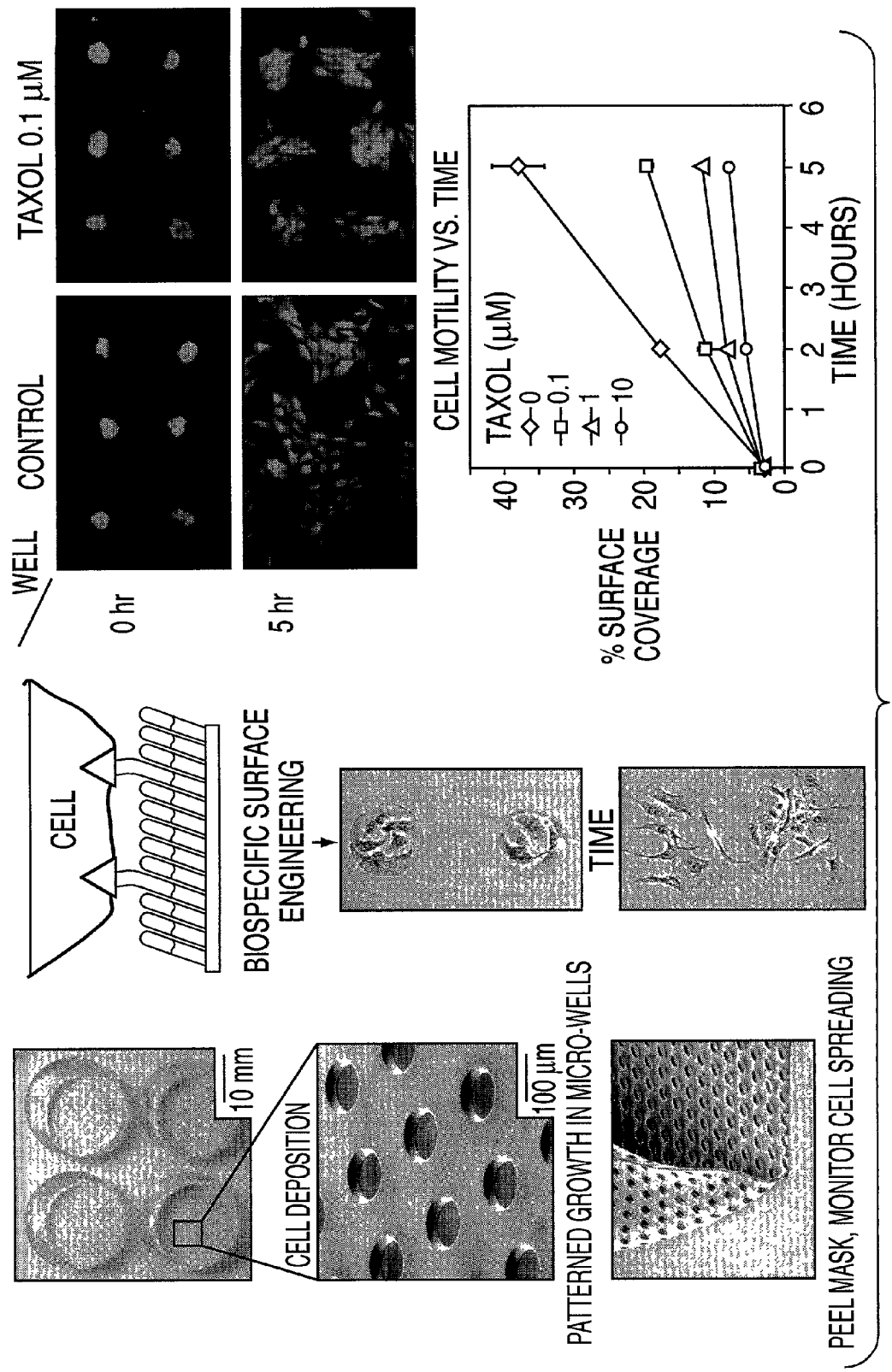
FIG. 24 depicts a cell motility assay wherein cells are patterned in a predetermined area using a physical constraint. The physical constraint is removed and cell motility is monitored. Well defined patterns of cells can be created once the membrane is lifted.
Figure 25B:
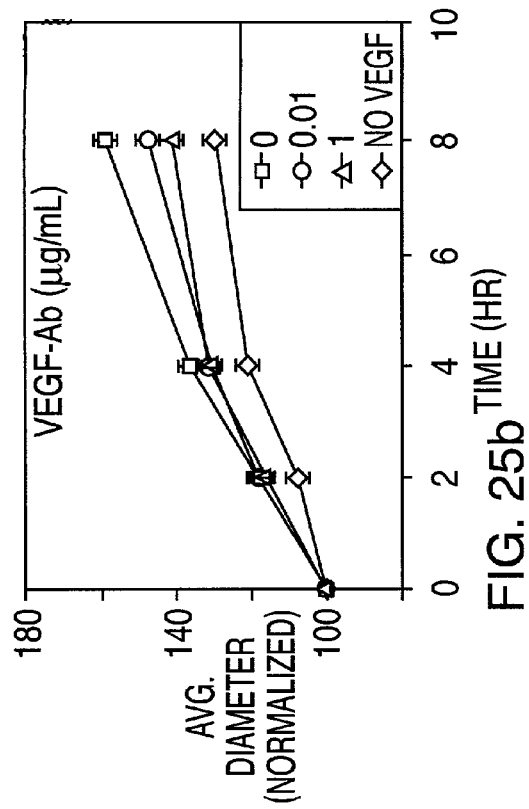
In FIG. 25B, the concentration of VEGF is fixed. An antibody to VEGF is added in various concentrations. The motility of cells is affected in a dose-dependent fashion by the antibody. When an inhibitor to the VEGF receptor is added, the cells migrate at a such slower rate as depicted in FIG. 25C.
Figure 25D:
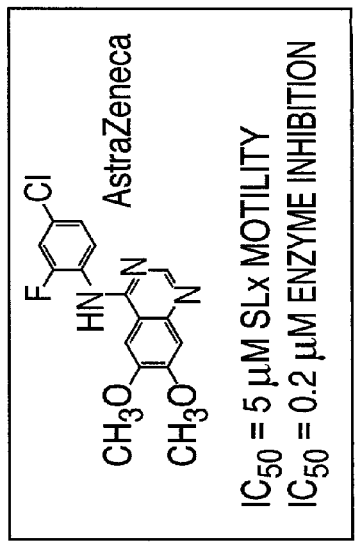
FIG. 25D shows that cell motility can be affected with kinase inhibitors. Normally enzyme inhibition screens involve proteins and their substrates and not cells.
Figure 25A:
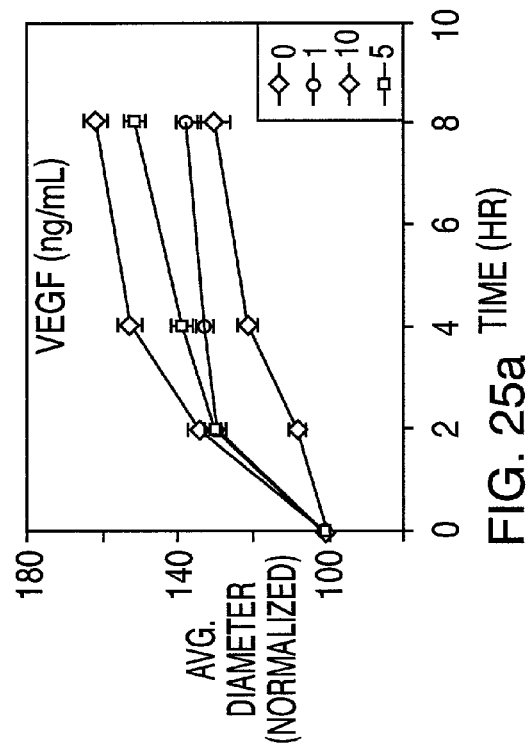
FIG. 25 depicts a particular cell motility assay using endothelial cells and agonists and antagonists of such cells. The results depicted show that cell motility is affected when an inhibitor to VEGF is added. Normally VEGF stimulates cells to migrate as depicted in FIG. 25A.
Figure 25C:
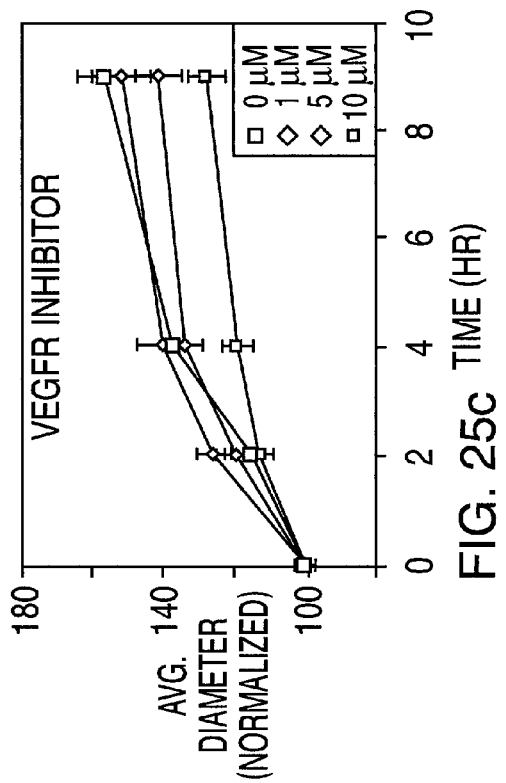
Figure 27:
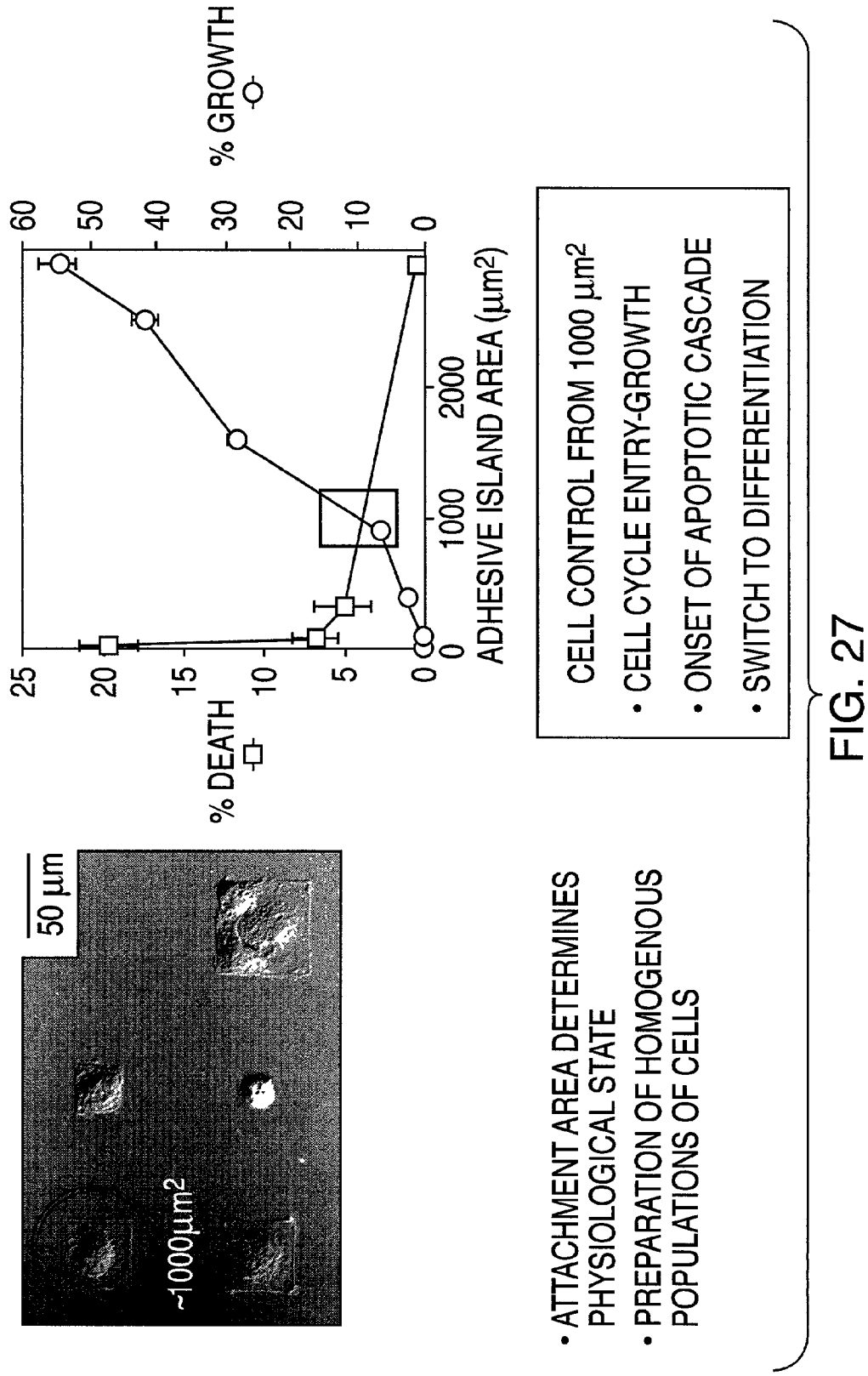
FIG. 27 depicts control of cell cycle by patterning.
Figure 28:
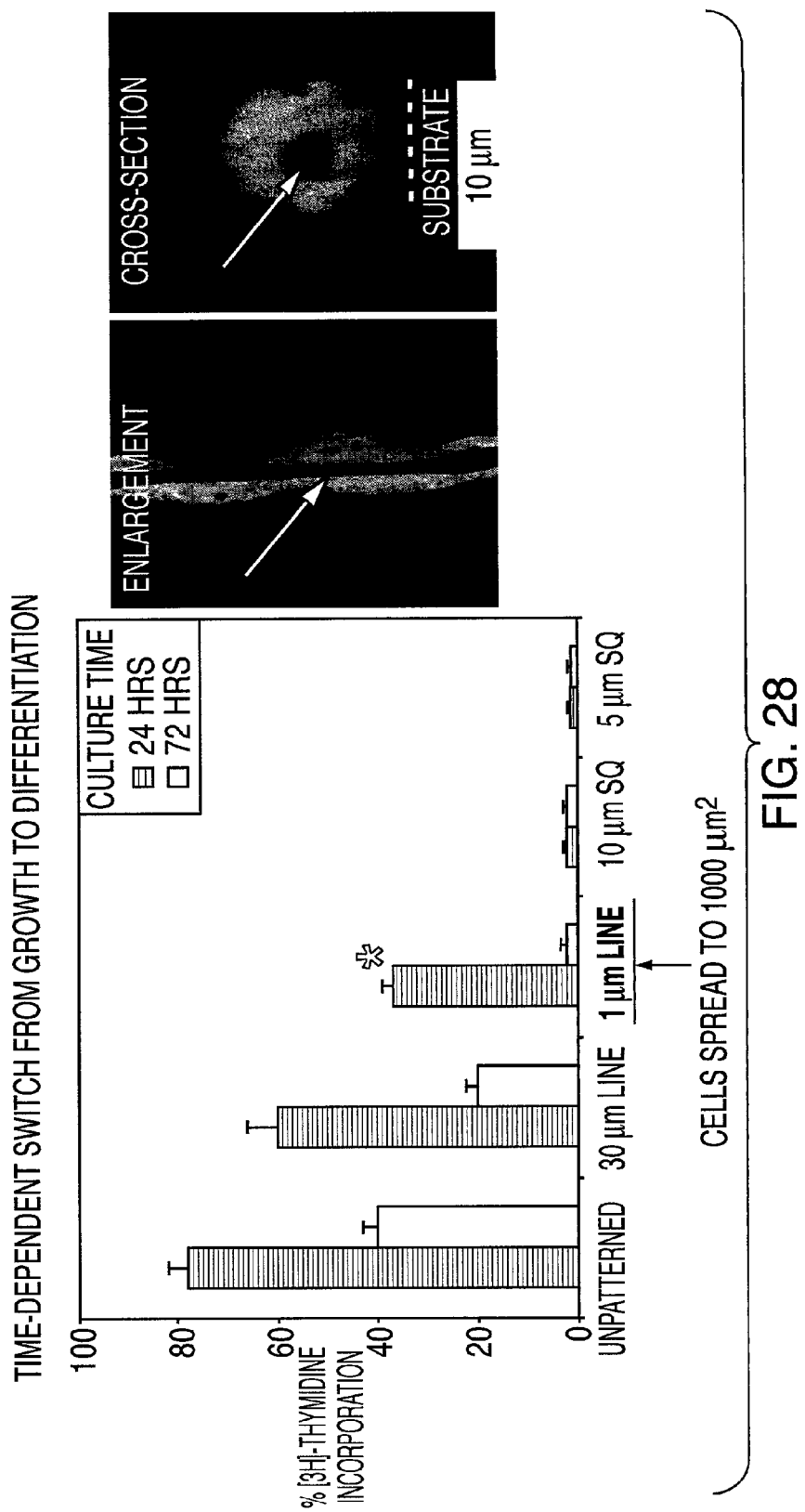
FIG. 28 depicts the effects of cell patterning geometry on cell differentiation.
Figure 29:
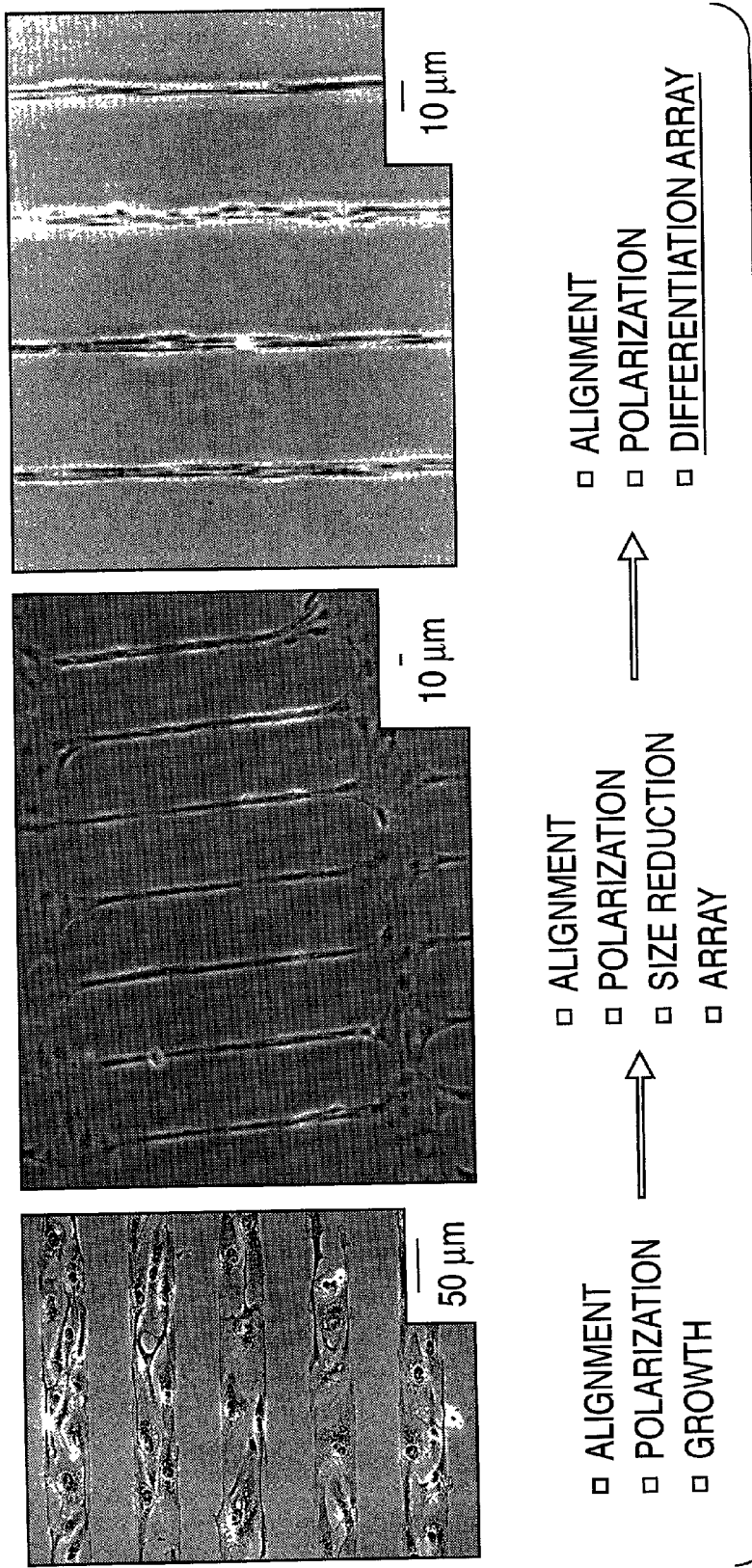
FIG. 29 depicts cell differentiation brought about by patterning of the cells into certain constraints.
Figure 30:
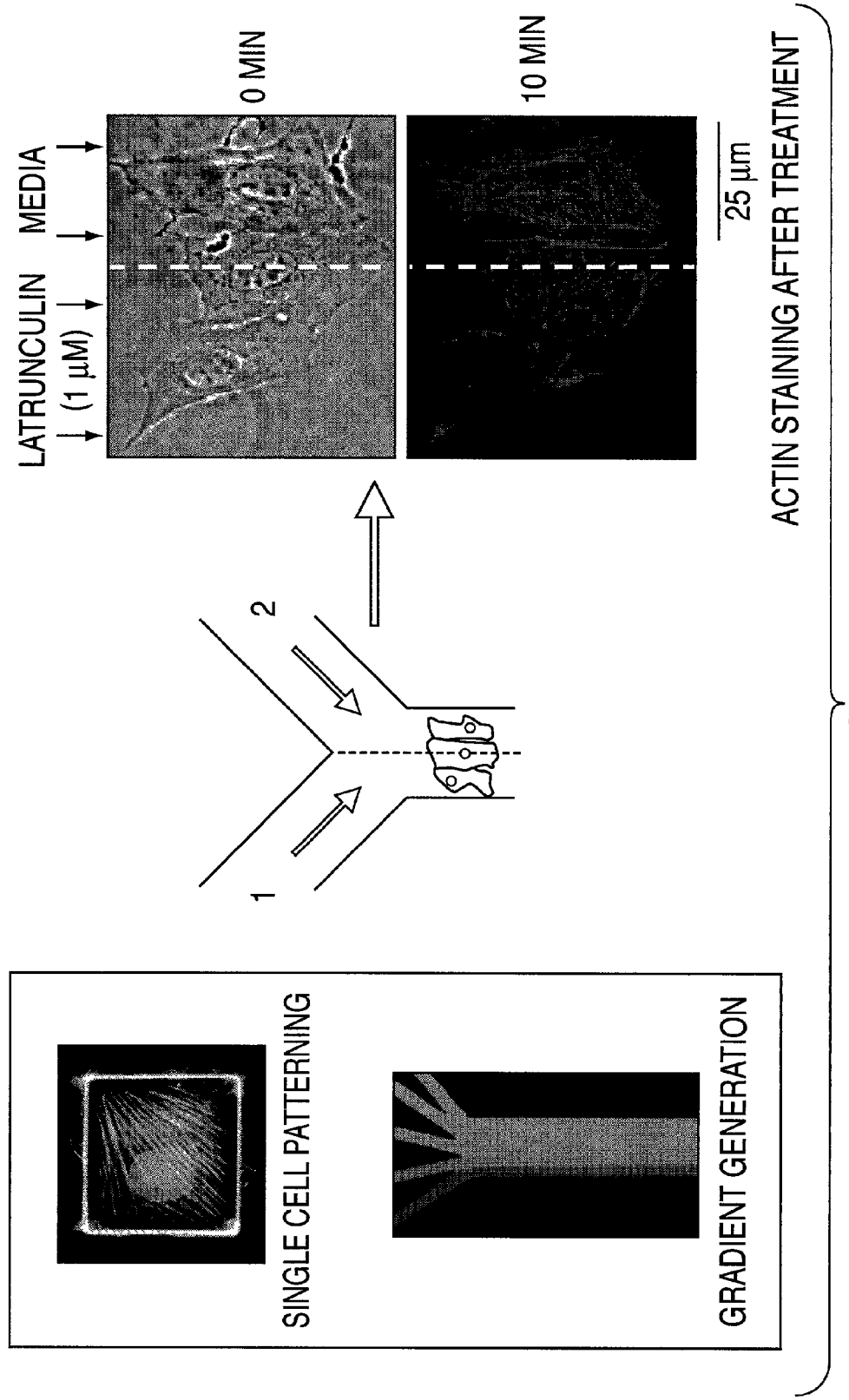
FIG. 30 depicts single cell patterning and the subsequent evaluation of cytoskeletal stability and rearrangement.

FIG. 23 presents the results of an assay where the effects of several inhibitors in the RAS pathway were measured. The graph reveals that the various inhibitors (P13-K, MAPK, and a mixture of both) show an effect on the diameter of the cell islands. Measurements were taken at 0, 2, 4, 6 and 8 hour increments. Over time, the control cells showed a larger increase in diameter over the cells treated with the inhibitors. The graph reveals that the combination therapy had a greater effect on cell motility (the diameter increased less as the cells moved less).

Example 7

Inhibition of Cell Motility of Renal Cells via Matrix Metalloproteinase Inhibition Two renal cell lines were used to study the effect of matrix metalloproteinase (MMP) inhibition on cell motility. Standard protocols were used to plate 100 769-P cells (renal carcinoma, purchased from ATCC) and HK-2 (proximal tubule cells from human kidney, from ATCC) in qualitative cell migration assay plate.

After allowing the cells to attach and spread for 8 hours, the stencil and the first layer were removed and MMP inhibitor (GM6001, Calbiochem) was added at various concentrations. The following data represents that MMP inhibition reduces cell motility of 769-P, but has no effect on the HK-2 cell line. Comparison of a qualitative cell migration assay plate to a conventional motility assay using Becton Dickinsions' transwell (6 well, 8 micron pores) showed that the qualitative cell migration assay plate data correspond to the transwell data. See FIG. 23, which demonstrates that data from CMA showed more sensitive determination of cell motility.

Example 8

Microtubule Experiments

Microtubule formation is necessary for cell movement and cell division. Common cancer drugs such as colchicine, nocodazole, vinblastine and paclitaxel are known to effect cell movement and migration by acting on the cell's microtubules. Colchicine, nocodazole and vinblastine disrupt the cell's normal tubulin equilibrium. These drugs "tie up" the tubulin that is present in the cell cytoplasm. This causes the tubulin that is present in the microtubules to disassemble and reenter the cytoplasm to reestablish equilibrium. These drugs also disrupt microtubule formation by interacting with binding sites on the microtubules, causing them to break up.

A first layer 150 having multiple orifices was applied to a support 140. The orifices (100 mM diameter holes, separated by 500 mM) were rendered inert to the adsorption of proteins and the adhesion of cells using the standard procedures described in earlier disclosures: silanes terminated with ethylene glycol groups were reacted covalently with the surface of the PDMS devices. The stencil was washed three times with PBS, and vacuum was applied for two minutes to remove air bubbles. Human microvasular endothelial cells from lung (HMVEC-L, Clonetics/Biowhittaker), were seeded into the macro-wells of the stencil at a density of $5 \times 10^3$ cells/cm2 into the dishes in growth medium (EGM, Clonetics/Biowhittaker), and washed with fresh medium after an initial attachment period of 30 minutes to one hour. After an overnight incubation in the membranes, cells were treated with the following microtubule-disrupting agents: nocodazole (10 mg/ml), colchicine (10 mg/ml), vinblastine (10 mg/ml), or paclitaxel (10 mg/ml). Control cells were left untreated. Two different experiments were then performed.

In the first experiment, cells were treated with the compounds while maintained within the macro-wells of the stencil. After two hours of treatment, the cells were imaged, the stencil was peeled off, and the cells were fixed with cold methanol (−20° C.) for ten minutes and washed three times with PBS. Immunofluorescence staining was performed using a monoclonal antibody to alpha-tubulin (1:100 dilution, DM1a, Sigma), followed by a FITC-conjugated goat anti-mouse antibody (25 mg/ml, Rockland Immunochemicals) and DAPI (3 mg/ml, Sigma) to stain the nucleus. Stained cells were mounted under a glass coverslip with Fluoromount G (Southern Biotechnology Associates) and imaged in a Zeiss fluorescence microscope.

In the second experiment, the stencil was peeled at the time of compound addition. After two hours of treatment, one set of samples was fixed and stained as described above. Another set of samples was left in the treatment compound and imaged over time, to monitor cell motility. Images were taken at 0, 2, 4, 8, and 24 hours. Cell motility was determined by taking the average diameter of the micro-regions, using ImageProPlus imaging software.

While several embodiments have been described above it should be understood that these are only illustrative and that others also within the spirit and scope of the present invention are also plausible.

We claim:

1. A system for monitoring cell movement comprising:
   a) a device for arraying cells
   b) an observation system configured to observe movement or lack of movement of arrayed cells; and
   c) a controller configured to link movement of the device for arraying cells into said observation system,
   the device for arraying cells comprising
   (i) a support;
   (ii) a first layer configured to be placed in fluid-tight contact with the support, the first layer having an upper surface and defining a pattern of micro-orifices, each micro-orifice of the pattern of micro-orifices having walls and defining a micro-region on the support when the first layer is placed in fluid-tight contact with the support such that the walls of said each micro-orifice and the micro-region on the support together define a micro-well;
   (ii) a second layer configured to be placed in fluid-tight contact with the upper surface of the first layer, the second layer defining a pattern of macro-orifices, each macro-orifice of the pattern of macro-orifices having walls and defining a macro-region when the first layer is placed in fluid-tight contact with the support and the second layer is placed in fluid-tight contact with the first layer such that the walls of the macro-orifice and the macro-region together define a macro-well wherein each macro-region encompasses at least one micro-region;

wherein the first layer and the second layer are configured for an arraying of cells on the support through the pattern of micro-orifices and the pattern of macro-orifices;

wherein the cells are allowed to grow to confluency within the micro-regions;

wherein at least one of a plurality of test agents is provided to at least one macro-well and allowing said test agent to contact confluent cells;

wherein said first and second layer are removed;

wherein cells are monitored for movement or lack of movement away from said micro-regions; and correlating cellular movement or lack of movement away from said micro-regions with effect of said test agent on cellular movement.

2. The system of claim 1 wherein the observation system comprises a phase contrast microscope or a flourescent image microscope.

3. The system of claim 1 wherein the controller further comprises a computer interface configured to coordinate the movement of the device into the observation system.

4. The system of claim 1 wherein the observation system further comprises a recording device configured to record images of the cells arrayed on the device for arraying cells.

5. The system of claim 4, wherein the recording device comprises a digital camera configured to record images of the cells arrayed on the device for arraying cells, and wherein the recorded images are in a digital output.

6. The system of claim 5, wherein the computer interface is configured to receive said digital output.

* * * * *

UNITED STATES PATENT AND TRADEMARK OFFICE
CERTIFICATE OF CORRECTION

PATENT NO. : 7,033,819 B2  Page 1 of 1
APPLICATION NO. : 10/206196
DATED : April 25, 2006
INVENTOR(S) : Kim et al.

It is certified that error appears in the above-identified patent and that said Letters Patent is hereby corrected as shown below:

| Column | Line | |
|---|---|---|
| 1 | 51 | Change "inflamation" to -- inflammation --; |
| 2 | 26 | Change "is" to -- are --; |
| 2 | 29 | Change "inflamation" to -- inflammation --; |
| 4 | 57 | Change "defineable" to -- definable --; |
| 14 | 50 | Change "flourescent" to -- fluorescent -- |
| 24 | 26 | Change "hexadecanethiold" to -- hexadecanekhiol --; |
| 36 | 37 | Change "flourescent" to -- fluorescent--; |
| 36 | 50 | Change "inflamation" to -- inflammation --; |
| 36 | 60 | Change "fibrobsis" to -- fibrosis --; |
| 38 | 53 | Change "wether" to -- whether --; and |
| 54 | 2 | Change "flourescent" to -- fluorescent --. |

Signed and Sealed this

Twenty-fourth Day of October, 2006

JON W. DUDAS
*Director of the United States Patent and Trademark Office*